(12) United States Patent
Zheng

(10) Patent No.: US 8,383,124 B2
(45) Date of Patent: Feb. 26, 2013

(54) MOBILIZATION OF HEMATOPOIETIC STEM CELLS

(75) Inventor: Yi Zheng, Cincinnati, OH (US)

(73) Assignee: Children's Hospital Medical Center, Cincinnati, OH (US)

(*) Notice: Subject to any disclaimer, the term of this patent is extended or adjusted under 35 U.S.C. 154(b) by 123 days.

(21) Appl. No.: 12/922,026

(22) PCT Filed: Mar. 12, 2009

(86) PCT No.: PCT/US2009/037013
§ 371 (c)(1),
(2), (4) Date: Sep. 10, 2010

(87) PCT Pub. No.: WO2009/114725
PCT Pub. Date: Sep. 17, 2009

(65) Prior Publication Data
US 2011/0020274 A1     Jan. 27, 2011

Related U.S. Application Data

(60) Provisional application No. 61/069,073, filed on Mar. 12, 2008.

(51) Int. Cl.
*A61K 39/00* (2006.01)
*A01N 25/00* (2006.01)
(52) U.S. Cl. .................................. 424/184.1; 514/885
(58) Field of Classification Search .......................... None
See application file for complete search history.

(56) References Cited

U.S. PATENT DOCUMENTS 7,122,570 B2   10/2006   Koppitz et al.
7,417,026 B2 *  8/2008   Williams et al. ............... 514/1.1

FOREIGN PATENT DOCUMENTS

| EP | 2014651 | 1/2009 |
|----|---------|--------|
| WO | WO 2005/017160 | 2/2005 |
| WO | WO 2005/037791 | 4/2005 |

OTHER PUBLICATIONS

Liu, et al., "Mobilization of Hematopoitic Stem/Progenitor Cells by a Cdc42 Activity-Specific Inhibitor" *Blood* (2008) 112: Abstract 68.
Nur-E-Kamal, et al., "The CDC42-specific inhibitor derived from ACK-1 blocks v-Ha-Ras-induced transformation" *Oncogene* (1999) 18: 7787-7793.
Pelish, et al., "The Cdc42 inhibitor secramine B prevents cAMP-induced $K^+$ conductance in intestinal epithelial cells" *Biochemical Pharmacology* (2006) 71: 1720-1726.
Yang, et al., "Rho GTPase Cdc42 coordinates hematopoietic stem cell quiescence and niche interaction in the bone marrow" *PNAS* (2007) 104(12): 5091-5096.
International Search Report dated Nov. 26, 2009, issued in International App. No. PCT/US2009/037013.

* cited by examiner

*Primary Examiner* — Michail Belyavskyi
(74) *Attorney, Agent, or Firm* — Knobbe, Martens, Olson & Bear LLP

(57) ABSTRACT

Methods, processes, uses, and pharmaceutical compositions are provided herein for mobilizing hematopoietic progenitor cells and/or cancer stem cells from bone marrow into peripheral blood, comprising the administration of an effective amount of an inhibitor of GTPases, such as a Cdc-42 specific inhibitor alone or in combination with one or more additional agents. Specifically, methods are disclosed for mobilizing hematopoietic stem cells into a subject's peripheral blood. In particular, embodiments of the method involve specific inhibition of the Cdc42 GTPase to increase the numbers of hematopoietic stem cells into a subject's peripheral blood of a subject.

2 Claims, 38 Drawing Sheets

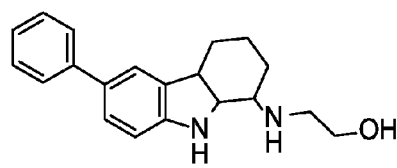
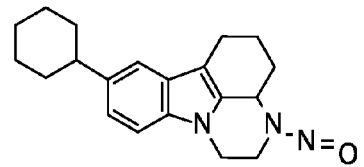
FIG. 1A
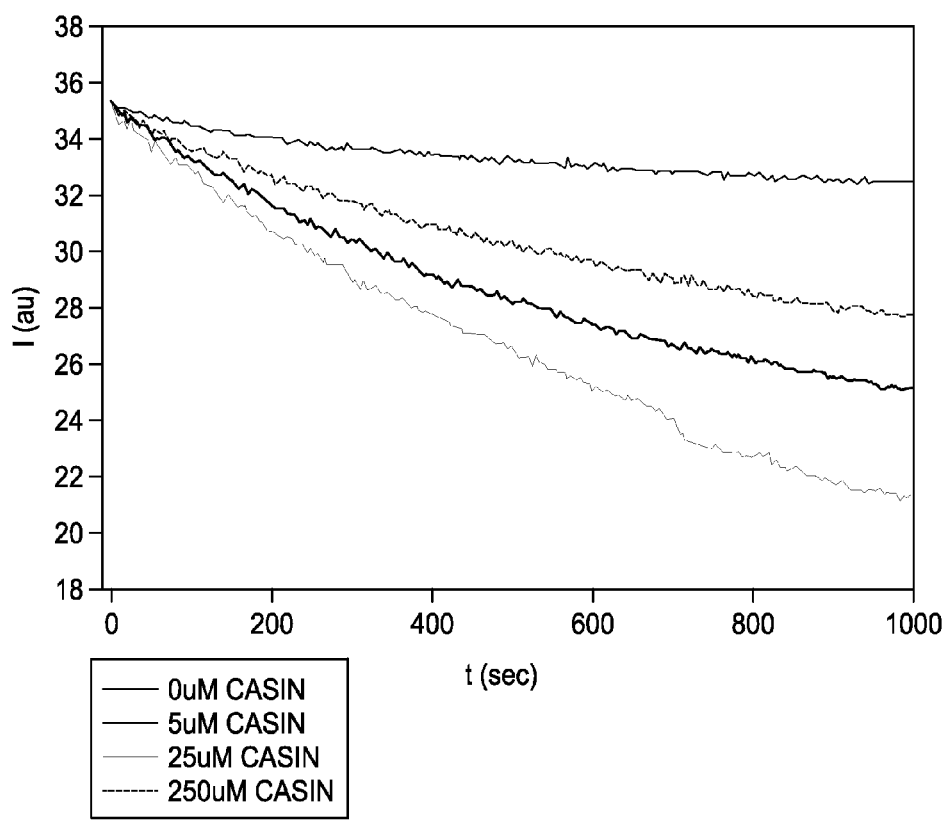
FIG. 1B

Adhesion

Migration

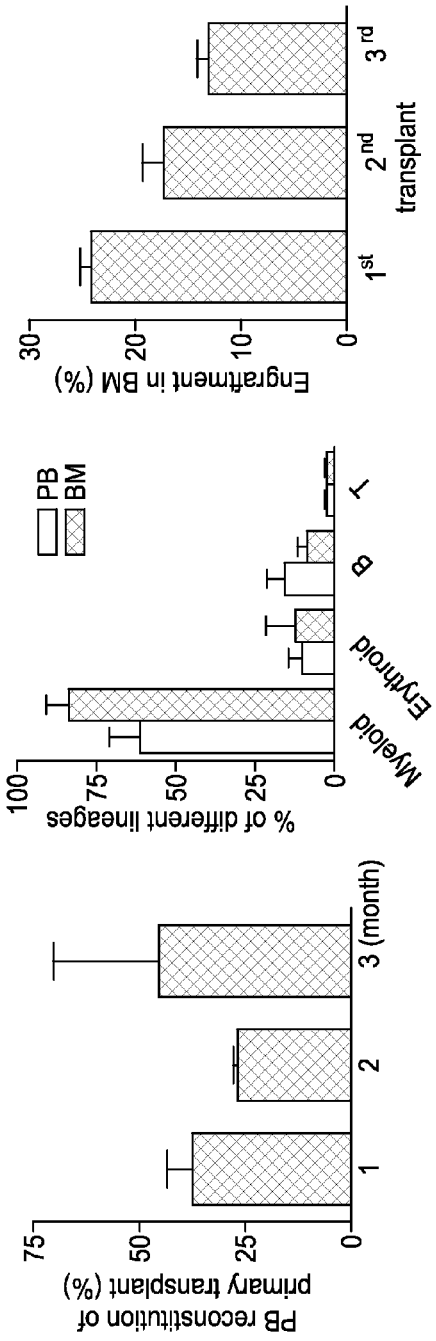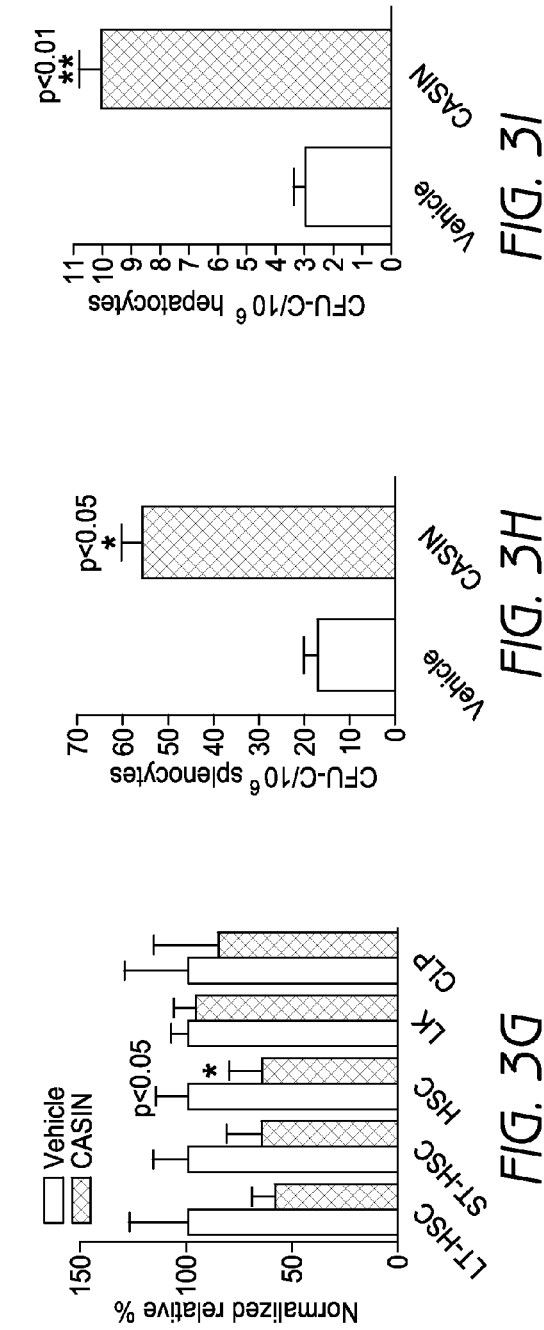

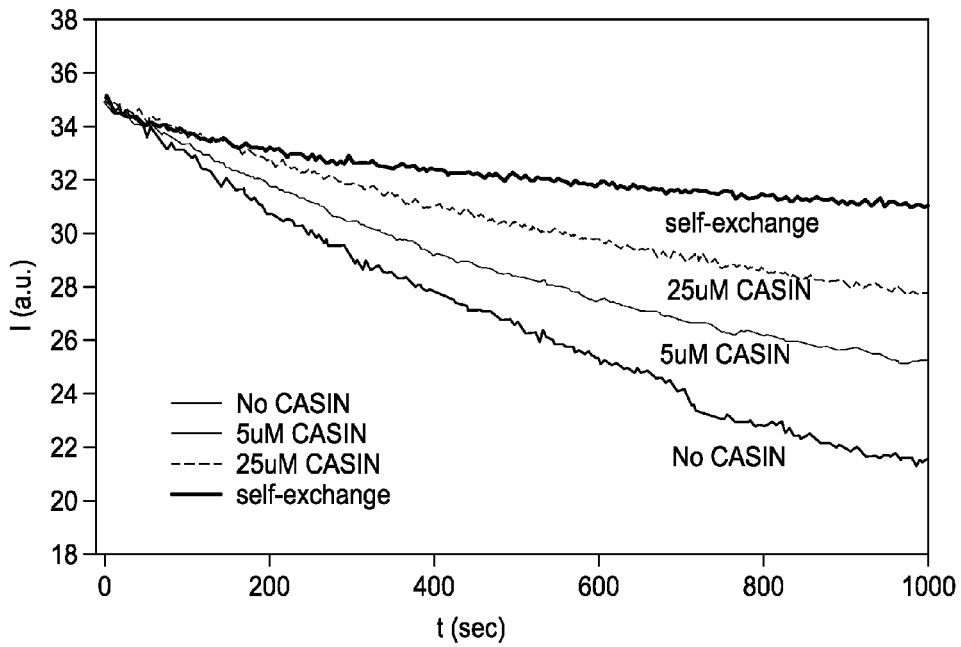
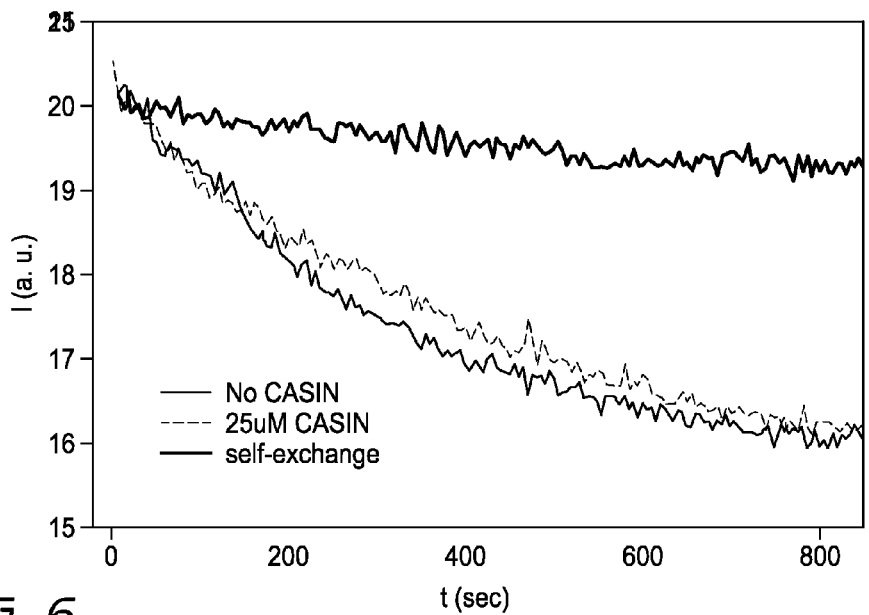
FIG. 6

Western blots on downstream effectors

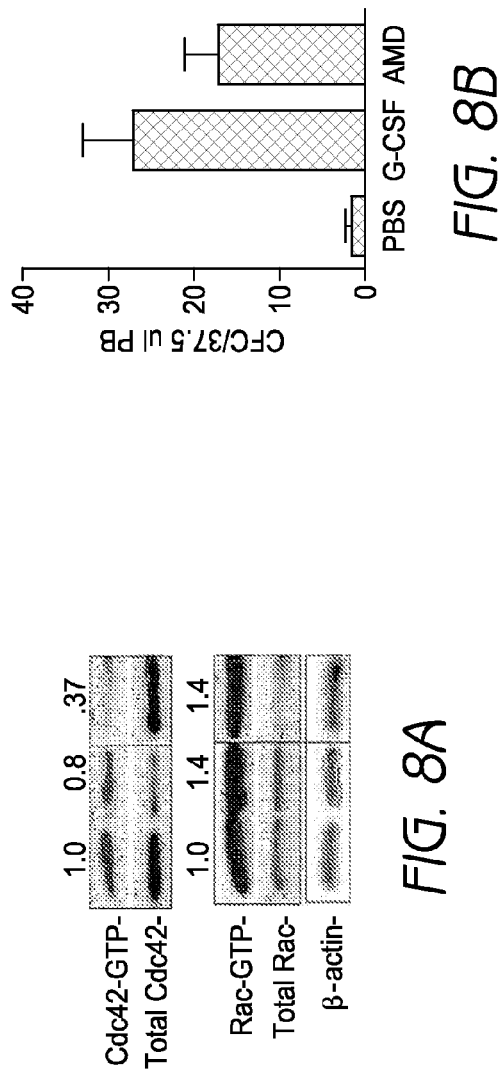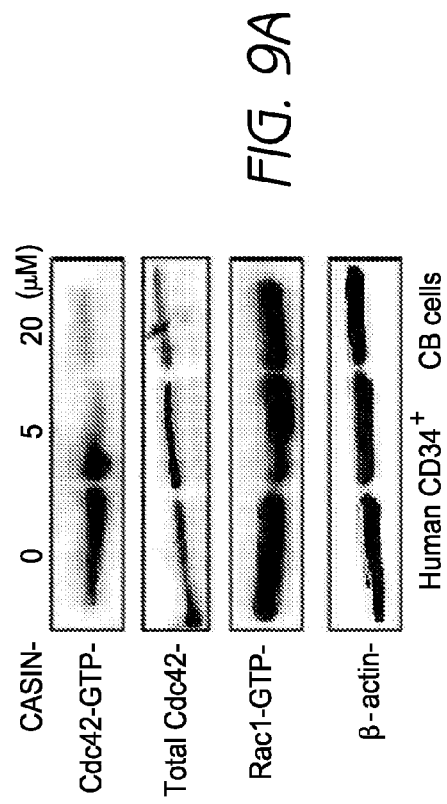

Multi-lineage engraftment of Cd34+ HCB in BM

| Mouse Label | 45+ | 45+/34+ | 45+/33+ | 45+/19+ | 45+/33+/19+ | 45+/33+/34+ | 45+/19+/34+ |
|---|---|---|---|---|---|---|---|
| 1-nc | 40.4 | 16.4 | 27.3 | 91.4 | 20 | 4.3 | 16.3 |
| 1-lc | 5.6 | 34.5 | 36.5 | 85.7 | 26 | 10.3 | 32.9 |
| 1-rc | 88.9 | 14.6 | 34.3 | 93 | 27.4 | 2.9 | 15.4 |
| 2-nc | 58.3 | 20 | 12.6 | 96 | 10.5 | 3.6 | 21.3 |
| 2-lc | 0.1 | 15.2 | 6.7 | 87.6 | 5.7 | 1 | 15.2 |
| 2-rc | 92 | 22.3 | 18.3 | 95.2 | 14.8 | 3.4 | 23.1 |
| 2-bc | 78.6 | 15 | 11.9 | 97.1 | 10.1 | 2.6 | 16 |
| 3-nc | 62.7 | 28.9 | 10.9 | 92.8 | 8.4 | 2.5 | 26.2 |
| 3-lc | 76.3 | 19.7 | 27 | 92.8 | 21.3 | 3.8 | 20.2 |
| 3-rc | 68.2 | 14.5 | 36.3 | 88.9 | 25.5 | 4.5 | 15 |
| 4-nc | 38.5 | 21 | 17.6 | 95.9 | 15.2 | 4.3 | 22.1 |
| 4-rc | 7.5 | 13.8 | 30.5 | 92.9 | 25.1 | 6 | 13.8 |

FIG. 11

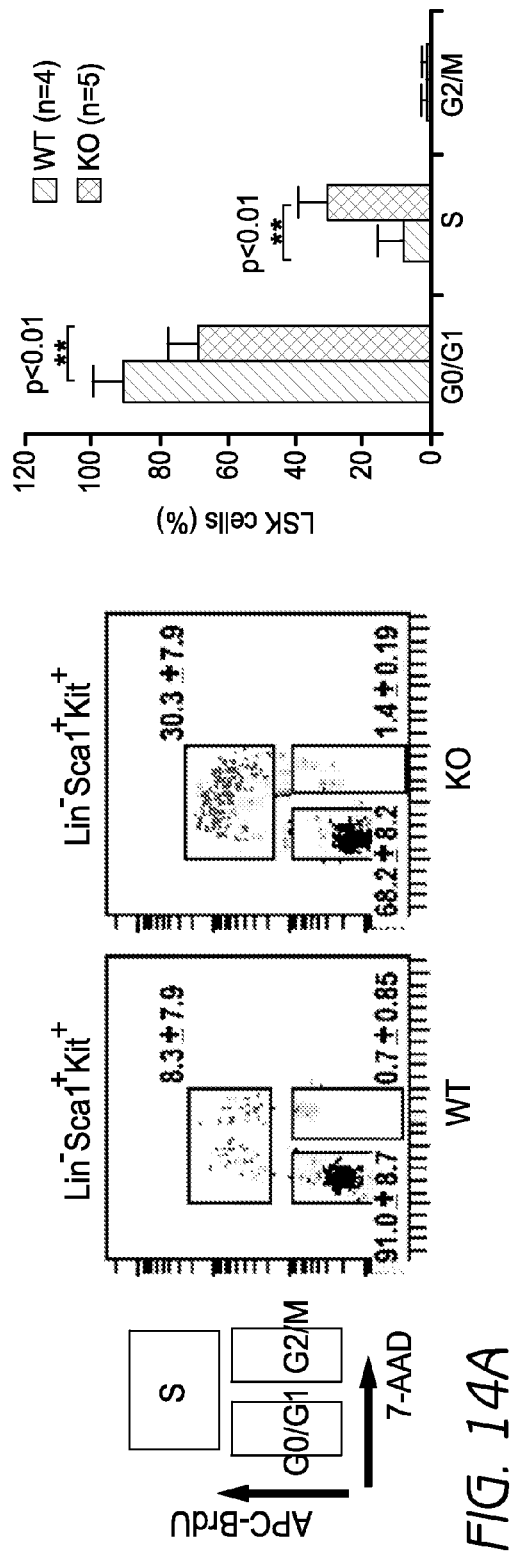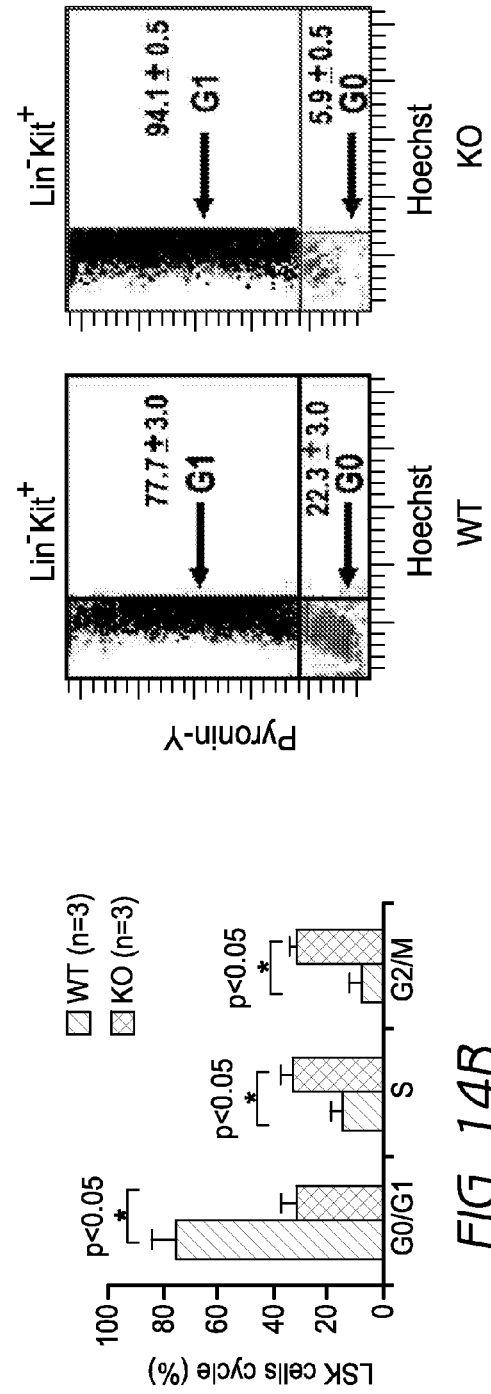
FIG. 14A
FIG. 14B
FIG. 14C

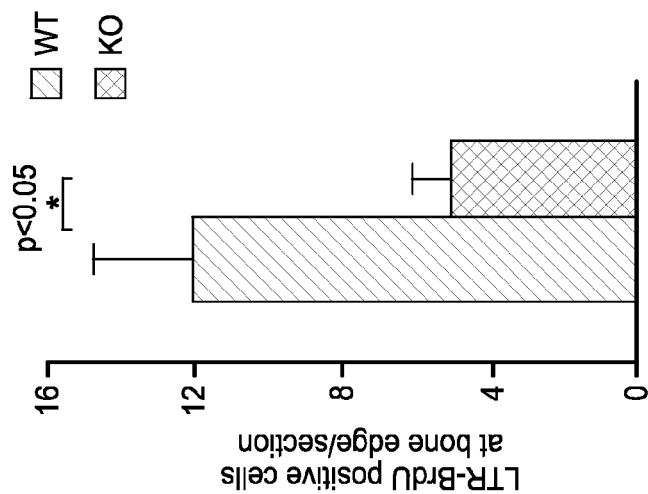
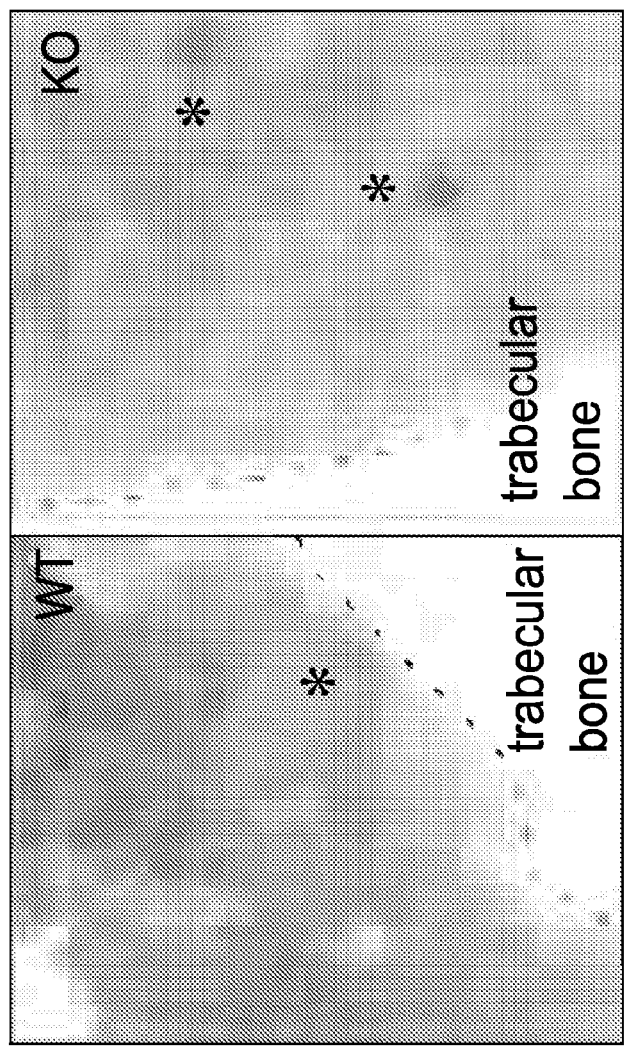
FIG. 15C

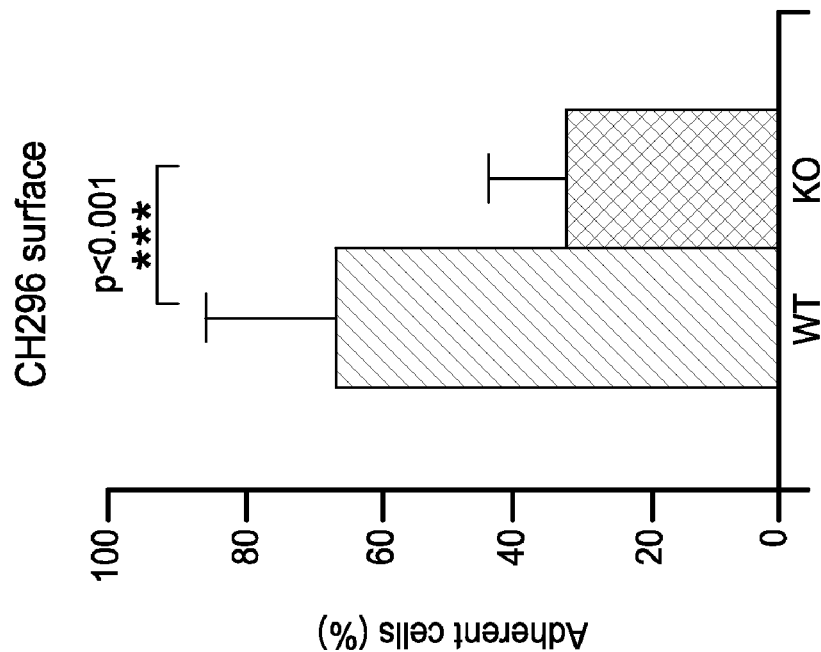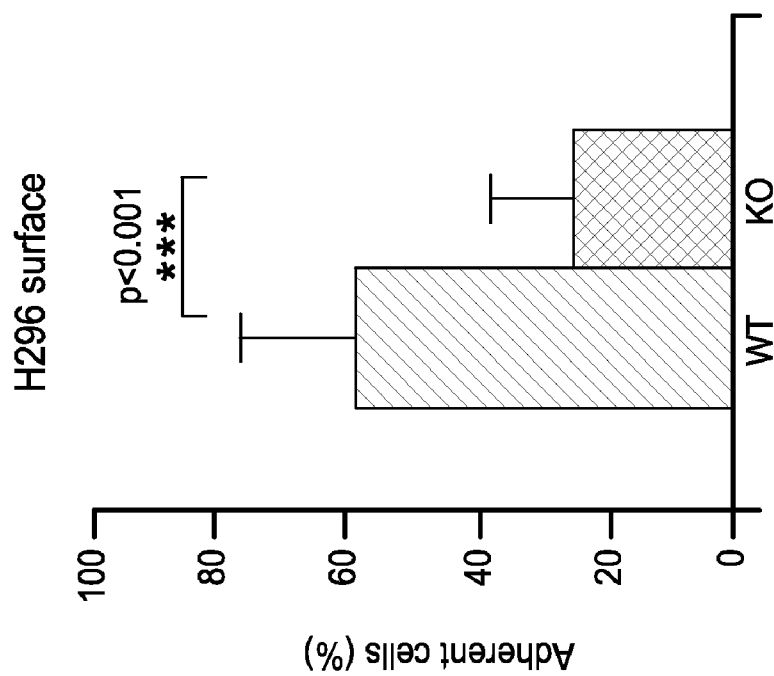
FIG. 16A

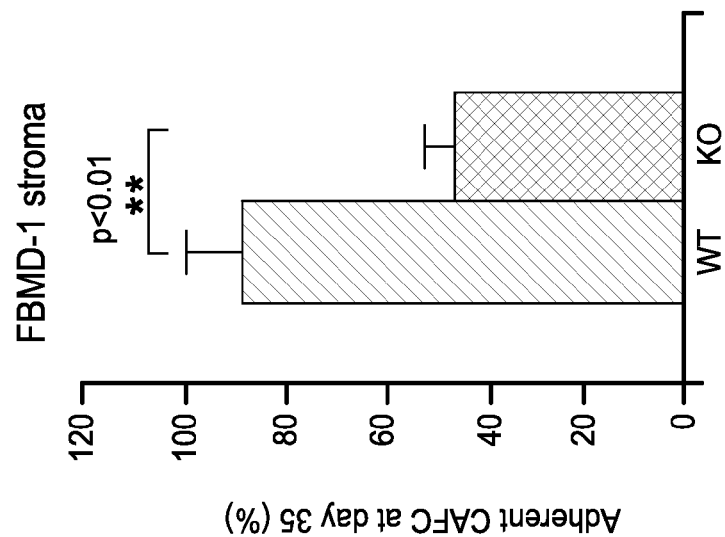
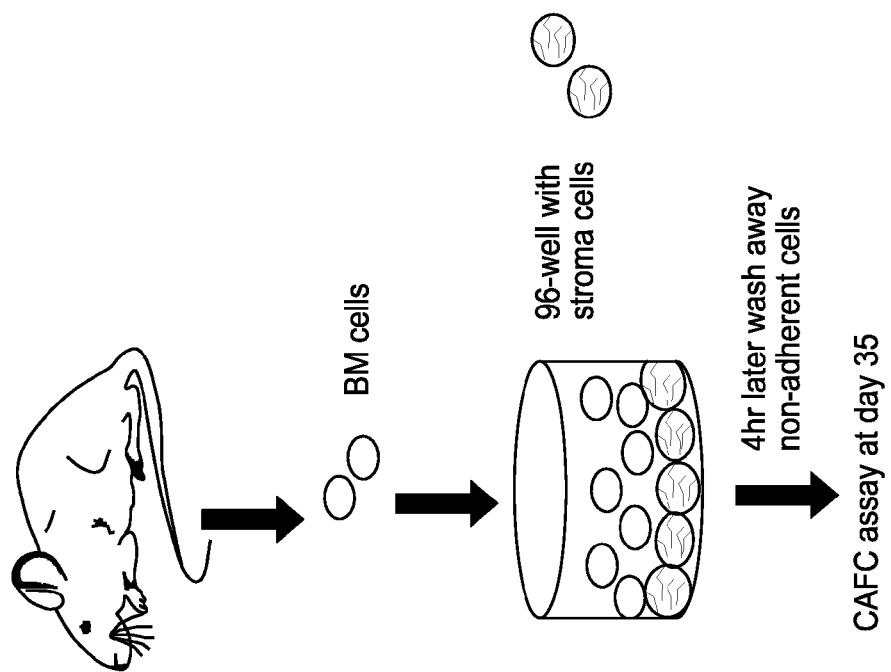
FIG. 16B

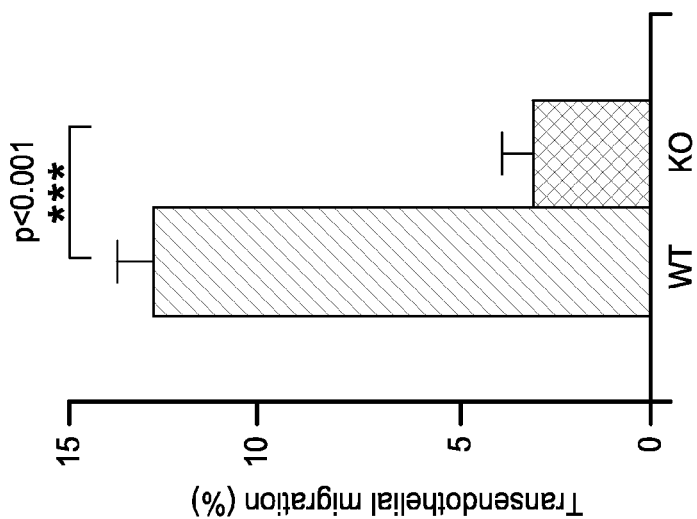
FIG. 16D
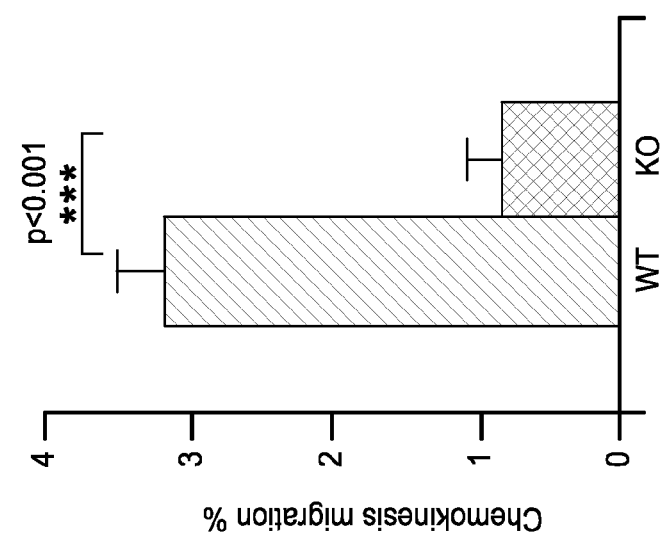
FIG. 16C
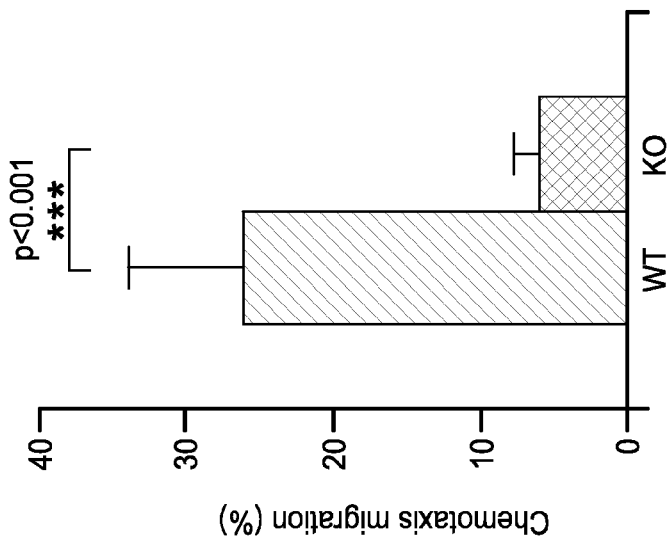

MOBILIZATION OF HEMATOPOIETIC STEM CELLS

CROSS-REFERENCE TO RELATED APPLICATIONS

This application is a U.S. National Phase of International Application No. PCT/US2009/037013, filed on Mar. 12, 2009 designating the U.S. and published on Sep. 17, 2009 as WO 2009/114725, which claims the benefit of U.S. Provisional Application No. 61/069,073, filed Mar. 12, 2008, which is hereby expressly incorporated by reference in its entirety.

FIELD OF THE INVENTION

The present invention relates generally to methods and pharmaceutical compositions for mobilizing hematopoietic stem and progenitor cell from bone marrow into peripheral blood by administration of at least one inhibitor of a GTPase, such as Cdc42 GTPase.

BACKGROUND OF THE INVENTION

Rho family GTPases are molecular switches that control signaling pathways regulating cytoskeleton reorganization, gene expression, cell cycle progression, cell survival, and other cellular processes (Etienne-Manneville, 2002), which is incorporated herein by reference in its entirety.

Rho family proteins constitute one of three major branches of the Ras superfamily. Rho proteins share approximately 30 percent amino acid identity with the Ras proteins. At least 14 mammalian Rho family proteins have been identified thus far, including RhoA, RhoB, RhoC, RhoD, RhoE/Rnd3, Rnd1/Rho6, Rnd2/Rho7, RhoG, Rac1, Rac2, Rac3, Cdc42, TC10, and TTF.

The various mature blood cell types are all ultimately derived from a single class of progenitor cell known as hematopoietic stem cells (HSCs). True stem cells are both pluripotent—that is they can give rise to all cell types—and capable of self-renewal. This is defined by their ability to repopulate an individual whose hematopoietic system has been destroyed by radiation or chemotherapy. Stem cells represent a very small percentage of bone marrow cells, and are normally quiescent. When stimulated to divide, they give rise to more committed, differentiated daughter cells with less proliferative potential, called "early progenitor" cells. Sequential rounds of division and differentiation give rise to an enormous amplification of cell numbers, necessary for the production of mature blood cells. This process of division and differentiation is subject to regulation at many levels to control cell production.

Leukocytic, hematopoietic cells are important in maintaining the body's defense against disease. For example, macrophages and lymphocytes are involved in potentiating the body's response to infection and tumors; granulocytes (neutrophils, eosinophils and basophils) are involved in overcoming infection, parasites and tumors. Other cell types derived from hematopoietic stem cells include platelets and erythrocytes.

Treatment of various cancers increasingly involves cytoreductive therapy, including high dose chemotherapy or radiation therapy. These therapies decrease a patient's white blood cell counts, suppress bone marrow hematopoietic activity, and increase the patient's risk of infection and/or hemorrhage. Depending on the degree of bone marrow damage (i.e., suppression), patients who undergo cytoreductive therapy must also receive therapy to reconstitute bone marrow function (hematopoiesis). Current treatments to manage the problems that result from prolonged bone marrow suppression include the reinfusion of a patient's own previously harvested hematopoietic stem and progenitor cells. In such procedures, patients undergo successive treatments with cell mobilization agents to cause mobilization of hematopoietic progenitor cells from the bone marrow to the peripheral circulation for harvesting. After harvesting, the patient is given high dose chemotherapy or radiotherapy and the bone marrow function is reconstituted by infusion of the cells harvested earlier.

The use of high-dosage chemotherapy or radiotherapy for bone marrow ablation requires subsequent incorporation of hematopoietic stem cells into the patient, in which case prior harvesting of such cells is required. The success of treatment crucially depends on the mobilization of the bone marrow stem cells, the subsequent return of which permits the patient to achieve reconstitution of a functioning hematopoietic system.

In many cases, successful mobilization is not effected in the patient and inadequate numbers of hematopoietic stem cells are harvested from these patients using current methods. Further, it is typically necessary to repeat the leukophoresis treatments, particularly if they are unsuccessful. This can be extremely stressful for the patient and the amount of stress increases with the number of repetitions.

Like normal HSCs, their malignant counterpart, leukemia initiating cells (LICs) reside in their BM niches that provide the structural and physiological conditions supporting their survival and growth. LICs are resistant to traditional chemotherapy by interacting with their BM microenvironment, which are the culprits of leukemia relapses after a period of remission induced by chemotherapy. In such instances, detachment of LICs from their niche by would be a valuable supplementary therapy to the traditional cancer therapies.

SUMMARY OF THE INVENTION

Embodiments disclosed herein relate to methods for mobilizing peripheral blood precursor cells from bone marrow into peripheral blood comprising: administering to a subject in need of treatment an effective amount of at least one Cdc42-specific inhibitor. In some embodiments, the peripheral blood precursor cells are hematopoietic cells selected from the group consisting of progenitor cells and stem cells. In some embodiments, the methods further comprise observing an increased mobility of peripheral blood precursor cells in the subject. In some embodiments, said observing comprises collecting a blood sample and counting the number of peripheral blood precursor cells. In some embodiments, the methods further comprise collecting mobilized stem cells for identification and/or analysis. In some embodiments, the methods further comprise administering a second agent prior to or concurrently with administering the Cdc42-specific inhibitor. In some embodiments, the second agent is selected from the group consisting of G-CSF, GM-CSF, IL-3, GM-CSF/IL-3 fusion proteins, FLK-2/FLT-3 ligand, stem cell factor, IL-6, IL-11, TPO, VEGF, AMD3100 and combinations thereof. In some embodiments, the second agent is G-CSF. In some embodiments, the second agent is AMD3100. In some embodiments, the Cdc42-specific inhibitor is a small molecule. In some embodiments the small molecule comprises a compound of formula (I). In some embodiments, the small molecule is Cdc42 Activity-Specific Inhibitor (CASIN). In the embodiments described herein, the chemical structure of CASIN is:

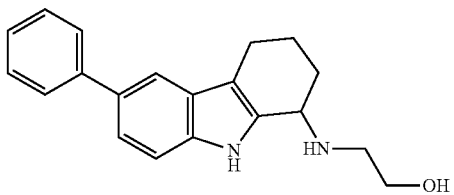 [SMILES: OCCNC1CCCc2c1[nH]c1ccc(-c3ccccc3)cc21]

Some embodiments disclosed herein relate to methods for facilitating hematopoietic reconstitution of peripheral blood precursor cells in a subject's hematopoietic organs, comprising: a) administering to the subject an effective amount of at least one Cdc42-specific inhibitor in the precursor cells; b) isolating mobilized peripheral blood precursor cells from the peripheral circulation of the subject; and c) infusing the isolated mobilized peripheral blood precursor cells into the subject. In some embodiments, the peripheral blood precursor cells are hematopoietic cells selected from the group consisting of progenitor cells and stem cells. In some embodiments, the methods further comprise administering a second agent prior to or concurrently with administering the Cdc42-specific inhibitor. In some embodiments, the second agent is selected from the group consisting of G-CSF, GM-CSF, IL-3, GM-CSF/IL-3 fusion proteins, FLK-2/FLT-3 ligand, stem cell factor, IL-6, IL-11, TPO, VEGF, AMD3100 and combinations thereof. In some embodiments, the second agent is G-CSF. In some embodiments, the second agent is AMD3100. In some embodiments, the hematopoietic cells are obtained from peripheral blood. In some embodiments, the hematopoietic cells are obtained from bone marrow. In some embodiments, the Cdc42-specific inhibitor is administered prior to a cancer therapy. In some embodiments, the Cdc42-specific inhibitor is administered simultaneously with a cancer therapy. In some embodiments, the Cdc42-specific inhibitor is administered after a cancer therapy. In some embodiments, the methods further comprise subsequently treating the subject with a second agent after infusing the isolated mobilized hematopoietic progenitor cells. The second agent can be a growth factor (e.g., G-CSF). The second agent can be a chemical agent (e.g., AMD3100). In some embodiments, the effective amount of the Cdc42-specific inhibitor is administered in a series of doses. In some embodiments, the Cdc42-specific inhibitor is a small molecule. In some embodiments, the small molecule comprises a compound of formula (I). In some embodiments, the small molecule is CASIN.

Further embodiments relate to methods for obtaining ex vivo expanded cells from a population of peripheral blood precursor cells, comprising: a) administering to the subject an effective amount of a Cdc42-specific inhibitor that is sufficient to cause the peripheral blood precursor cells to mobilize from the hematopoietic organs into the subject's peripheral circulation; b) isolating mobilized peripheral blood precursor cells from the peripheral circulation of the subject; and c) causing the isolated mobilized peripheral blood precursor cell population to expand to thereby obtain a therapeutically effective level of the cells.

Additional embodiments relate to methods for obtaining a therapeutically effective level of peripheral blood precursor cells, comprising: a) administering to a subject an effective amount of a Cdc42-specific inhibitor that is sufficient to cause the peripheral blood precursor cells to mobilize from the hematopoietic organs into the subject's peripheral circulation; and b) isolating mobilized peripheral blood precursor cells from the peripheral circulation of the subject to obtain a therapeutically effective level of the cells.

In any of the embodiments disclosed herein, an additional agent (e.g., a growth factor or a chemical agent) can be administered prior to, after, or concurrently with administering the Cdc42-specific inhibitor.

Other embodiments relate to methods of treating a condition in a subject in need of such treatment, comprising administering to the subject a hematopoietic stem cell mobilizing-effective amount (e.g., therapeutically effective amount) of at least one Cdc42-specific inhibitor.

More embodiments relate to methods to enhance the population of progenitor and/or stem cells, in a subject in need of such treatment, which method comprises administering to the subject a Cdc42-specific inhibitor in an amount effective to elevate the progenitor and/or stem cell population in the subject. In some embodiments, the subject exhibits a hematopoietic deficit from a cancer therapy. In some embodiments, the subject has a condition selected from the group consisting of leukemia, aplastic anemia, Fanconi anemia, and drug-induced anemia. In some embodiments, the subject is a transplantation recipient. In some embodiments, the subject is a healthy stem cell donor. In some embodiments, the progenitor and/or stem cells enhance wound healing. In some embodiments, the progenitor and/or stem cells ameliorate bacterial inflammation.

Additional embodiments relate to cancer therapy methods comprising: providing a Cdc42-specific inhibitor; and providing a chemotherapeutic agent, radiation, an antibody, or a biological agent specific for a cancer cell. In some embodiments, said Cdc42-specific inhibitor is a small molecule. In some embodiments, said small molecule comprises a compound of formula (I). In some embodiments, said small molecule is CASIN. In some embodiments, said cancer cells are resistant to said cancer therapy.

Further embodiments relate to methods of inhibiting, ameliorating, or ablation of cancer cells and/or tumors comprising: providing a Cdc42-specific inhibitor; and providing a cancer therapy comprising chemotherapeutic agent, radiation, an antibody, or a biological agent specific for a cancer cell. In some embodiments, said Cdc42-specific inhibitor is a small molecule. In some embodiments, said small molecule comprises a compound of formula (I). In some embodiments, said small molecule is CASIN. In some embodiments, said cancer cells and/or tumors are resistant to said cancer therapy.

Other embodiments relate to improved cancer therapy methods, wherein the improvement comprises providing a Cdc42-specific inhibitor to said cancer therapy. In some embodiments, said Cdc42-specific inhibitor is a small molecule. In some embodiments, said small molecule comprises a compound of formula (I). In some embodiments, said small molecule is CASIN. In some embodiments, the cancer cells and/or tumors are resistant to said cancer therapy.

Other embodiments relate to improved pharmaceutical compositions, wherein the improvement comprises a Cdc42-specific inhibitor. In some embodiments, said pharmaceutical composition is an anti-cancer pharmaceutical composition. In some embodiments, said Cdc42-specific inhibitor is a small molecule. In some embodiments, said small molecule comprises a compound of formula (I). In some embodiments, said small molecule is CASIN.

Some embodiments relate to the use of a Cdc42-specific inhibitor to sensitize a cancer cell to a cancer therapy. The cancer therapy can be, for example, chemotherapy or radiotherapy. In some embodiments, said Cdc42-specific inhibitor is a small molecule. In some embodiments, said small molecule comprises a compound of formula (I). In some embodiments, said small molecule is CASIN. In some embodiments, the cancer cells are resistant to said cancer therapy.

Additional embodiments relate to the use of a Cdc42-specific inhibitor in a medicament or therapy for cancer. In some embodiments, said Cdc42-specific inhibitor is a small molecule. In some embodiments, said small molecule comprises a compound of formula (I). In some embodiments, said small molecule is CASIN. In some embodiments, the cancer is resistant to chemotherapy or radiotherapy.

Further embodiments relate to methods of inhibiting the proliferation of cancer cells comprising: providing a Cdc42-specific inhibitor; and providing a therapy that inhibits proliferation of cancer cells. In some embodiments, the therapy that inhibits proliferation of cancer cells comprises a chemotherapeutic agent, radiation, an antibody, or a biological agent specific for a cancer cell. In some embodiments, said Cdc42-specific inhibitor is a small molecule. In some embodiments, said small molecule comprises a compound of formula (I). In some embodiments, said small molecule is CASIN. In some embodiments, said cancer cells are resistant to said therapy.

Some embodiments relate to cancer therapy methods comprising: providing a Cdc42-specific inhibitor. In some embodiments, said Cdc42-specific inhibitor is a small molecule. In some embodiments, said small molecule comprises a compound of formula (I). In some embodiments, said small molecule is CASIN.

Other embodiments relate to methods of identifying a hematopoietic stem cell mobilizing agent comprising: providing Cdc42 protein or a Cdc42 peptide; providing a target protein or a target peptide that binds the Cdc42 protein or the Cdc42 peptide; providing a compound; and assaying the ability of said compound to inhibit the binding of said Cdc42 protein or said Cdc42 peptide to said target protein or said target peptide, wherein said compound that inhibits said binding mobilizes hematopoietic stem cells.

Some embodiments relate to methods of identifying a hematopoietic stem cell mobilizing agent comprising: providing a sample comprising Cdc42 protein or peptide; providing a compound; assaying the ability of said compound to inhibit the GTPase activity of said Cdc42 protein or peptide, wherein said compound that inhibits said GTPase activity mobilizes hematopoietic stem cells.

Some embodiments relate to methods of identifying a hematopoietic stem cell mobilizing agent comprising: providing a sample comprising Cdc42 protein or peptide; providing a compound; assaying the ability of said compound to reduce the quantity of GTP-bound Cdc42 protein or peptide, wherein said compound that reduces said quantity of GTP-bound Cdc42 protein or peptide mobilizes hematopoietic stem cells.

Additional embodiments relate to processes for identifying a compound that enhances cancer therapy, comprising: providing a cancer therapy and contacting cancer cells with a Cdc42-specific inhibitor, wherein a first level of cancer inhibition is determined; providing the cancer therapy without the Cdc42-specific inhibitor, wherein a second level of cancer inhibition is determined; comparing the first level of cancer inhibition with the second level of cancer inhibition, wherein the Cdc42-specific inhibitor that enhances the cancer therapy is identified when said first level of cancer inhibition is greater than said second level of cancer inhibition. In some embodiments, the first level of cancer inhibition and second level of cancer inhibition is determined by measuring an inhibition of cell proliferation. In some embodiments, the first level of cancer inhibition and second level of cancer inhibition is determined by measuring the number of cancer cells killed. In some embodiments, the methods further comprise inputting the first and second levels of cancer inhibition into a computer configured to transform said first and second levels of cancer inhibition into a prognostic index using an algorithm. In some embodiments, the methods further comprise determining whether the solved prognostic index is associated with a synergistic effect by comparing the solved prognostic index to a database containing a plurality of prognostic indices, wherein some of the indices are associated with a synergistic effect.

Yet further embodiments relate to computerized systems for identifying a Cdc42-specific inhibitor that acts synergistically with a cancer therapy comprising: a first data base comprising a level of cancer inhibition determined by providing the cancer therapy and contacting cancer cells with the Cdc42-specific inhibitor; a second data base comprising a level of cancer inhibition determined by providing the cancer therapy without contacting cancer cells with the Cdc42-specific inhibitor; a search program that compares the first data base with the second database; and a retrieval program that identifies whether the Cdc42-specific inhibitor acts synergistically with the cancer therapy. In some embodiments, the cancer therapy comprises a chemotherapeutic agent, radiation, an antibody, or a biological agent specific for a cancer cell. In some embodiments, said Cdc42-specific inhibitor is a small molecule. In some embodiments, said small molecule comprises a compound of formula (I). In some embodiments, said small molecule is CASIN. In some embodiments, said cancer and/or cancer cells are resistant to said therapy.

Additional embodiments relate to methods for mobilizing peripheral blood precursor cells from bone marrow into peripheral blood comprising: administering to a subject in need of treatment an effective amount of at least one GTPase inhibitor. In some embodiments, the peripheral blood precursor cells are hematopoietic cells selected from the group consisting of progenitor cells and stem cells. In some embodiments, said GTPase inhibitor is an inhibitor of Cdc42.

Other embodiments relate to methods for facilitating hematopoietic reconstitution of peripheral blood precursor cells in a subject's hematopoietic organs, comprising: a) administering to the subject an effective amount of at least one active agent capable of inhibiting GTPases in the precursor cells, b) isolating mobilized peripheral blood precursor cells from the peripheral circulation of the subject; and c) infusing the isolated mobilized peripheral blood precursor cells into the subject. In some embodiments, the peripheral blood precursor cells are hematopoietic cells selected from the group consisting of progenitor cells and stem cells. In some embodiments, said GTPase inhibitor is an inhibitor of Cdc42. In some embodiments, the hematopoietic cells are obtained from peripheral blood. In some embodiments, the hematopoietic cells are obtained from bone marrow. In some embodiments, the active agent is administered prior to chemotherapy. In some embodiments, the active agent is administered simultaneously with chemotherapy. In some embodiments, the active agent is administered after chemotherapy. In some embodiments, the methods further comprise subsequently treating the subject with a growth factor after infusing the isolated mobilized hematopoietic progenitor cells. In some embodiments, the effective amount of the active agent is administered in a series of doses.

Some embodiments relate to methods for obtaining ex vivo expanded cells from a population of peripheral blood precursor cells, comprising: a) administering to the subject an effective amount of an active agent that is sufficient to cause the peripheral blood precursor cells to mobilize from the hematopoietic organs into the subject's peripheral circulation, wherein the active agent is at least one inhibitor of GTPase Cdc42; b) isolating mobilized peripheral blood precursor cells from the peripheral circulation of the subject; and c) causing the isolated mobilized peripheral blood precursor cell population to expand to thereby obtain a therapeutically effective level of the cells.

More embodiments relate to methods for obtaining a therapeutically effective level of peripheral blood precursor cells, comprising: a) administering to a subject an effective amount of an active agent that is sufficient to cause the peripheral blood precursor cells to mobilize from the hematopoietic organs into the subject's peripheral circulation, wherein the active agent inhibits GTPase Cdc42; and b) isolating mobilized peripheral blood precursor cells from the peripheral circulation of the subject to obtain a therapeutically effective level of the cells.

In some embodiments, the growth factor is administered prior to or concurrently with administering the active agent.

A method of treating a disease requiring peripheral stem cell transplantation in a subject in need of such treatment, comprising administering to the subject a hematopoietic stem cell mobilizing-effective amount of at least one active agent consisting of a GTPase Cdc42 inhibitor.

Additional embodiments relate to methods to enhance the population of progenitor and/or stem cells, in a subject, which method comprises administering to the subject an active agent capable of inhibiting GTPase Cdc42 in an amount effective to elevate the progenitor and/or stem cell population in the subject. In some embodiments, the subject exhibits a hematopoietic deficit from chemotherapy or radiation therapy. In some embodiments, the subject has a condition selected from the group consisting of aplastic anemia, Fanconi anemia, leukemia and drug-induced anemia. In some embodiments, the subject is a transplantation recipient. In some embodiments, the subject is a healthy stem cell donor. In some embodiments, the progenitor and/or stem cells enhance wound healing. In some embodiments, the progenitor and/or stem cells ameliorate bacterial inflammation. In some embodiments, the progenitor and/or stem cells restore damaged organ tissue. In some embodiments, the compound is administered to the subject by an intravenous or subcutaneous route.

Further embodiments relate to the use of an agent that specifically inhibits Cdc42 in the preparation of a medicament for mobilizing peripheral blood precursor cells from bone marrow into peripheral blood, wherein said agent is a small molecule. In some embodiments, the small molecule comprises a compound of formula (I). In some embodiments, the small molecule is CASIN. In some embodiments, the use is further characterized in that the mobilizing peripheral blood precursor cells from bone marrow into peripheral blood is for treating a condition or disease requiring peripheral stem cell transplantation.

Additional embodiments relate to the use of an agent that specifically inhibits Cdc42 in the preparation of a medicament for the treatment of hematopoietic deficits from chemotherapy or radiation therapy, bone marrow ablation by irradiation, cancer, leukemia, leucopenia, congenital leucopenia, childhood or adult cyclic neutropenia, post-infective neutropenia, myelodysplastic syndrome, hematopoietic disorder, anemia, aplastic anemia, Fanconi anemial, drug-induced anemia, transplantation during and following immunosuppressive treatments, organ transplantation, wound healing, bacterial inflammation, immunodeficiency, retrovirus infection, human immunodeficiency virus (HIV) infection, myocardium regeneration, or autoimmunity, wherein said agent is a small molecule. In some embodiments, the use is further characterized in that the small molecule comprises the compound of formula (I). In some embodiments, the use is further characterized in that the small molecule is CASIN.

More embodiments relate to the use of isolated mobilized peripheral blood precursor cells from a subject who has previously been treated with an agent that specifically inhibits Cdc42 in the preparation of a medicament for the subject for facilitating hematopoietic reconstitution of peripheral blood precursor cells in a subject's hematopoietic organs, wherein said agent is a small molecule. In some embodiments, the use is further characterized in that the small molecule comprises the compound of formula (I). In some embodiments, the use is further characterized in that the small molecule is CASIN.

Other embodiments relate to the use of isolated mobilized peripheral blood precursor cells from a subject who has previously been treated with an agent that specifically inhibits Cdc42 in the preparation of a medicament for the subject for the treatment of hematopoietic deficits from chemotherapy or radiation therapy, bone marrow ablation by irradiation, cancer, leukemia, leucopenia, congenital leucopenia, childhood or adult cyclic neutropenia, post-infective neutropenia, myelodysplastic syndrome, hematopoietic disorder, anemia, aplastic anemia, Fanconi anemia drug-induced anemia, transplantation during and following immunosuppressive treatments, organ transplantation, wound healing, bacterial inflammation, immunodeficiency, retrovirus infection, human immunodeficiency virus (HIV) infection, myocardium regeneration, or autoimmunity, wherein said agent is a small molecule. In some embodiments, the use is further characterized in that the small molecule comprises the compound of formula (I). In some embodiments, the use is further characterized in that the small molecule is CASIN.

Additional embodiments relate to methods for obtaining a medicament as disclosed and described herein, comprising isolating mobilized peripheral blood precursor cells from the peripheral circulation of the subject who has previously been treated with said agent that specifically inhibits Cdc42. In some embodiments, the methods additionally comprise causing the isolated mobilized peripheral blood precursor cell population to expand to thereby obtain a therapeutically effective level of the cells.

In any of the embodiments described herein, said Cdc42-specific inhibitor, said hematopoietic stem cell mobilizing agent, said compound that enhances cancer therapy, said GTPase inhibitor, said inhibitor of Cdc42, said inhibitor of GTPase Cdc42, said GTPase Cdc42 inhibitor, said agent capable of inhibiting GTPase Cdc42, or said agent that specifically inhibits Cdc42 comprises a compound of formula (I):

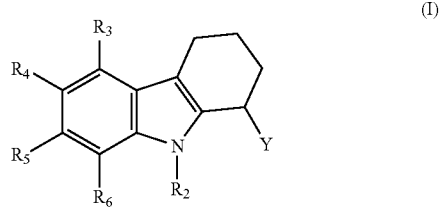

as a single isomer, a mixture of isomers, a racemic mixture of isomers, pharmaceutically acceptable salt, a solvate, metabolite or polymorph thereof, wherein:

Y is selected from the group consisting of OR7, NR8R9, and NNR8R9;

R7 is selected from the group consisting of C1-6 alkyl, (CH2)uC3-7cycloalkyl, C2-6 alkenyl, C1-6 alkoxy, hydroxy- C1-6 alkyl, phenyl, C1-6 alkyl substituted with up to 5 fluoro, and C1-6 alkoxy substituted with up to 5 fluoro, said C1-6 alkyl, (CH2)uC3-7cycloalkyl, C2-6 alkenyl, C1-6 alkoxy, hydroxy-C1-6 alkyl, phenyl are each optionally substituted with one or more substituents each independently selected from the group consisting of halo, —CN, —OH, C1-6 alkoxyl, heteroaryl, R19, and OR20;

R8 and R9 are each separately a hydrogen, or separately selected from the group consisting of C1-6 alkyl, C3-7 cycloalkyl, and phenyl, said C1-6 alkyl, C3-7 cycloalkyl, and phenyl, each optionally substituted with one or more substituents each independently selected from the group consisting of halo, cyano, nitro, hydroxy, C1-6 alkyl, —(CH2)uC3-7cycloalkyl, C2-6 alkenyl, C1-6 alkoxy, hydroxy-C1-6 alkyl, R19, OR20, C1-6 alkyl substituted with up to 5 fluoro, and C1-6 alkoxy substituted with up to 5 fluoro, each optionally substituted with one or more substituents each independently selected from the group consisting of halo, cyano, nitro, hydroxy, C1-6 alkyl, and C1-6 alkoxy; or R8 and R9 are optionally taken together with the nitrogen to which they are attached to form indolinyl, pyrrolidinyl, piperidinyl, piperazinyl, or morpholinyl, each optionally substituted with one or more substituents each independently selected from the group consisting of halo, cyano, nitro, hydroxy, C1-6 alkyl, (CH2)uC3-7cycloalkyl, C2-6 alkenyl, C1-6 alkoxy, hydroxy-C1-6 alkyl, phenyl, C1-6 alkyl substituted with up to 5 fluoro, and C1-6 alkoxy substituted with up to 5 fluoro; or R8 and R2 come together to be C1-3 alkyl linking together as a ring;

each u is independently 0, 1, 2, 3, or 4;

R2 is a hydrogen, or selected from the group consisting of C1-6 alkyl, C3-7 cycloalkyl, and phenyl, said C1-6 alkyl, C3-7 cycloalkyl, and phenyl, each optionally substituted with one or more substituents each independently selected from the group consisting of halo, cyano, nitro, hydroxy, C1-6 alkyl, —(CH2)uC3-7cycloalkyl, C2-6 alkenyl, C1-6 alkoxy, hydroxy-C1-6 alkyl, phenyl, C1-6 alkyl substituted with up to 5 fluoro, C1-6 alkoxy substituted with up to 5 fluoro, and —O(CH2)uphenyl optionally substituted with one or more substituents each independently selected from the group consisting of halo, cyano, nitro, hydroxy, C1-6 alkyl, and C1-6 alkoxy; or R8 and R2 come together to be C1-3 alkyl linking together as a ring;

R3, R4, R5 and R6 are each independently selected from the group consisting of: hydrogen, halo, cyano, nitro, hydroxy, C1-6 alkyl, (CH2)uC3-7cycloalkyl, —O(CH2)uC3-7cycloalkyl, C2-6 alkenyl, C1-6 alkoxy, hydroxy-C1-6 alkyl, phenyl, C1-6 alkyl substituted with up to 5 fluoro, and C1-6 alkoxy substituted with up to 5 fluoro, said C1-6 alkyl, (CH2)uC3-7cycloalkyl, —O(CH2)uC3-7cycloalkyl, C2-6 alkenyl, C1-6 alkoxy, hydroxy-C1-6 alkyl, and phenyl, each optionally substituted with one or more substituents each independently selected from the group consisting of halo, cyano, nitro, hydroxy, C1-6 alkyl, —(CH2)uC3-7cycloalkyl, C2-6 alkenyl, C1-6 alkoxy, hydroxy-C1-6 alkyl, phenyl, C1-6 alkyl substituted with up to 5 fluoro, and C1-6 alkoxy substituted with up to 5 fluoro, said phenyl optionally substituted with one or more substituents each independently selected from the group consisting of halo, cyano, nitro, hydroxy, C1-6 alkyl, —(CH2)uC3-7cycloalkyl, C2-6 alkenyl, C1-6 alkoxy, hydroxy-C1-6 alkyl, phenyl, C1-6 alkyl substituted with up to 5 fluoro, and C1-6 alkoxy substituted with up to 5 fluoro;

R19 is aryl optionally substituted with one or more substituents each independently selected from the group consisting of halo, cyano, nitro, hydroxy, C1-6 alkyl optionally substituted with up to 5 fluoro, and C1-6 alkoxy optionally substituted with up to 5 fluoro;

R20 is hydrogen or aryl optionally substituted with one or more substituents each independently selected from the group consisting of halo, cyano, nitro, hydroxy, C1-6 alkyl optionally substituted with up to 5 fluoro, and C1-6 alkoxy optionally substituted with up to 5 fluoro; and wherein when Y is NR8R9 then R8 and R2 optionally come together to be C1-3 alkyl linking together as a ring, with the proviso when R8 comes together with R2 to be C1-3 alkyl linking together as a ring then R4, is not substituted with hydroxyl.

In some embodiments, one, two or three of R3, R4, R5 and R6 are not hydrogen.

In some embodiments, R4 is C1-6 alkyl, (CH2)uC3-7cycloalkyl, —O(CH2)uC3-7cycloalkyl, C2-6 alkenyl, C1-6 alkoxy, phenyl, C1-6 alkyl substituted with up to 5 fluoro, and C1-6 alkoxy substituted with up to 5 fluoro, said C1-6 alkyl, (CH2)uC3-7cycloalkyl, —O(CH2)uC3-7cycloalkyl, C2-6 alkenyl, C1-6 alkoxy, and phenyl, each optionally substituted with one or more substituents each independently selected from the group consisting of haloC1-6 alkyl, —(CH2)uC3-7cycloalkyl, C2-6 alkenyl, C1-6 alkoxy, hydroxy-C1-6 alkyl, phenyl, C1-6 alkyl substituted with up to 5 fluoro, and C1-6 alkoxy substituted with up to 5 fluoro.

In some embodiments:

Y is NR8R9,

R8 is hydrogen; and R9 is C1-6 alkyl, said C1-6 alkyl, optionally substituted with one or more substituents each independently selected from the group consisting of hydroxy, R19 or OR20;

R19 is phenyl optionally substituted with one or more substituents each independently selected from the group consisting of halo, cyano, C1-6 alkyl optionally substituted with up to 5 fluoro, and C1-6 alkoxy optionally substituted with up to 5 fluoro; and R20 is hydrogen or phenyl optionally substituted with one or more substituents each independently selected from the group consisting of halo, cyano, nitro, hydroxy, C1-6 alkyl optionally substituted with up to 5 fluoro, and C1-6 alkoxy optionally substituted with up to 5 fluoro.

In some embodiments:

R19 is phenyl optionally substituted with one or more substituents each independently selected from the group consisting of halo, C1-6 alkyl, and C1-6 alkoxy; and R20 is phenyl optionally substituted with one or more substituents each independently selected from the group consisting of halo, C1-6 alkyl, and C1-6 alkoxy.

In some embodiments, R2 and R8 are hydrogen.

In some embodiments, Y is NR8R9 and R8 and R2 come together to be C1-3 alkyl linking together as a ring.

In some embodiments, R9 is hydrogen.

In some embodiments, R9 is C1-6 alkyl optionally substituted with one or more substituents each independently selected from the group consisting of hydroxy, R19 or OR20;

R19 is phenyl optionally substituted with one or more substituents each independently selected from the group consisting of halo, cyano, C1-6 alkyl optionally substituted with up to 5 fluoro, and C1-6 alkoxy optionally substituted with up to 5 fluoro; and R20 is hydrogen or phenyl optionally substituted with one or more substituents each independently selected from the group consisting of halo, cyano, nitro, hydroxy, C1-6 alkyl optionally substituted with up to 5 fluoro, and C1-6 alkoxy optionally substituted with up to 5 fluoro.

In some embodiments, R9 is hydrogen, or C1-6 alkyl, optionally substituted with one or more substituents each independently selected from the group consisting of hydroxyl R19 or OR20;

R19 is phenyl optionally substituted with one or more substituents each independently selected from the group consisting of halo, cyano, C1-6 alkyl optionally substituted with up to 5 fluoro, and C1-6 alkoxy optionally substituted with up to 5 fluoro; and R20 is hydrogen or phenyl optionally substituted with one or more substituents each independently selected from the group consisting of halo, cyano, nitro, hydroxy, C1-6 alkyl optionally substituted with up to 5 fluoro, and C1-6 alkoxy optionally substituted with up to 5 fluoro.

In some embodiments, R4 is C1-6 alkyl, (CH2)uC3-7cycloalkyl, —O(CH2)uC3-7cycloalkyl, C2-6 alkenyl, C1-6 alkoxy, phenyl, C1-6 alkyl substituted with up to 5 fluoro, and C1-6 alkoxy substituted with up to 5 fluoro, said C1-6 alkyl, (CH2)uC3-7cycloalkyl, —O(CH2)uC3-7cycloalkyl, C2-6 alkenyl, C1-6 alkoxy, and phenyl, each optionally substituted with one or more substituents each independently selected from the group consisting of halo, C1-6 alkyl, —(CH2)uC3-7cycloalkyl, C2-6 alkenyl, C1-6 alkoxy, phenyl, C1-6 alkyl substituted with up to 5 fluoro, and C1-6 alkoxy substituted with up to 5 fluoro, said phenyl optionally substituted with one or more substituents each independently selected from the group consisting of halo, C1-6 alkyl, —(CH2)uC3-7cycloalkyl, C2-6 alkenyl, C1-6 alkoxy, C1-6 alkyl substituted with up to 5 fluoro, and C1-6 alkoxy substituted with up to 5 fluoro.

In some embodiments, R4 is C1-6 alkyl, C3-7cycloalkyl, —OC3-7cycloalkyl, phenyl, C1-6 alkyl substituted with up to 5 fluoro, and C1-6 alkoxy substituted with up to 5 fluoro, said phenyl, optionally substituted with one or more substituents each independently selected from the group consisting of halo, C1-6 alkyl, C1-6 alkoxy, C1-6 alkyl substituted with up to 5 fluoro, and C1-6 alkoxy substituted with up to 5 fluoro.

In some embodiments, Y is NR8R9 and R8 and R2 come together to be C1-3 alkyl linking together as a ring.

In some embodiments, R2 is a hydrogen or C1-6 alkyl, C3-7 cycloalkyl, and phenyl, said C1-6 alkyl optionally substituted with one or more halo.

In some embodiments, R2 is a hydrogen.

In some embodiments, R9 is hydrogen, or C1-6 alkyl, optionally substituted with one or more substituents each independently selected from the group consisting of hydroxyl R19 or OR20;

R19 is phenyl optionally substituted with one or more substituents each independently selected from the group consisting of halo, cyano, C1-6 alkyl optionally substituted with up to 5 fluoro, and C1-6 alkoxy optionally substituted with up to 5 fluoro; and R20 is hydrogen or phenyl optionally substituted with one or more substituents each independently selected from the group consisting of halo, cyano, nitro, hydroxy, C1-6 alkyl optionally substituted with up to 5 fluoro, and C1-6 alkoxy optionally substituted with up to 5 fluoro.

In some embodiments, the compound of formula (I) is selected from the group consisting of:

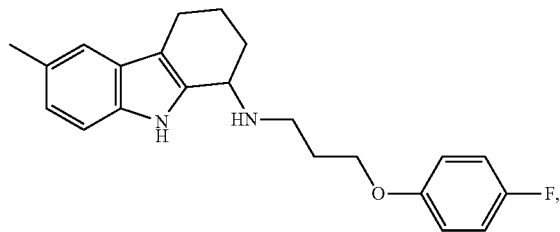

-continued

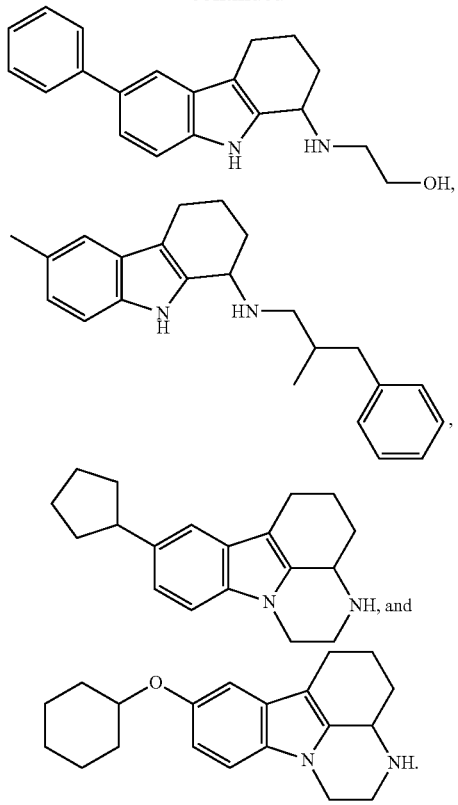

BRIEF DESCRIPTION OF THE DRAWINGS

FIG. 6. CASIN does not affect Tiam1 or Large induced nucleotide exchange of mant-GTP with Rac or Rho.

FIG. 8. CASIN inhibited Cdc42 activity in vivo in C57Bl/6 mice. (a) CASIN inhibited Cdc42 activity in BM cells harvested from C57Bl/6 mice 20 mins after CASIN administration. (b) G-CSF and AMD3100 led to mobilization of colony-forming progenitors determined by CFU-C assays similar to CASIN.

FIG. 11. Multi-lineage differentiation of donor derived cells from CD34$^+$ HCB xenografted NOD/SCID mouse model.

FIG. 14. Cdc42-deficiency causes cell cycle activation of HSCs. (A) LSK cells in mice were labeled with BrdU in vivo followed by FACS analysis to assess the cell cycle profile. (B) Freshly isolated LSK cells were pulse labeled with BrdU for 20 min in vitro. FACS analysis was performed to determine the cell cycle status. Data are representative of three independently performed experiments. (C) BM cells were stained for Lin$^-$c-Kit$^+$ markers and for Hoechst (DNA) and Pyronin Y (RNA) and were further analyzed for incorporation of the DNA and RNA dyes to assess the relative proportions in the G0 and G1 phases of the cell cycle.

and Lin⁻c-Kit⁺ BM cells (middle panel) lodging into a non-irradiated host was quantified. The spatial distribution of Lin⁻c-Kit⁺ BM cells is shown on the right hand panel. The stars indicate positive cells in BM and the dotted lines indicate the margin of bone surface. (C) Immunohistochemistry staining of BrdU-LTR cells was performed to reveal its relative localization to the trabecular bone surface (left hand panels). The stars indicate BrdU-positive cells in BM while the dotted lines depict the margin of bone surface. The relative percentage of BrdU-LTR cells within 20 cell diameter distance of the bone surface was quantified (right hand panel).

FIG. 16. Impaired adhesion, migration, and actin organization of stem/progenitor cells upon cdc42 deletion. (A) The adhesion activities of BM Lin⁻c-Kit⁺ cells to surfaces coated with recombinant fibronectin fragment were compared. (B) The adhesion activities of LT-HSCs (CAFC day 35) to FBMD-1 stroma cells were compared. (C) The chemotaxis migration of BM Lin-c-Kit+ cells in response to an SDF-1α gradient (left panel), and the chemokinesis migration of these cells without SDF-1α gradient (right panel) were shown. (D) The migration activity of progenitors through a mHEVc endothelial cell layer toward a SDF-1α gradient was measured. (E) Isolated Lin⁻c-Kit⁺BM cells were serum-starved and subsequently stimulated with SDF-1α and further stained with rhodamine-phalloidin for actin and DAPI for nucleus. Images shown are representative of more than 100 cells examined for each genotype.

FIG. 17. Altered gene expression of cell cycle and adhesion molecules in HSCs upon cdc42 deletion. (A) The mRNA levels of c-Myc, $p21^{Cip1}$, cyclin D1, β-catenin and $p27^{Kip1}$ in LSK cells were measured by RT-PCR. The transcript levels were normalized by using GAPDH as an internal control and to that of WT cells. (B) Relative mRNA transcripts of CXCR4, β1-integrin and N-cadherin in LSK cells were measured by RT-PCR and normalized by the internal GAPDH mRNA transcript and to that of WT cells.

Figure 18:
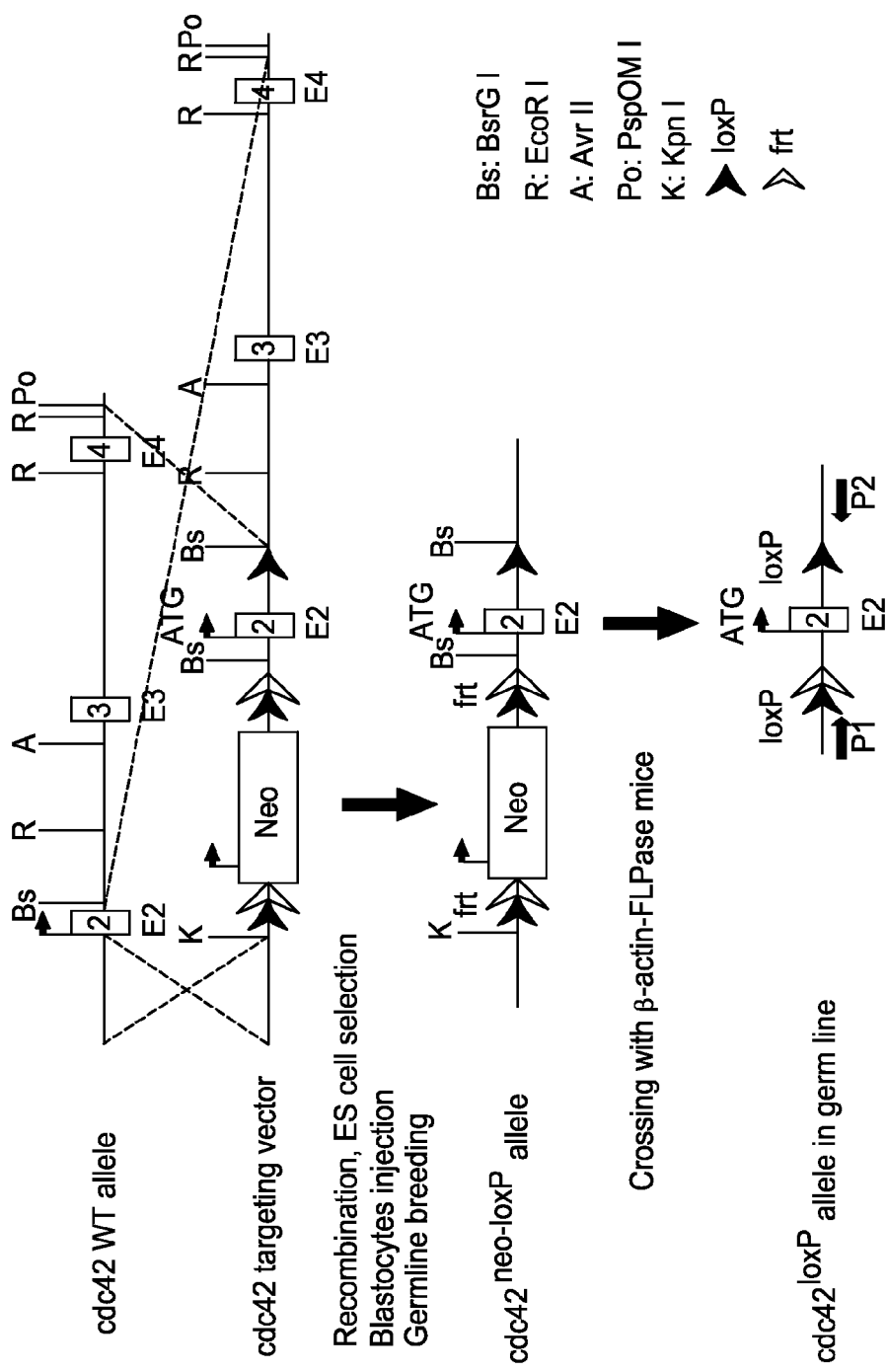

FIG. 18. Generation of cdc42 conditional knockout mice. Schematics of wild type cdc42 allele, the targeting vector, the predicted $cdc42^{neo-loxP}$ allele resulting from homologous recombination, and the $cdc42^{loxP}$ allele in the germ line following deletion of the neo cassette by crossing with β-actin-FLPase mice, are shown. To produce the targeting vector, a 2.0 kb neo cassette flanked by a pair of loxP and frt sites was inserted to the 5' region of exon 2 of cdc42 gene and a single loxp site was inserted to the 3' region of exon 2. Crossbreeding of $cdc42^{neo-loxP}$ allele carrying mice with β-actin-FLPase transgenics led to the deletion of DNA sequences flanked by two frt sites in all cell types. The germ line transmission of $cdc42^{loxP}$ allele was confirmed by multiple generations of out-breeding and genotyping analysis.

Figure 19:
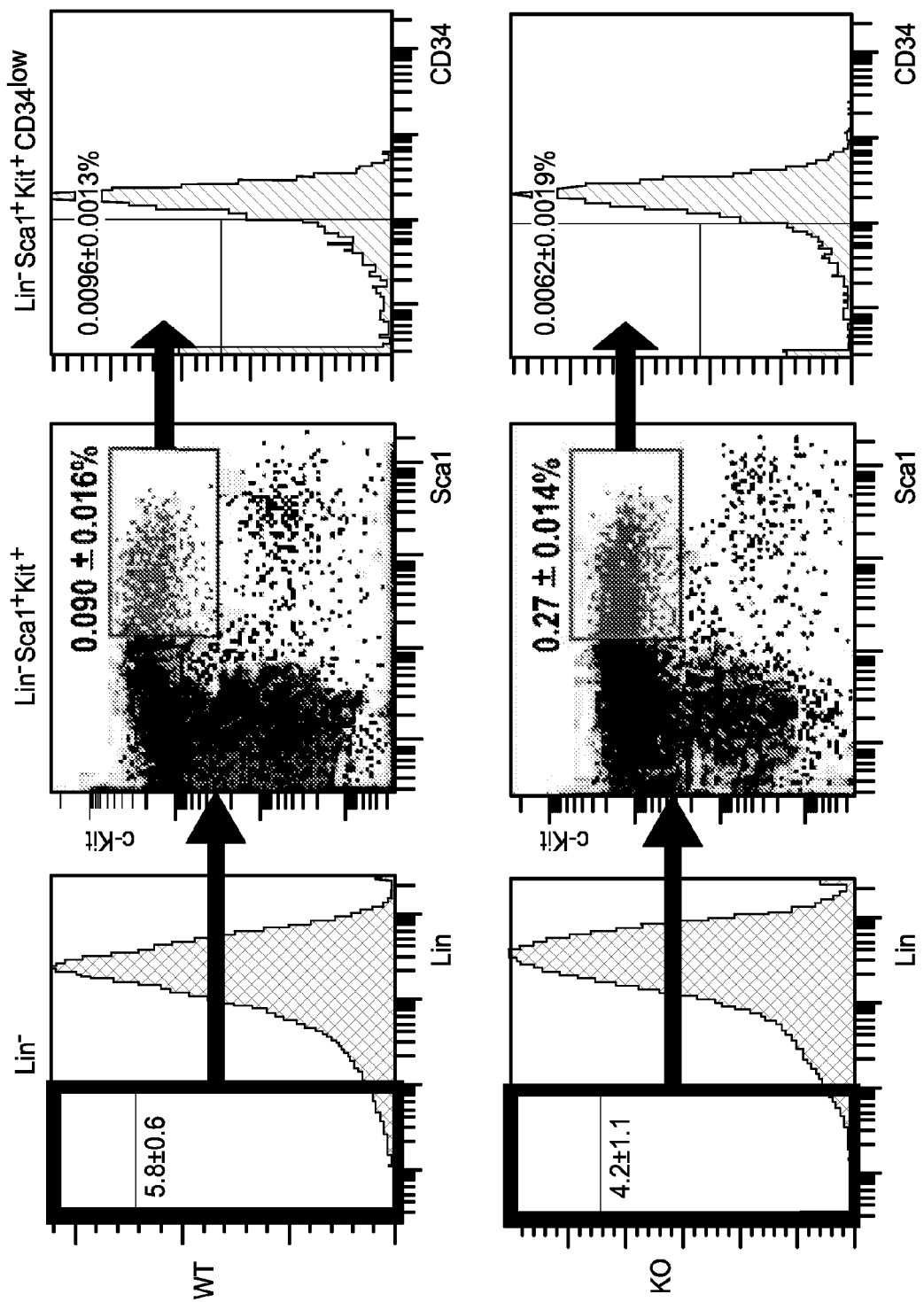

FIG. 19. Immunophenotypic analysis of HSCs in Cdc42⁻/⁻ mice. Representative FACS-staining profiles of progenitors and HSCs from the BM of WT and KO mice are shown 7-days post-polyI:C induction. The percentage of each genotype was calculated as percentage of total BM cells. The frequencies of LSK cells were increased while the Lin⁻Sca1⁺ c-Kit⁺Cd34$^{low}$ cells were decreased in KO mice. Data are representative of four independent experiments.

Figure 20:
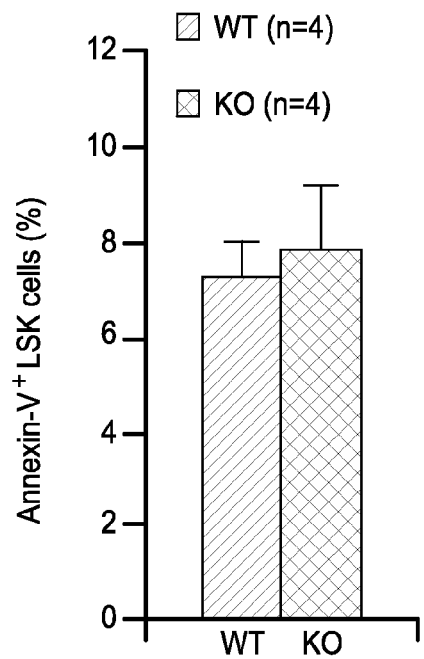

FIG. 20. Cdc42 deficiency does not significantly affect survival of LSK cells. Apoptotic LSK cell populations in BM were analyzed by Annexin-V staining.

Figure 21:
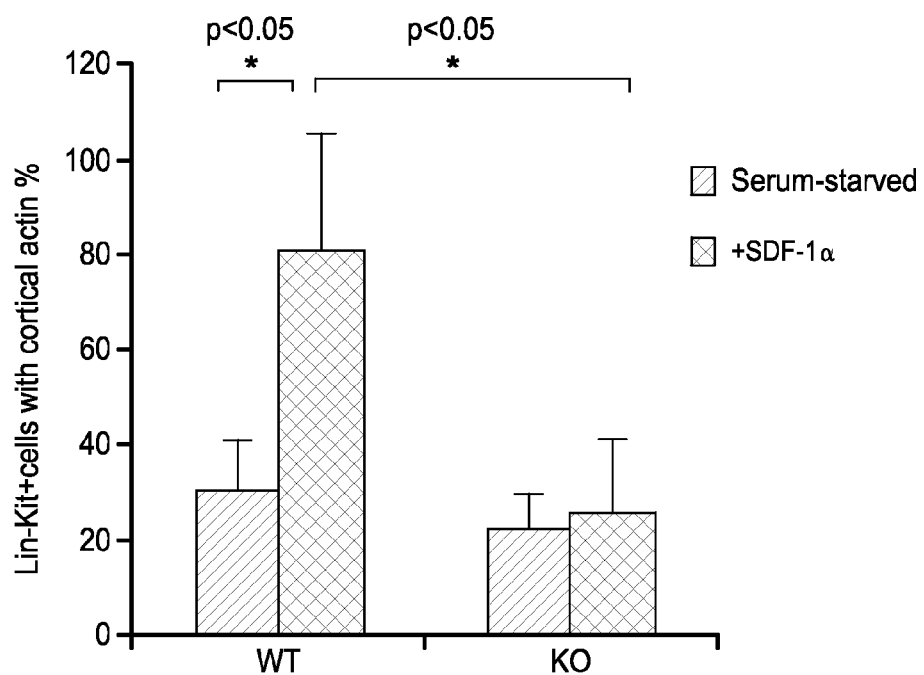

FIG. 21. Cdc42 deficiency causes defective cortical actin structure in HSCs. A quantification of cortical actin formation of isolated lin-c-Kit+ BM cells after SDF-1a-stimulation was performed as described in FIG. 16E.

DETAILED DESCRIPTION OF THE PREFERRED EMBODIMENT

The development of hematopoietic stem/progenitor cell (HSPC) mobilization agents that work through well defined molecular mechanisms, as an alternative for currently available G-CSF and AMD3100 regiments, remains desirable due to several limitations of currently practices. In the signal paradigm controlling HSPC localization at the bone marrow niche, the Rho family small GTPase Cdc42 situates at a nodal point that regulates multiple signal flows critical for HSPC maintenance. As described herein, Cdc42 knockout mice display impaired adhesion, homing, lodging, and retention of HSPCs, leading to massive egress of HSPCs from BM to peripheral blood without compromising their proliferative potential. A novel Cdc42 Activity-Specific Inhibitor (CASIN) was identified from an array of small molecule inhibitors of PIP2-induced actin-polymerization that shows specific interference for guanine nucleotide exchange on Cdc42 dose-dependently. CASIN specifically blocked Cdc42-mediated bradykinin induction of filopodia without affecting Rac or Rho regulated actin stress fiber or lamellipodia formation. In murine low density bone marrow (LDBM) cells, CASIN reversibly suppressed Cdc42 activity without a detectable toxic effect in either WT or Cdc42 deficient HSPCs in the dose range of 5-10 μM. CASIN treatment resulted in a reversible inhibition of F-actin polymerization induced by SDF-1α, α4β1 integrin mediated adhesion to fibronectin, and directional migration toward SDF-1α in WT HSPCs while it does not impact on Cdc42 knockout HSPCs. Upon injection into mice, CASIN was effective in stimulating mobilization of HSCs into the peripheral blood that was sufficient for reconstitution of various blood lineages in mice after serial transplantation. Consistent with the mobilization phenotype, intravenous injection of CASIN caused a transient reduction of hematopoietic stem cells (IL7Rα⁻Lin⁻Sca-1⁺ c-Kit⁺) in BM. Further, CASIN was active on human CD34⁺ umbilical cord blood cells in transiently suppressing F-actin assembly, adhesion to fibronectin, and SDF-1α induced migration and in mobilizing the human progenitors from engrafted immunodeficient mice. Finally, CASIN demonstrated similar efficacy in mobilizing leukemia initiating cells (LICs) in a human AML leukemia model, an effect associated with transient inhibition of LIC migration and F-actin reorganization. Advantageously, CASIN did not affect the proliferation of WT progenitors, nor showed any side effect on the KO cells as compared with the Cdc42 conditional knockout mouse. For example, CASIN did not cause myeloproliferative disorders (MPDs) or hyperactivation as compared with the Cdc42 conditional knockout mouse. These studies indicate that pharmacological targeting of Cdc42 is of value for development into a new HSC or LIC mobilization regiment.

The methods and compositions disclosed herein were identified during the search for additional and/or better methods to increase the number of hematopoeitic cells in a subject. The methods, processes, uses, and compositions described herein relate to approaches to mobilize hematopoietic cells from the bone marrow into the peripheral circulatory system of a subject. This is particularly advantageous for subjects requiring the uncomfortable and inconsistently successful method of leukophoresis, for example during a typical myeloablative or myelotoxic therapy. This is also advantageous for subjects requiring detachment of cancer stem cells (e.g., leukemia initiating cells (LICs)) from their BM microenvironment. For example, detachment of LICs from their niche would be a valuable supplementary therapy to the traditional cancer therapies (e.g., chemotherapies). The object of achieving a superior yield of stem cells or a decrease in the number of leukophereses via enhanced mobilization of stem cells, resulted in the following methods and compounds.

The identification of the involvement of GTPases (e.g., Cdc42) in the mobilization process resulted in methods and compounds which allowed for mobilization by inhibiting GTPases. More particularly, Cdc42-specific inhibitors (e.g., compounds of formula (I), such as CASIN) can be used for the mobilization of hematopoeitic stem/progenitor cells. This allows the novel use of an active compound to produce a pharmaceutical preparation for enhanced mobilization of hematopoietic stem cells (e.g., in the treatment of diseases requiring peripheral stem cell transplantation). In addition, a pharmaceutical packaging unit is disclosed containing an active compound and informational instructions regarding the application of an active compound or a combination of other agents for enhanced mobilization of hematopoietic stem cells prior to the onset of a corresponding therapy.

In some embodiments, the methods, compositions, and kits allow for increasing white blood cell survival following chemotherapy by administration of at least one GTPase inhibitor. In some embodiments, the GTPase inhibitor is at least one Cdc42-specific inhibitor (hereinafter referred to also as "active compound" or "compound").

In some embodiments, the methods, compositions, and uses can be particularly suitable for those subjects in need of repeated or high doses of chemotherapy. For some cancer subjects, hematopoietic toxicity frequently limits the opportunity for chemotherapy dose escalation or completion of prescribed treatments. Repeated or high dose cycles of chemotherapy may be responsible for severe stem cell depletion leading to important long-term hematopoietic sequelae and marrow exhaustion. This may also lead to significant problems in harvesting stem cells. In some embodiments, the methods provide for improved mortality and blood cell count when used in conjunction with chemotherapy.

Some embodiments relate to methods for mobilizing peripheral blood precursor cells from bone marrow into peripheral blood by administering at least one GTPase inhibitor (e.g., a Cdc42-specific inhibitor). The methods can mobilize peripheral blood precursor cells such as hematopoietic cells like progenitor cells and stem cells. In some embodiments, the methods also include observing an increased mobility of peripheral blood precursor cells in a subject such as by collecting a blood sample and counting the number of peripheral blood precursor cells. In some embodiments, methods can also include collecting mobilized stem cells for identification and/or analysis. In some embodiments, the GTPase inhibitor is at least one inhibitor of Cdc42.

In other embodiments, the methods, compositions, and uses relate to the use of an active compound (e.g., a Cdc42-specific inhibitor) or a combination of agents, including, e.g., chemotherapeutic agents, to produce a pharmaceutical preparation for enhanced mobilization of hematopoietic stem cells in the treatment of diseases requiring peripheral stem cell transplantation. In some embodiments, an active compound and the chemotherapeutic agent are formulated in separate administration forms, so that they can be taken out separately and administered successively according to the optimum application regimen. In some embodiments, it is preferred to apply the active compound after the administration of chemotherapeutic agents, during recovery, in order to enhance the mobilization of hematopoietic stem cells.

According to other embodiments, the active compound(s) may be administered prior to the onset of the administration of chemotherapeutic agents in order to enhance the mobilization and collection of hematopoietic stem cells.

Additional embodiments relate to methods of treating cancer, cancer therapy methods, and/or methods of inhibiting the proliferation of cancer cells comprising providing a Cdc42-specific inhibitor (e.g., CASIN), either alone, or in combination with one or more additional agents or therapies. In some embodiments, a Cdc42 specific inhibitor can cause apoptosis of cancer stem cells (e.g., leukemia stem cells such as LICs).

As described herein, it is intended that where a range of values is provided, it is understood that each intervening value, to the tenth of the unit of the lower limit unless the context clearly dictates otherwise, between the upper and lower limit of that range and any other stated or intervening value in that stated range is encompassed within the embodiments. The upper and lower limits of these smaller ranges may independently be included in the smaller ranges is also encompassed within the embodiments, subject to any specifically excluded limit in the stated range. Where the stated range includes one or both of the limits, ranges excluding either both of those included limits are also included in the embodiments.

Unless defined otherwise, all technical and scientific terms used herein have the same meaning as commonly understood by one of ordinary skill in the art to which the embodiments belong. Although any methods and materials similar or equivalent to those described herein may also be used in the practice or testing of the embodiments, the preferred methods and materials are now described. All publications mentioned herein are expressly incorporated by reference in their entireties.

As used herein and in the appended claims, the singular forms "a," "and," and "the" include plural referents unless the context clearly dictates otherwise. Thus, for example, reference to "a method" includes a plurality of such methods and reference to "a dose" includes reference to one or more doses and equivalents thereof known to those skilled in the art, and so forth.

In some contexts, the terms "individual," "host," "subject," and "patient" are used interchangeably to refer to an animal that is the object of treatment, observation and/or experiment. "Animal" includes vertebrates and invertebrates, such as fish, shellfish, reptiles, birds, and, in particular, mammals. "Mammal" includes, without limitation, mice, rats, rabbits, guinea pigs, dogs, cats, sheep, goats, cows, horses, primates, such as monkeys, chimpanzees, and apes, and, in particular, humans.

The term "about" or "approximately" means within an acceptable error range for the particular value as determined by one of ordinary skill in the art, which will depend in part on how the value is measured or determined, e.g., the limitations of the measurement system. For example, "about" can mean within 1 or more than 1 standard deviations, per the practice in the art. Alternatively, "about" can mean a range of up to 20%, preferably up to 10%, more preferably up to 5%, and more preferably still up to 1% of a given value. Alternatively, particularly with respect to biological systems or processes, the term can mean within an order of magnitude, preferably within 5-fold, and more preferably within 2-fold, of a value. Where particular values are described in the application and claims, unless otherwise stated the term "about" meaning within an acceptable error range for the particular value should be assumed.

As used herein, the term "heterologous sequence or gene" means a nucleic acid (RNA or DNA) sequence, which is not naturally found in association with the nucleic acid sequences of the specified molecule. The section below provides greater detail on some approaches that can be used to prepare inhibitors of Cdc42.

Mobilization of Hematopoietic Cells

The disclosure provides for a GTPase inhibitor and a method of mobilizing hematopoietic progenitor cells. In some embodiments, the GTPase inhibitor is a Cdc42-specific inhibitor. The methods disclosed herein relate to the novel use of an active compound or a combination of chemotherapeutic agents to produce a pharmaceutical preparation for enhanced mobilization of hematopoietic stem cells in the treatment of diseases (e.g., cancers, such as leukemia, or anemias, such as Fanconi anemia), disorders, and/or conditions requiring stem cell transplantation as is the case, e.g., in high-dosage chemotherapy or bone marrow ablation by irradiation. In addition, embodiments disclosed herein relate to a pharmaceutical packaging unit containing an active compound (e.g., a Cdc42-specific inhibitor), one or more additional agents (e.g., chemotherapeutic agent(s)) and informational instructions regarding the application of the an active compound and the chemotherapeutic agent or the combination of chemotherapeutic agents for enhanced mobilization of hematopoietic stem cells prior to, concurrent with, or after the onset of a corresponding therapy.

The inhibitors may be any GTPase inhibitors known to one of skill in the art, including, but not limited to: proteins, peptides, antibodies, nucleic acids, and small molecules. In one aspect, the present invention provides methods and kits for increasing progenitor and stem cell survival and mobilization following chemotherapy by administration of Cdc42-specific inhibitors (Cdc42-specific inhibitors hereinafter referred to as "active compounds"). The term "active compounds" refers to any compound or combination of compounds capable of specifically or selectively inhibiting Cdc42 GTPase. A specific inhibitor or selective inhibitor for Cdc42 is an inhibitor with an $IC_{50}$ value in the micromolar or lower range. The $IC_{50}$ values of other Rho family proteins are each at least about 10 fold higher that the $IC_{50}$ value of a Cdc42-specific or a Cdc42-selective inhibitor.

In another aspect, methods, compositions, processes, uses and kits provided for mobilizing hematopoietic stem and progenitor cells from bone marrow into peripheral blood comprising the administration of the active compounds to a subject in need of such treatment. In some embodiments, the stem cells are harvested. The harvested stem cells can subsequently be used to treat a patient in need of a cancer therapy (e.g., chemotherapy).

The methods are also particularly suitable for those patients in need of repeated or high doses of chemotherapy. For some cancer patients, hematopoietic toxicity frequently limits the opportunity for chemotherapy dose escalation or completion of prescribed chemotherapy. Repeated or high dose cycles of chemotherapy can be responsible for severe stem cell depletion leading to important long-term hematopoietic sequelae and marrow exhaustion. The methods of the present invention provide for improved mortality and blood cell count when used in conjunction with chemotherapy.

In other embodiments, the use of an active compound and a chemotherapeutic agent or a combination of chemotherapeutic agents is provided to produce a pharmaceutical preparation for enhanced mobilization of hematopoietic stem cells in the treatment of diseases requiring stem cell transplantation. The active compound and the chemotherapeutic agent can be present formulated in separate administration forms, so that they can be taken out separately and administered successively according to the optimum application regimen. It is preferred to apply the active compound prior to the onset of the administration of chemotherapeutic agents in order to enhance the mobilization of hematopoietic stem cells.

In additional embodiments, the use of an active compound is provided to enhance mobilization of cancer stem cells (e.g., LICs) that are resistant to traditional cancer therapies (e.g., chemotherapy). The use of an active compound can sensitize the cancer cells to treatment with additional agents (e.g., a chemotherapeutic agent) or therapies (e.g., radiotherapy).

The combined use according to the invention of an active compound and chemotherapeutic agent relates to all those diseases requiring recovery of stem cells from the blood for subsequent peripheral transplantation, particularly cancer and/or tumor diseases.

Further aspects and advantages will be disclosed herein, that should be regarded as illustrative and not limiting the scope of this application.

Cdc42-specific Modulators and Inhibitors

Embodiments disclosed herein relate to compounds, compositions, pharmaceutical compositions, methods, uses, and kits that comprise at least one Cdc42-specific inhibitor. In some embodiments, the Cdc42-specific inhibitor can be a chemical inhibitor such as a small molecule (e.g., CASIN). Small molecules include, for example, chemical molecules with a low molecular weight (e.g. a molecular weight below 2000 daltons). Additionally, the Cdc42-specific inhibitor can be an siRNA molecule, an antisense molecule, a small RNA (e.g., a micro RNA) or modified nucleic acid, a ribozyme, an antibody (such as a neutralizing antibody), or a polypeptide (e.g., a dominant negative peptide). Any type of inhibitor which is known to one of skill in the art may be used.

Another aspect of the preferred embodiments relates to the regulation of biological pathways in which a GTPase is involved, particularly pathological conditions, e.g., mobilization of hematopoietic cells, cell proliferation (e.g., cancer), growth control, morphogenesis, stress fiber formation, and integrin-mediated interactions, such as hematopoietic cell mobilization, cancer or tumor cell growth and metastasis, embryonic development, programmed cell death, hemostasis, leucocyte homing and activation, bone resorption, clot retraction, and the response of cells to mechanical stress. Thus, the preferred embodiments relate to all aspects of a method of modulating an activity of a Cdc42 GTPase comprising, administering an effective amount of an active agent, an effective amount of a compound which specifically and/or selectively modulates the activity of a Cdc42 GTPase, or combination thereof. The activity of Cdc42 which is modulated can include: GTP binding, GDP binding, GEF binding, GTPase activity, integrin binding, coupling or binding of Cdc42 to receptor or effector-like molecules (such as integrins, growth factor receptors, tyrosine kinases, PI-3K, PIP-5K, etc.). Increasing, reducing, antagonizing, or promoting Cdc42 can modulate the activity. The modulation of Cdc42 can be measured by assay for GTP hydrolysis, binding to GEF, etc. An effective amount is any amount which, when administered, modulates the Cdc42 activity. The activity can be modulated in a cell, a tissue, a whole organism, in situ, in vitro (test tube, a solid support, etc.), in vivo, or in any desired environment.

The modulation of oncogenic transforming activity by an active agent, or derivatives thereof, can be measured according to various known procedures. A compound can be added at any time during the method (e.g., pretreatment of cells; after addition of GEF, etc.) to determine its effect on the oncogenic transforming activity of an active agent. Various cell lines can also be used.

Other assays for Cdc42-mediated signal transduction can be accomplished according to procedures known in the art, e.g., as described in U.S. Pat. Nos. 5,141,851; 5,420,334; 5,436,128; and 5,482,954, all of which are incorporated herein by reference in their entirety where permitted. In addition, peptides that inhibit the interaction, e.g., binding, between an active agent and a G-protein, such as Cdc42, can be identified.

The preferred embodiments also relate to a method of testing for and identifying an agent which modulates the activity of Cdc42 GTPase, or a biologically-active fragment thereof, or which modulates the binding between an active agent, or a biologically-active fragment thereof, and a GTPase, or a biologically-active fragment thereof, to which it binds.

By modulating, it is meant that addition of the agent affects the activity or binding. The binding or activity modulation can be affected in various ways, including inhibiting, blocking, preventing, increasing, enhancing, or promoting it. The binding or activity effect does not have to be achieved in a specific way, e.g., it can be competitive, noncompetitive, allosteric, sterically hindered, via cross-linking between the agent and the GEF or GTPase, etc. The agent can act on either the active agent or GTPase. The agent can be an agonist, an antagonist, or a partial agonist or antagonist. The presence or amount of binding can be determined in various ways, e.g., by assaying for an activity promoted or inhibited by the active agent, such as guanine nucleotide exchange, GTP hydrolysis, oncogenic transformation, etc. Such assays are described above and below, and are also known in the art. The agent can be obtained and/or prepared from a variety of sources, including natural and synthetic. It can comprise, e.g., amino acids, lipids, carbohydrates, organic molecules, nucleic acids, inorganic molecules, or mixtures thereof.

The agent can be added simultaneously or sequentially. For example, the agent can be added to the active agent and then the resultant mixture can be further combined with the GTPase. The method can be carried out in liquid on isolated components, on a matrix (e.g., filter paper, nitrocellulose, agarose), in cells, on tissue sections, etc.

The method further relates to obtaining or producing agents that have been identified according to the above-described method. The preferred embodiments also relate to products identified in accordance with such methods.

Small Molecules

Small molecule inhibitors can be used to specifically inhibit and/or modulate Cdc42 as disclosed herein. Any type of small molecule inhibitor which is known to one of skill in the art may be used. Many methods are known to identify small molecule inhibitors and commercial laboratories are available to screen for small molecule inhibitors. For example, chemicals can be obtained from the compound collection at Merck® Research Laboratories (Rahway, N.J.) or a like company. The compounds can be screened for inhibition of a Cdc42 by automated robotic screening in a 96-well plate format. For example, the compounds can be dissolved at an initial concentration of about 50 µM in DMSO and dispensed into the 96-well plate. The 96-well plate assay may contain an appropriate number of units of Cdc42 and target (a substrate). Compounds that cause greater than a 50% inhibition of Cdc42 activity can be further diluted and tested to establish the concentration necessary for a 50% inhibition of activity. In some embodiments, the screen will include Cdc42 protein and one or more of its binding proteins and candidate inhibitors. The inhibitory effect of screened compound to disrupt Cdc42 target binding can be monitored using, for example, an ELISA-type test with Cdc42 or the target immobilized on the surface and residual binding can be detected, for example, using antibodies of Cdc42 target (binding)-molecule conjugated to a reporter (e.g., alkaline phosphate). Binding assays can also be performed using surface plasmon resonance (SPR) based interaction screening including Cdc42 and it's binding target and inhibitor or any other assay screening protein interactions (eg. yeast two hybrid systems, immunoprecipitation, immunocapture experiments coupled to enymatic or FACS detection etc.). In some embodiments, the candidate Cdc42 inhibitor can be tested for its ability to inhibit Cdc42 GTPase activity using assays known in the art. In other embodiments, the Cdc42 inhibitor can be tested for its ability to reduce the quantity of GTP-bound Cdc42, for example, relative to the quantity GDP-bound Cdc42, using assays known in the art.

Information disclosed herein (e.g., polypeptide or nucleic acid sequences, data from assays, etc.) can be stored, recorded, and manipulated on any medium that can be read and accessed by a computer. As used herein, the words "recorded" and "stored" refer to a process for storing information on computer readable medium. A skilled artisan can readily adopt any of the presently known methods for recording information on a computer readable medium to generate manufactures comprising the nucleotide or polypeptide sequence information of this embodiment. A variety of data storage structures are available to a skilled artisan for creating a computer readable medium having recorded thereon a nucleotide or polypeptide sequence. The choice of the data storage structure will generally be based on the component chosen to access the stored information. Computer readable media include magnetically readable media, optically readable media, or electronically readable media. For example, the computer readable media can be a hard disc, a floppy disc, a magnetic tape, zip disk, CD-ROM, DVD-ROM, RAM, or ROM as well as other types of other media known to those skilled in the art. The computer readable media on which the sequence information is stored can be in a personal computer, a network, a server or other computer systems known to those skilled in the art.

Embodiments of the invention utilize computer-based systems that contain the information described herein and convert this information into other types of usable information (e.g., models for rational drug design). The term "a computer-based system" refers to the hardware, software, and any database used to analyze information (e.g., a Cdc42-specific inhibitor that enhances cancer therapy or a hematopoietic stem cell mobilizing agent), or fragments of these biomolecules so as to construct models or to conduct rational drug design. The computer-based system preferably includes the storage media described above, and a processor for accessing and manipulating the sequence data. The hardware of the computer-based systems of this embodiment comprise a central processing unit (CPU) and a database. A skilled artisan can readily appreciate that any one of the currently available computer-based systems are suitable.

In some embodiments, the computer system includes a processor connected to a bus that is connected to a main memory (preferably implemented as RAM) and a variety of secondary storage devices, such as a hard drive and removable medium storage device. The removable medium storage device can represent, for example, a floppy disk drive, a DVD drive, an optical disk drive, a compact disk drive, a magnetic tape drive, etc. A removable storage medium, such as a floppy disk, a compact disk, a magnetic tape, etc. containing control logic and/or data recorded therein can be inserted into the removable storage device. The computer system includes appropriate software for reading the control logic and/or the data from the removable medium storage device once inserted in the removable medium storage device. Information described herein can be stored in a well known manner in the main memory, any of the secondary storage devices, and/ or a removable storage medium. Software for accessing and processing these sequences (such as search tools, compare tools, and modeling tools etc.) reside in main memory during execution.

As used herein, "a database" refers to memory that can store an information described herein (e.g., levels of cancer inhibition, and values, levels or results from functional assays). Additionally, a "database" refers to a memory access component that can access manufactures having recorded thereon information described herein. In other embodiments, a database stores a "functional profile" comprising the values or levels and results (e.g., ability to mobilize hematopoietic stem cells or ability to enhance a cancer therapy) from one or more functional assays, as described herein or known in the art, and relationships between these values or results. The data and values or results from functional assays can be stored and manipulated in a variety of data processor programs in a variety of formats. For example, the sequence data can be stored as text in a word processing file, a html file, or a pdf file in a variety of database programs familiar to those of skill in the art.

A "search program" refers to one or more programs that are implemented on the computer-based system to compare information (e.g., levels of cancer inhibition). A search program also refers to one or more programs that compare one or more protein models to several protein models that exist in a database and one or more protein models to several peptides, peptidomimetics, and chemicals that exist in a database. A search program is used, for example, to compare levels of cancer inhibition by providing a cancer therapy to cancer cells with or without a compound (e.g., a Cdc42-specific inhibitor) that are present in one or more databases. Still further, a search program can be used to compare values, levels or results from functional assays.

A "retrieval program" refers to one or more programs that can be implemented on the computer-based system to identify a homologous nucleic acid sequence, a homologous protein sequence, or a homologous protein model. A retrieval program can also used to identify, for example, Cdc42-specific inhibitors that can mobilize hematopoietic stem cells or can enhance a cancer therapy. That is, a retrieval program can also be used to obtain a functional profile. Further, a functional profile can have one or more symbols that represent these molecules and/or models, an identifier that represents one or more inhibitors including, but not limited to values, levels, or results from a functional assay.

In any of the embodiments described herein, said Cdc42-specific inhibitor, said hematopoietic stem cell mobilizing agent, said compound that enhances cancer therapy, said GTPase inhibitor, said inhibitor of Cdc42, said inhibitor of GTPase Cdc42, said GTPase Cdc42 inhibitor, said agent capable of inhibiting GTPase Cdc42, or said agent that specifically inhibits Cdc42 comprises a compound of formula (I):

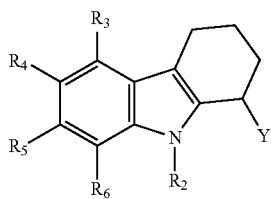

(I)

as a single isomer, a mixture of isomers, a racemic mixture of isomers, pharmaceutically acceptable salt, a solvate, metabolite or polymorph thereof, wherein:

Y is selected from the group consisting of OR7, NR8R9, and NNR8R9;

R7 is selected from the group consisting of C1-6 alkyl, (CH2)uC3-7cycloalkyl, C2-6 alkenyl, C1-6 alkoxy, hydroxy-C1-6 alkyl, phenyl, C1-6 alkyl substituted with up to 5 fluoro, and C1-6 alkoxy substituted with up to 5 fluoro, said C1-6 alkyl, (CH2)uC3-7cycloalkyl, C2-6 alkenyl, C1-6 alkoxy, hydroxy-C1-6 alkyl, phenyl are each optionally substituted with one or more substituents each independently selected from the group consisting of halo, —CN, —OH, C1-6 alkoxyl, heteroaryl, R19, and OR20;

R8 and R9 are each separately a hydrogen, or separately selected from the group consisting of C1-6 alkyl, C3-7 cycloalkyl, and phenyl, said C1-6 alkyl, C3-7 cycloalkyl, and phenyl, each optionally substituted with one or more substituents each independently selected from the group consisting of halo, cyano, nitro, hydroxy, C1-6 alkyl, —(CH2)uC3-7cycloalkyl, C2-6 alkenyl, C1-6 alkoxy, hydroxy-C1-6 alkyl, R19, OR20, C1-6 alkyl substituted with up to 5 fluoro, and C1-6 alkoxy substituted with up to 5 fluoro, each optionally substituted with one or more substituents each independently selected from the group consisting of halo, cyano, nitro, hydroxy, C1-6 alkyl, and C1-6 alkoxy; or R8 and R9 are optionally taken together with the nitrogen to which they are attached to form indolinyl, pyrrolidinyl, piperidinyl, piperazinyl, or morpholinyl, each optionally substituted with one or more substituents each independently selected from the group consisting of halo, cyano, nitro, hydroxy, C1-6 alkyl, (CH2)uC3-7cycloalkyl, C2-6 alkenyl, C1-6 alkoxy, hydroxy-C1-6 alkyl, phenyl, C1-6 alkyl substituted with up to 5 fluoro, and C1-6 alkoxy substituted with up to 5 fluoro; or R8 and R2 come together to be C1-3 alkyl linking together as a ring;

each u is independently 0, 1, 2, 3, or 4;

R2 is a hydrogen, or selected from the group consisting of C1-6 alkyl, C3-7 cycloalkyl, and phenyl, said C1-6 alkyl, C3-7 cycloalkyl, and phenyl, each optionally substituted with one or more substituents each independently selected from the group consisting of halo, cyano, nitro, hydroxy, C1-6 alkyl, —(CH2)uC3-7cycloalkyl, C2-6 alkenyl, C1-6 alkoxy, hydroxy-C1-6 alkyl, phenyl, C1-6 alkyl substituted with up to 5 fluoro, C1-6 alkoxy substituted with up to 5 fluoro, and —O(CH2)uphenyl optionally substituted with one or more substituents each independently selected from the group consisting of halo, cyano, nitro, hydroxy, C1-6 alkyl, and C1-6 alkoxy; or R8 and R2 come together to be C1-3 alkyl linking together as a ring;

R3, R4, R5 and R6 are each independently selected from the group consisting of: hydrogen, halo, cyano, nitro, hydroxy, C1-6 alkyl, (CH2)uC3-7cycloalkyl, —O(CH2) uC3-7cycloalkyl, C2-6 alkenyl, C1-6 alkoxy, hydroxy-C1-6 alkyl, phenyl, C1-6 alkyl substituted with up to 5 fluoro, and C1-6 alkoxy substituted with up to 5 fluoro, said C1-6 alkyl, (CH2)uC3-7cycloalkyl, —O(CH2)uC3-7cycloalkyl, C2-6 alkenyl, C1-6 alkoxy, hydroxy-C1-6 alkyl, and phenyl, each optionally substituted with one or more substituents each independently selected from the group consisting of halo, cyano, nitro, hydroxy, C1-6 alkyl, —(CH2)uC3-7cycloalkyl, C2-6 alkenyl, C1-6 alkoxy, hydroxy-C1-6 alkyl, phenyl, C1-6 alkyl substituted with up to 5 fluoro, and C1-6 alkoxy substituted with up to 5 fluoro, said phenyl optionally substituted with one or more substituents each independently selected from the group consisting of halo, cyano, nitro, hydroxy, C1-6 alkyl, —(CH2)uC3-7cycloalkyl, C2-6 alkenyl, C1-6 alkoxy, hydroxy-C1-6 alkyl, phenyl, C1-6 alkyl substituted with up to 5 fluoro, and C1-6 alkoxy substituted with up to 5 fluoro;

R19 is aryl optionally substituted with one or more substituents each independently selected from the group consisting of halo, cyano, nitro, hydroxy, C1-6 alkyl optionally substituted with up to 5 fluoro, and C1-6 alkoxy optionally substituted with up to 5 fluoro;

R20 is hydrogen or aryl optionally substituted with one or more substituents each independently selected from the group consisting of halo, cyano, nitro, hydroxy, C1-6 alkyl optionally substituted with up to 5 fluoro, and C1-6 alkoxy optionally substituted with up to 5 fluoro; and wherein when Y is NR8R9 then R8 and R2 optionally come together to be C1-3 alkyl linking together as a ring, with the proviso when R8 comes together with R2 to be C1-3 alkyl linking together as a ring then R4, is not substituted with hydroxyl.

In some embodiments, one, two or three of R3, R4, R5 and R6 are not hydrogen.

In some embodiments, R4 is C1-6 alkyl, (CH2)uC3-7cycloalkyl, —O(CH2)uC3-7cycloalkyl, C2-6 alkenyl, C1-6 alkoxy, phenyl, C1-6 alkyl substituted with up to 5 fluoro, and C1-6 alkoxy substituted with up to 5 fluoro, said C1-6 alkyl, (CH2)uC3-7cycloalkyl, —O(CH2)uC3-7cycloalkyl, C2-6 alkenyl, C1-6 alkoxy, and phenyl, each optionally substituted with one or more substituents each independently selected from the group consisting of haloC1-6 alkyl, —(CH2)uC3-7cycloalkyl, C2-6 alkenyl, C1-6 alkoxy, hydroxy-C1-6 alkyl, phenyl, C1-6 alkyl substituted with up to 5 fluoro, and C1-6 alkoxy substituted with up to 5 fluoro.

In some embodiments:
Y is NR8R9,
R8 is hydrogen; and R9 is C1-6 alkyl, said C1-6 alkyl, optionally substituted with one or more substituents each independently selected from the group consisting of hydroxy, R19 or OR20;

R19 is phenyl optionally substituted with one or more substituents each independently selected from the group consisting of halo, cyano, C1-6 alkyl optionally substituted with up to 5 fluoro, and C1-6 alkoxy optionally substituted with up to 5 fluoro; and R20 is hydrogen or phenyl optionally substituted with one or more substituents each independently selected from the group consisting of halo, cyano, nitro, hydroxy, C1-6 alkyl optionally substituted with up to 5 fluoro, and C1-6 alkoxy optionally substituted with up to 5 fluoro.

In some embodiments:
R19 is phenyl optionally substituted with one or more substituents each independently selected from the group consisting of halo, C1-6 alkyl, and C1-6 alkoxy; and R20 is phenyl optionally substituted with one or more substituents each independently selected from the group consisting of halo, C1-6 alkyl, and C1-6 alkoxy.

In some embodiments, R2 and R8 are hydrogen.

In some embodiments, Y is NR8R9 and R8 and R2 come together to be C1-3 alkyl linking together as a ring.

In some embodiments, R9 is hydrogen.

In some embodiments, R9 is C1-6 alkyl optionally substituted with one or more substituents each independently selected from the group consisting of hydroxy, R19 or OR20;

R19 is phenyl optionally substituted with one or more substituents each independently selected from the group consisting of halo, cyano, C1-6 alkyl optionally substituted with up to 5 fluoro, and C1-6 alkoxy optionally substituted with up to 5 fluoro; and R20 is hydrogen or phenyl optionally substituted with one or more substituents each independently selected from the group consisting of halo, cyano, nitro, hydroxy, C1-6 alkyl optionally substituted with up to 5 fluoro, and C1-6 alkoxy optionally substituted with up to 5 fluoro.

In some embodiments, R9 is hydrogen, or C1-6 alkyl, optionally substituted with one or more substituents each independently selected from the group consisting of hydroxyl R19 or OR20;

R19 is phenyl optionally substituted with one or more substituents each independently selected from the group consisting of halo, cyano, C1-6 alkyl optionally substituted with up to 5 fluoro, and C1-6 alkoxy optionally substituted with up to 5 fluoro; and R20 is hydrogen or phenyl optionally substituted with one or more substituents each independently selected from the group consisting of halo, cyano, nitro, hydroxy, C1-6 alkyl optionally substituted with up to 5 fluoro, and C1-6 alkoxy optionally substituted with up to 5 fluoro.

In some embodiments, R4 is C1-6 alkyl, (CH2)uC3-7cycloalkyl, —O(CH2)uC3-7cycloalkyl, C2-6 alkenyl, C1-6 alkoxy, phenyl, C1-6 alkyl substituted with up to 5 fluoro, and C1-6 alkoxy substituted with up to 5 fluoro, said C1-6 alkyl, (CH2)uC3-7cycloalkyl, —O(CH2)uC3-7cycloalkyl, C2-6 alkenyl, C1-6 alkoxy, and phenyl, each optionally substituted with one or more substituents each independently selected from the group consisting of halo, C1-6 alkyl, —(CH2)uC3-7cycloalkyl, C2-6 alkenyl, C1-6 alkoxy, phenyl, C1-6 alkyl substituted with up to 5 fluoro, and C1-6 alkoxy substituted with up to 5 fluoro, said phenyl optionally substituted with one or more substituents each independently selected from the group consisting of halo, C1-6 alkyl, —(CH2)uC3-7cycloalkyl, C2-6 alkenyl, C1-6 alkoxy, C1-6 alkyl substituted with up to 5 fluoro, and C1-6 alkoxy substituted with up to 5 fluoro.

In some embodiments, R4 is C1-6 alkyl, C3-7cycloalkyl, —OC3-7cycloalkyl, phenyl, C1-6 alkyl substituted with up to 5 fluoro, and C1-6 alkoxy substituted with up to 5 fluoro, said phenyl, optionally substituted with one or more substituents each independently selected from the group consisting of halo, C1-6 alkyl, C1-6 alkoxy, C1-6 alkyl substituted with up to 5 fluoro, and C1-6 alkoxy substituted with up to 5 fluoro.

In some embodiments, Y is NR8R9 and R8 and R2 come together to be C1-3 alkyl linking together as a ring.

In some embodiments, R2 is a hydrogen or C1-6 alkyl, C3-7 cycloalkyl, and phenyl, said C1-6 alkyl optionally substituted with one or more halo.

In some embodiments, R2 is a hydrogen.

In some embodiments, R9 is hydrogen, or C1-6 alkyl, optionally substituted with one or more substituents each independently selected from the group consisting of hydroxyl R19 or OR20;

R19 is phenyl optionally substituted with one or more substituents each independently selected from the group consisting of halo, cyano, C1-6 alkyl optionally substituted with up to 5 fluoro, and C1-6 alkoxy optionally substituted with up to 5 fluoro; and R20 is hydrogen or phenyl optionally substituted with one or more substituents each independently selected from the group consisting of halo, cyano, nitro, hydroxy, C1-6 alkyl optionally substituted with up to 5 fluoro, and C1-6 alkoxy optionally substituted with up to 5 fluoro.

In some embodiments, the compound of formula (I) is selected from the group consisting of:

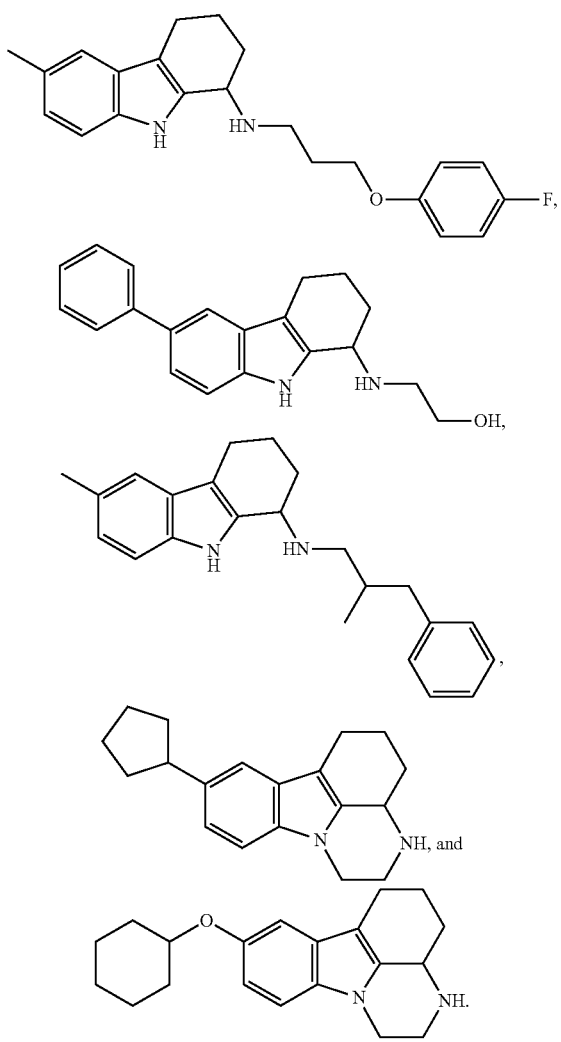

The term "ester" refers to a chemical moiety with formula —(R)$_n$—COOR', where R and R' are independently selected from the group consisting of alkyl, cycloalkyl, aryl, heteroaryl (bonded through a ring carbon) and heteroalicyclic (bonded through a ring carbon), and where n is 0 or 1.

An "amide" is a chemical moiety with formula —(R)$_n$—C(O)NHR' or —(R)$_n$—NHC(O)R', where R and R' are independently selected from the group consisting of alkyl, cycloalkyl, aryl, heteroaryl (bonded through a ring carbon) and heteroalicyclic (bonded through a ring carbon), and where n is 0 or 1. An amide may be an amino acid or a peptide molecule attached to a molecule of the present invention, thereby forming a prodrug.

Any amine, hydroxy, or carboxyl side chain on the compounds of the present invention can be esterified or amidified. The procedures and specific groups to be used to achieve this end are known to those of skill in the art and can readily be found in reference sources such as Greene and Wuts, Protective Groups in Organic Synthesis, 3$^{rd}$ Ed., John Wiley & Sons, New York, N.Y., 1999, which is incorporated herein in its entirety.

The terms "protecting group" and "protecting groups" as used herein refer to any atom or group of atoms that is added to a molecule in order to prevent existing groups in the molecule from undergoing unwanted chemical reactions. Examples of protecting group moieties are described in T. W. Greene and P. G. M. Wuts, Protective Groups in Organic Synthesis, 3. Ed. John Wiley & Sons, 1999, and in J. F. W. McOmie, Protective Groups in Organic Chemistry Plenum Press, 1973, both of which are hereby incorporated by reference. The protecting group moiety may be chosen in such a way, that they are stable to the reaction conditions applied and readily removed at a convenient stage using methodology known from the art. A non-limiting list of protecting groups include benzyl; substituted benzyl; alkylcarbonyls (e.g., t-butoxycarbonyl (BOC)); arylalkylcarbonyls (e.g., benzyloxycarbonyl, benzoyl); substituted methyl ether (e.g. methoxymethyl ether); substituted ethyl ether; a substituted benzyl ether; tetrahydropyranyl ether; silyl ethers (e.g., trimethylsilyl, triethylsilyl, triisopropylsilyl, t-butyldimethylsilyl, or t-butyldiphenylsilyl); esters (e.g. benzoate ester); carbonates (e.g. methoxymethylcarbonate); sulfonates (e.g. tosylate, mesylate); acyclic ketal (e.g. dimethyl acetal); cyclic ketals (e.g., 1,3-dioxane or 1,3-dioxolanes); acyclic acetal; cyclic acetal; acyclic hemiacetal; cyclic hemiacetal; and cyclic dithioketals (e.g., 1,3-dithiane or 1,3-dithiolane).

A "prodrug" refers to an agent that is converted into the parent drug in vivo. Prodrugs are often useful because, in some situations, they may be easier to administer than the parent drug. They may, for instance, be bioavailable by oral administration whereas the parent is not. The prodrug may also have improved solubility in pharmaceutical compositions over the parent drug. An example, without limitation, of a prodrug would be a compound of the present invention which is administered as an ester (the "prodrug") to facilitate transmittal across a cell membrane where water solubility is detrimental to mobility but which then is metabolically hydrolyzed to the carboxylic acid, the active entity, once inside the cell where water-solubility is beneficial. A further example of a prodrug might be a short peptide (polyaminoacid) bonded to an acid group where the peptide is metabolized to reveal the active moiety.

The term "aromatic" refers to an aromatic group which has at least one ring having a conjugated pi electron system and includes both carbocyclic aryl (e.g., phenyl) and heterocyclic aryl groups (e.g., pyridine). The term includes monocyclic or fused-ring polycyclic (i.e., rings which share adjacent pairs of carbon atoms) groups. The term "carbocyclic" refers to a compound which contains one or more covalently closed ring structures, and that the atoms forming the backbone of the ring are all carbon atoms. The term thus distinguishes carbocyclic from heterocyclic rings in which the ring backbone contains at least one atom which is different from carbon. The term "heteroaromatic" refers to an aromatic group which contains at least one heterocyclic ring.

As used herein, the term "alkyl" refers to an aliphatic hydrocarbon group. The alkyl moiety may be a "saturated alkyl" group, which means that it does not contain any alkene or alkyne moieties. The alkyl moiety may also be an "unsaturated alkyl" moiety, which means that it contains at least one alkene or alkyne moiety. An "alkene" moiety refers to a group consisting of at least two carbon atoms and at least one carbon-carbon double bond, and an "alkyne" moiety refers to a group consisting of at least two carbon atoms and at least one carbon-carbon triple bond. The alkyl moiety, whether saturated or unsaturated, may be branched, straight chain, or cyclic.

The alkyl group may have 1 to 20 carbon atoms (whenever it appears herein, a numerical range such as "1 to 20" refers to each integer in the given range; e.g., "1 to 20 carbon atoms" means that the alkyl group may consist of 1 carbon atom, 2 carbon atoms, 3 carbon atoms, etc., up to and including 20 carbon atoms, although the present definition also covers the occurrence of the term "alkyl" where no numerical range is designated). The alkyl group may also be a medium size alkyl having 1 to 10 carbon atoms. The alkyl group could also be a lower alkyl having 1 to 5 carbon atoms. The alkyl group of the compounds of the invention may be designated as "$C_1$-$C_4$ alkyl" or similar designations. By way of example only, "$C_1$-$C_4$ alkyl" indicates that there are one to four carbon atoms in the alkyl chain, i.e., the alkyl chain is selected from the group consisting of methyl, ethyl, propyl, iso-propyl, n-butyl, iso-butyl, sec-butyl, and t-butyl.

The alkyl group may be substituted or unsubstituted. When substituted, the substituent group(s) is(are) one or more group(s) individually and independently selected from cycloalkyl, aryl, heteroaryl, heteroalicyclic, hydroxy, alkoxy, aryloxy, mercapto, alkylthio, arylthio, cyano, halo, carbonyl, thiocarbonyl, O-carbamyl, N-carbamyl, O-thiocarbamyl, N-thiocarbamyl, C-amido, N-amido, S-sulfonamido, N-sulfonamido, C-carboxy, O-carboxy, isocyanato, thiocyanato, isothiocyanato, nitro, silyl, trihalomethanesulfonyl, and amino, including mono- and di-substituted amino groups, and the protected derivatives thereof. Typical alkyl groups include, but are in no way limited to, methyl, ethyl, propyl, isopropyl, butyl, isobutyl, tertiary butyl, pentyl, hexyl, ethenyl, propenyl, butenyl, cyclopropyl, cyclobutyl, cyclopentyl, cyclohexyl, and the like. Wherever a substituent is described as being "optionally substituted" that substitutent may be substituted with one of the above substituents.

The substituent "R" appearing by itself and without a number designation refers to a substituent selected from the group consisting of hydrogen, alkyl, cycloalkyl, aryl, heteroaryl (bonded through a ring carbon) and heteroalicyclic (bonded through a ring carbon).

An "O-carboxy" group refers to a RC(=O)O— group, where R is as defined herein.

A "C-carboxy" group refers to a —C(=O)OR groups where R is as defined herein.

An "acetyl" group refers to a —C(=O)CH$_3$, group.

A "trihalomethanesulfonyl" group refers to a X$_3$CS(=O)$_2$— group where X is a halogen.

A "cyano" group refers to a —CN group.

An "isocyanato" group refers to a —NCO group.

A "thiocyanato" group refers to a —CNS group.

An "isothiocyanato" group refers to a —NCS group.

A "sulfinyl" group refers to a —S(=O)—R group, with R as defined herein.

A "S-sulfonamido" group refers to a —S(=O)$_2$NR, group, with R as defined herein.

A "N-sulfonamido" group refers to a RS(=O)$_2$NH— group with R as defined herein.

A "trihalomethanesulfonamido" group refers to a X$_3$CS(=O)$_2$NR-group with X and R as defined herein.

An "O-carbamyl" group refers to a —OC(=O)—N(R)$_2$, group-with R as defined herein.

An "N-carbamyl" group refers to a ROC(=O)NH— group, with R as defined herein.

An "O-thiocarbamyl" group refers to a —OC(=S)—N(R)$_2$, group with R as defined herein.

An "N-thiocarbamyl" group refers to an ROC(=S)NH— group, with R as defined herein.

A "C-amido" group refers to a —C(=O)—N(R)$_2$ group with R as defined herein.

An "N-amido" group refers to a RC(=O)NH— group, with R as defined herein.

The term "perhaloalkyl" refers to an alkyl group where all of the hydrogen atoms are replaced by halogen atoms.

The term "acylalkyl" refers to a RC(=O)R'— group, with R as defined herein, and R' being a diradical alkylene group. Examples of acylalkyl, without limitation, may include CH$_3$C(=O)CH$_2$—, CH$_3$C(=O)CH$_2$CH$_2$—, CH$_3$CH$_2$C(=O)CH$_2$CH$_2$—, CH$_3$C(=O)CH$_2$CH$_2$CH$_2$—, and the like.

Unless otherwise indicated, when a substituent is deemed to be "optionally substituted," it is meant that the substitutent is a group that may be substituted with one or more group(s) individually and independently selected from cycloalkyl, aryl, heteroaryl, heteroalicyclic, hydroxy, alkoxy, aryloxy, mercapto, alkylthio, arylthio, cyano, halo, carbonyl, thiocarbonyl, O-carbamyl, N-carbamyl, O-thiocarbamyl, N-thiocarbamyl, C-amido, N-amido, S-sulfonamido, N-sulfonamido, C-carboxy, O-carboxy, isocyanato, thiocyanato, isothiocyanato, nitro, silyl, trihalomethanesulfonyl, and amino, including mono- and di-substituted amino groups, and the protected derivatives thereof. The protecting groups that may form the protective derivatives of the above substituents are known to those of skill in the art and may be found in references such as Greene and Wuts, above.

In the present context, the term "cycloalkyl" is intended to cover three-, four-, five-, six-, seven-, and eight- or more membered rings comprising carbon atoms only. A cycloalkyl can optionally contain one or more unsaturated bonds situated in such a way, however, that an aromatic pi-electron system does not arise. Some examples of "cycloalkyl" are the carbocycles cyclopropane, cyclobutane, cyclopentane, cyclopentene, cyclopentadiene, cyclohexane, cyclohexene, 1,3-cyclohexadiene, 1,4-cyclohexadiene, cycloheptane, or cycloheptene.

As used herein, "heterocyclyl" means a cyclic ring system comprising at least one heteroatom in the ring system backbone. The heteroatoms are independently selected from oxygen, sulfur, and nitrogen. Heterocyclyls may include multiple fused rings. Heterocyclyls may have any degree of saturation provided that at least one ring in the ring system is not aromatic. Heterocyclyls may be substituted or unsubstituted, and are attached to other groups via any available valence, preferably any available carbon or nitrogen. Preferred monocyclic heterocycles are of 5 or 6 members. In six membered monocyclic heterocycles, the heteroatom(s) are selected from one up to three of oxygen, sulfur, and nitrogen, and wherein when the heterocycle is five membered, preferably it has one or two heteroatoms selected from oxygen, sulfur, and nitrogen.

A heterocyclyl can further contain one or more carbonyl or thiocarbonyl functionalities, so as to make the definition include oxo-systems and thio-systems such as lactams, lactones, cyclic imides, cyclic thioimides, cyclic carbamates, and the like.

Some examples of "heterocyclyls" include, but are not limited to, tetrahydrothiopyran, 4H-pyran, tetrahydropyran, piperidine, 1,3-dioxin, 1,3-dioxane, 1,4-dioxin, 1,4-dioxane, piperazine, 1,3-oxathiane, 1,4-oxathiin, 1,4-oxathiane, tetrahydro-1,4-thiazine, 2H-1,2-oxazine, maleimide, succinimide, barbituric acid, thiobarbituric acid, dioxopiperazine, hydantoin, dihydrouracil, morpholine, trioxane, hexahydro-1,3,5-triazine, tetrahydrothiophene, tetrahydrofuran, pyrroline, pyrrolidine, pyrrolidone, pyrrolidione, pyrazoline, pyrazolidine, imidazoline, imidazolidine, 1,3-dioxole, 1,3-dioxolane, 1,3-dithiole, 1,3-dithiolane, isoxazoline, isoxazolidine, oxazoline, oxazolidine, oxazolidinone, thiazoline, thiazolidine, and 1,3-oxathiolane. The attachment point of a heterocycle radical can be at the position of a nitrogen heteroatom or via a carbon atom of the heterocycle.

In the present context the term "aryl" is intended to mean a carbocyclic aromatic ring or ring system. Moreover, the term "aryl" includes fused ring systems wherein at least two aryl rings, or at least one aryl and at least one C3-8-cycloalkyl share at least one chemical bond. Some examples of "aryl" rings include optionally substituted phenyl, naphthalenyl, phenanthrenyl, anthracenyl, tetralinyl, fluorenyl, indenyl, and indanyl. The term "aryl" relates to aromatic, including, for example, benzenoid groups, connected via one of the ring-forming carbon atoms, and optionally carrying one or more substituents selected from heterocyclyl, heteroaryl, halo, hydroxy, amino, cyano, nitro, alkylamido, acyl, $C_{1-6}$ alkoxy, $C_{1-6}$ alkyl, $C_{1-6}$ hydroxyalkyl, $C_{1-6}$ aminoalkyl, $C_{1-6}$ alkylamino, alkylsulfenyl, alkylsulfinyl, alkylsulfonyl, sulfamoyl, or trifluoromethyl. The aryl group can be substituted at the para and/or meta positions. In other embodiments, the aryl group can be substituted at the ortho position. Representative examples of aryl groups include, but are not limited to, phenyl, 3-halophenyl, 4-halophenyl, 3-hydroxyphenyl, 4-hydroxyphenyl, 3-aminophenyl, 4-aminophenyl, 3-methylphenyl, 4-methylphenyl, 3-methoxyphenyl, 4-methoxyphenyl, 4-trifluoromethoxyphenyl 3-cyanophenyl, 4-cyanophenyl, dimethylphenyl, naphthyl, hydroxynaphthyl, hydroxymethylphenyl, trifluoromethylphenyl, alkoxyphenyl, 4-morpholin-4-yl-phenyl, 4-pyrrolidin-1-ylphenyl, 4-pyrazolylphenyl, 4-triazolylphenyl, and 4-(2-oxopyrrolidin-1-yl)phenyl.

As used herein, the term "heteroaryl" means an aromatic radical having one or more heteroatom(s) (e.g., oxygen, sulfur, or nitrogen) in the ring backbone and may include a single ring (e.g., pyridine) or multiple condensed rings (e.g., quinoline). Heteroaryl groups can carry one or more substituents, each independently selected from halo, hydroxy, amino, cyano, nitro, cycloalkyl, haloalkyl, aryl, heterocyclyl, mercapto, alkylamido, acyl, $C_{1-6}$-alkoxy, $C_{1-6}$-alkyl, $C_{1-6}$-hydroxyalkyl, $C_{1-6}$-aminoalkyl, $C_{1-6}$-alkylamino, alkylsulfenyl, alkylsulfinyl, alkylsulfonyl, sulfamoyl, and trifluoromethyl. Representative examples of heteroaryl groups include, but are not limited to, optionally substituted derivatives of furan, benzofuran, thiophene, benzothiophene, pyrrole, pyridine, indole, oxazole, benzoxazole, isoxazole, benzisoxazole, thiazole, benzothiazole, isothiazole, imidazole, benzimidazole, pyrazole, indazole, tetrazole, quionoline, isoquinoline, pyridazine, pyrimidine, purine and pyrazine, furazan, 1,2,3-oxadiazole, 1,2,3-thiadiazole, 1,2,4-thiadiazole, triazole, benzotriazole, pteridine, phenoxazole, oxadiazole, benzopyrazole, quinolizine, cinnoline, phthalazine, quinazoline, and quinoxaline. In some embodiments, the substituents can be halo, hydroxy, cyano, O—$C_{1-6}$-alkyl, $C_{1-6}$-alkyl, hydroxy-$C_{1-6}$-alkyl, and amino-$C_{1-6}$-alkyl.

Antisense Molecules

In some embodiments, the Cdc42-specific inhibitor can be an antisense molecule. The term "antisense" (AS) or "antisense fragment" refers to a polynucleotide fragment (comprising either deoxyribonucleotides, ribonucleotides or a mixture of both) having inhibitory antisense activity, which causes a decrease in the expression of the endogenous genomic copy of the corresponding gene. An AS polynucleotide refers to a polynucleotide which comprises consecutive nucleotides having a sequence of sufficient length and homology to a sequence present within the sequence of the target gene to permit hybridization of the AS to the gene. Many reviews have covered the main aspects of antisense (AS) technology and its enormous therapeutic potential (see, for example, Aboul-Fadl T., Curr Med. Chem. 2005; 12(19): 2193-214; Crooke S T, Curr Mol. Med. 2004 August; 4(5): 465-87; Crooke S T, Annu Rev Med. 2004; 55:61-95; Vacek M et al., Cell Mol Life Sci. 2003 May; 60(5):825-33; Cho-Chung Y S, Arch Pharm Res. 2003 March; 26(3):183-91; Moreira J N et al., Rev Recent Clin Trials 2006 September; 1(3):217-35). There are further reviews on the chemical (Crooke, 1995; Uhlmann et al, 1990), cellular (Wagner, 1994) and therapeutic (Hanania, et al, 1995; Scanlon, et al, 1995; Gewirtz, 1993) aspects of this technology. Antisense intervention in the expression of specific genes can be achieved by the use of synthetic AS oligonucleotide sequences (see, e.g., Lefebvre-d'Hellencourt et al, 1995; Agrawal, 1996; LevLehman et al, 1997).

AS oligonucleotide sequences may be short sequences of DNA, typically a 15-mer to a 30-mer but may be as small as a 7-mer (Wagner et al, 1996), designed to complement a target mRNA of interest and form an RNA:AS duplex. This duplex formation can prevent processing, splicing, transport or translation of the relevant mRNA. Moreover, certain AS nucleotide sequences can elicit cellular RNase H activity when hybridized with their target mRNA, resulting in mRNA degradation (Calabretta et al, 1996 Semin Oncol. 23(1):78-87). In that case, RNase H will cleave the RNA component of the duplex and can potentially release the AS to further hybridize with additional molecules of the target RNA. An additional mode of action results from the interaction of AS with genomic DNA to form a triple helix, which can be transcriptionally inactive.

The sequence target segment for the antisense oligonucleotide is selected such that the sequence exhibits suitable energy related characteristics important for oligonucleotide duplex formation with their complementary templates, and shows a low potential for self-dimerization or self-complementation (Anazodo et al., 1996). For example, the computer program OLIGO® (Primer Analysis Software, Version 3.4), can be used to determine antisense sequence melting temperature, free energy properties, and to estimate potential self-dimer formation and self-complimentary properties. The program allows the determination of a qualitative estimation of these two parameters (potential self-dimer formation and self-complimentary) and provides an indication of "no potential" or "some potential" or "essentially complete potential". Using this program target segments are generally selected that have estimates of no potential in these parameters. However, segments can be used that have "some potential" in one of the categories. A balance of the parameters is used in the selection as is known in the art. Further, the oligonucleotides are also selected as needed so that analogue substitutions do not substantially affect function.

Phosphorothioate antisense oligonucleotides do not normally show significant toxicity at concentrations that are effective and exhibit sufficient pharmacodynamic half-lives in animals (Agarwal et al., 1996) and are nuclease resistant. Antisense induced loss-of-function phenotypes related with cellular development were shown for the glial fibrillary acidic protein (GFAP), for the establishment of tectal plate formation in chick (Galileo et al., 1991) and for the N-myc protein, responsible for the maintenance of cellular heterogeneity in neuroectodermal cultures (epithelial vs. neuroblastic cells, which differ in their colony forming abilities, tumorigenicity and adherence) (Rosolen et al., 1990; Whitesell et al, 1991). Antisense oligonucleotide inhibition of basic fibroblast growth factor (bFgF), having mitogenic and angiogenic properties, suppressed 80% of growth in glioma cells (Morrison, 1991) in a saturable and specific manner. Being hydrophobic, antisense oligonucleotides interact well with phospholipid membranes (Akhter et al., 1991). Following their interaction with the cellular plasma membrane, they are actively (or passively) transported into living cells (Loke et al., 1989), in a saturable mechanism predicted to involve specific receptors (Yakubov et al., 1989).

siRNA

In other embodiments, the Cdc42-specific inhibitor can be a "small interfering RNA" (siRNA). siRNA refers to an RNA molecule which decreases or silences (prevents) the expression of a gene/mRNA (e.g., Cdc42) of its endogenous cellular counterpart. The term is understood to encompass "RNA interference" (RNAi). RNA interference (RNAi) refers to the process of sequence-specific post transcriptional gene silencing in mammals mediated by small interfering RNAs (siRNAs, e.g., short hairpin RNAs (shRNAs)) (Fire et al, 1998, Nature 391, 806). The corresponding process in plants is commonly referred to as specific post transcriptional gene silencing or RNA silencing and is also referred to as quelling in fungi. The RNA interference response may feature an endonuclease complex containing an siRNA, commonly referred to as an RNA-induced silencing complex (RISC), which mediates cleavage of single-stranded RNA having sequence complementary to the antisense strand of the siRNA duplex. Cleavage of the target RNA may take place in the middle of the region complementary to the antisense strand of the siRNA duplex (Elbashir et al 2001, Genes Dev., 15, 188). For recent information on these terms and proposed mechanisms, see Bernstein E., Denli A M., Hannon G J: The rest is silence. RNA. 2001 November; 7(11):1509-21; and Nishikura K.: A short primer on RNAi: RNA-directed RNA polymerase acts as a key catalyst. Cell. 2001 November 16; 107 (4):415-8.

RNAi is an efficient method for the inactivation of genes (Nature Reviews, 2002, v. 3, p. 737-47; Nature, 2002, v. 418, p. 244-51). As a method, it is based on the ability of dsRNA species to enter a specific protein complex, where it is then targeted to the complementary cellular RNA and specifically degrades it. In more detail, dsRNAs are digested into short (17-29 bp) inhibitory RNAs (siRNAs) by type III RNAses (DICER, Drosha, etc) (Nature, 2001, v. 409, p. 363-6; Nature, 2003, 425, p. 415-9). These fragments and complementary mRNA are recognized by the specific RISC protein complex. The whole process is culminated by endonuclease cleavage of target mRNA (Nature Reviews, 2002, v. 3, p. 737-47; Curr Opin Mol. Ther. 2003 June; 5(3):217-24).

For disclosure on how to design and prepare siRNA to known genes see, for example, Chalk A M, Wahlestedt C, Sonnhammer E L. 2004 Jun. 18; 319(1):264-74; Sioud M, Leirdal M., Methods Mol. Biol. 2004; 252:457-69; Levenkova N, Gu Q, Rux J J. 2004 Feb. 12; 20(3):430-2; and Ui-Tei K, Naito Y, Takahashi F, Haraguchi T, Ohki-Hamazaki H, Juni A, Ueda R, Saigo K., Nucleic Acids Res. 2004 Feb. 9; 32(3): 936-48. See also PCT publications WO 2004/015107 (Atugen) and WO 02/44321 (Tuschl et al), and also Chiu Y L, Rana T M. RNA 2003 September; 9(9):1034-48 and U.S. Pat. Nos. 5,898,031 and 6,107,094 (Crooke) for production of modified/more stable siRNAs.

DNA-based vectors capable of generating siRNA within cells have been developed. The method generally involves transcription of short hairpin RNAs that are efficiently processed to form siRNAs within cells. (see, e.g., Paddison et al. PNAS 2002, 99:1443-1448; Paddison et al. Genes & Dev 2002, 16:948-958; Sui et al. PNAS 2002, 8:5515-5520; and Brummelkamp et al. Science 2002, 296:550-553). These reports describe methods to generate siRNAs capable of specifically targeting numerous endogenously and exogenously expressed genes.

For methods related to the delivery of siRNAs, see, for example, Shen et al (FEBS letters 539: 111-114 (2003)), Xia et al., Nature Biotechnology 20: 1006-1010 (2002), Reich et al., Molecular Vision 9: 210-216 (2003), Sørensen et al. (J. Mol. Biol. 327: 761-766 (2003), Lewis et al., Nature Genetics 32: 107-108 (2002) and Simeoni et al., Nucleic Acids Research 31, 11: 2717-2724 (2003). siRNA has recently been successfully used for inhibition in primates; for further details, see, for example, Tolentino et al., Retina 24(1) February 2004 pp 132-138.

In some embodiments the oligoribonucleotide according to embodiments disclosed herein comprises modified siRNA. In various embodiments the siRNA comprises an RNA duplex comprising a first strand and a second strand, whereby the first strand comprises a ribonucleotide sequence at least partially complementary to about 18 to about 40 consecutive nucleotides of a target nucleic acid, and the second strand comprises ribonucleotide sequence at least partially complementary to the first strand and wherein said first strand and/or said second strand comprises a plurality of groups of modified ribonucleotides having a modification at the 2'-position of the sugar moiety whereby within each strand each group of modified ribonucleotides is flanked on one or both sides by a group of flanking ribonucleotides whereby each ribonucleotide forming the group of flanking ribonucleotides is selected from an unmodified ribonucleotide or a ribonucleotide having a modification different from the modification of the groups of modified ribonucleotides.

Ribozymes

In some embodiments, the Cdc42-specific inhibitor can be a ribozyme. The term "ribozyme" refers to an RNA molecule that possesses RNA catalytic ability and cleaves a specific site in a target RNA. In accordance with the embodiments disclosed herein, ribozymes which cleave mRNA (e.g., Cdc42 mRNA) may be utilized as inhibitors. This may be necessary in cases where antisense therapy is limited by stoichiometric considerations (Sarver et al., 1990, Gene Regulation and Aids, pp. 305-325). Ribozymes can then be used that will target the a gene associated with a bone marrow disease. The number of RNA molecules that are cleaved by a ribozyme is greater than the number predicted by stochiochemistry. (Hampel and Tritz, 1989; Uhlenbeck, 1987).

Ribozymes catalyze the phosphodiester bond cleavage of RNA. Several ribozyme structural families have been identified including Group I introns, RNase P, the hepatitis delta virus ribozyme, hammerhead ribozymes and the hairpin ribozyme originally derived from the negative strand of the tobacco ringspot virus satellite RNA (sTRSV) (Sullivan, 1994; U.S. Pat. No. 5,225,347). The latter two families are derived from viroids and virusoids, in which the ribozyme is believed to separate monomers from oligomers created during rolling circle replication (Symons, 1989 and 1992). Hammerhead and hairpin ribozyme motifs are most commonly adapted for trans-cleavage of mRNAs for gene therapy (Sullivan, 1994). In general the ribozyme has a length of from about 30-100 nucleotides. Delivery of ribozymes is similar to that of AS fragments and/or siRNA molecules.

The term "nucleic acids", as used herein, may be DNA or RNA or modified versions thereof. Nucleic acids may also include modified nucleotides that permit correct read through by a polymerase and do not alter expression of a polypeptide encoded by that nucleic acid. The terms "nucleic acid" and "oligonucleotide" are used interchangeably to refer to a molecule comprising multiple nucleotides. As used herein, the terms refer to oligoribonucleotides as well as oligodeoxyribonucleotides. The terms shall also include polynucleosides (e.g., a polynucleotide minus the phosphate) and any other organic base containing polymer. Nucleic acids include vectors, e.g., plasmids, as well as oligonucleotides. Nucleic acid molecules can be obtained from existing nucleic acid sources, but are preferably synthetic (e.g., produced by oligonucleotide synthesis).

Polynucleotides to be used according to embodiments disclosed herein may undergo modifications so as to possess improved therapeutic properties. Modifications or analogs of nucleotides can be introduced to improve the therapeutic properties of polynucleotides. Improved properties include increased nuclease resistance and/or increased ability to permeate cell membranes. Nuclease resistance, where needed, is provided by any method known in the art that does not interfere with biological activity of the AS polynucleotide, siRNA, cDNA and/or ribozymes as needed for the method of use and delivery (Iyer et al., 1990; Eckstein, 1985; Spitzer and Eckstein, 1988; Woolf et al., 1990; Shaw et al., 1991). Modifications that can be made to oligonucleotides in order to enhance nuclease resistance include modifying the phosphorous or oxygen heteroatom in the phosphate backbone. These include preparing methyl phosphonates, phosphorothioates, phosphorodithioates and morpholino oligomers. In one embodiment it is provided by having phosphorothioate bonds linking between the four to six 3'-terminus nucleotide bases. Alternatively, phosphorothioate bonds link all the nucleotide bases. Other modifications known in the art may be used where the biological activity is retained, but the stability to nucleases is substantially increased.

All analogues of, or modifications to, a polynucleotide may be employed with the embodiments disclosed herein, provided that said analogue or modification does not substantially affect the function of the polynucleotide. The nucleotides can be selected from naturally occurring or synthetic modified bases. Naturally occurring bases include adenine, guanine, cytosine, thymine and uracil. Modified bases of nucleotides include inosine, xanthine, hypoxanthine, 2-aminoadenine, 6-methyl, 2-propyl and other alkyl adenines, 5-halo uracil, 5-halo cytosine, 6-aza cytosine and 6-aza thymine, psuedo uracil, 4-thiuracil, 8-halo adenine, 8-aminoadenine, 8-thiol adenine, 8-thiolalkyl adenines, 8-hydroxyl adenine and other 8-substituted adenines, 8-halo guanines, 8-amino guanine, 8-thiol guanine, 8-thioalkyl guanines, 8-hydroxyl guanine and other substituted guanines, other aza and deaza adenines, other aza and deaza guanines, 5-trifluoromethyl uracil and 5-trifluoro cytosine.

In addition, analogues of polynucleotides can be prepared wherein the structure of the nucleotide is fundamentally altered and that are better suited as therapeutic or experimental reagents. An example of a nucleotide analogue is a peptide nucleic acid (PNA) wherein the deoxyribose (or ribose) phosphate backbone in DNA (or RNA is replaced with a polyamide backbone which is similar to that found in peptides. PNA analogues have been shown to be resistant to degradation by enzymes and to have extended lives in vivo and in vitro. Further, PNAs have been shown to bind stronger to a complementary DNA sequence than a DNA molecule. This observation is attributed to the lack of charge repulsion between the PNA strand and the DNA strand. Other modifications that can be made to oligonucleotides include polymer backbones, cyclic backbones, or acyclic backbones, as well as LNA ("locked nucleic acid").

Embodiments disclosed herein also include nucleic acids (e.g., siRNA) that can have the following degrees of homology or identity to a Cdc42-specific inhibitory nucleic acid: 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99%. Candidate Cdc42-specific inhibitory nucleic acids having greater than or equal to 35% homology or identity can be identified by methods known in the art and can be subsequently examined using functional assays, for example, the assays described herein and those known in the art.

The term "homology" refers to the percent of identity between two polynucleotide or two polypeptide moieties. The correspondence between the sequence from one moiety to another can be determined by techniques known in the art. For example, homology can be determined by a direct comparison of the sequence information between two polynucleotide or polypeptide molecules by aligning the sequence information and using readily available computer programs. Alternatively, homology can be determined by hybridization of polynucleotides under conditions, which form stable duplexes between homologous regions, followed by digestion with single-stranded-specific nuclease(s), and size determination of the digested fragments. Two DNA, or two polypeptide sequences are "substantially homologous" to each other when at least about 80%, preferably at least about 90%, and most preferably at least about 95% of the nucleotides or amino acids match over a defined length of the molecules, as determined using the methods above.

Preparation of Peptides and Polypeptides

In some embodiments, the Cdc42-specific inhibitor can be a polypeptide (e.g., a dominant negative peptide, an antibody, or an affibody). Polypeptides may be produced, for example, via several methods known in the art (e.g., synthetically or via recombinant methods).

The terms "polypeptide," "peptide," and "protein" are used interchangeably herein to refer to a polymer of amino acid residues. The terms apply to amino acid polymers in which one or more amino acid residue is an analog or mimetic of a corresponding naturally occurring amino acid, as well as to naturally occurring amino acid polymers. Polypeptides can be modified, e.g., by the addition of carbohydrate residues to form glycoproteins. The terms "polypeptide," "peptide" and "protein" include glycoproteins, as well as non-glycoproteins. Polypeptide products can be biochemically synthesized such as by employing standard solid phase techniques. Such methods include but are not limited to exclusive solid phase synthesis, partial solid phase synthesis methods, fragment condensation, classical solution synthesis. These methods are preferably used when the peptide is relatively short (e.g., 10 kDa) and/or when it cannot be produced by recombinant techniques (e.g., not encoded by a nucleic acid sequence) and therefore involves different chemistry. Solid phase polypeptide synthesis procedures are well known in the art and further described by John Morrow Stewart and Janis Dillaha Young, Solid Phase Peptide Syntheses (2nd Ed., Pierce Chemical Company, 1984). Synthetic polypeptides can optionally be purified by preparative high performance liquid chromatography [Creighton T. (1983) Proteins, structures and molecular principles. WH Freeman and Co. N.Y.], after which their composition can be confirmed via amino acid sequencing. In cases where large amounts of a polypeptide are desired, it can be generated using recombinant techniques such as described by Bitter et al., (1987) Methods in Enzymol. 153:516-544, Studier et al. (1990) Methods in Enzymol. 185:60-89, Brisson et al. (1984) Nature 310:511-514, Takamatsu et al. (1987) EMBO J. 6:307-311, Coruzzi et al. (1984) EMBO J. 3:1671-1680 and Brogli et al., (1984) Science 224:838-843, Gurley et al. (1986) Mol. Cell. Biol. 6:559-565 and Weissbach & Weissbach, 1988, Methods for Plant Molecular Biology, Academic Press, NY, Section VIII, pp 421-463.

In some embodiments, the method of making the polypeptides or fragments thereof is to clone a polynucleotide comprising the cDNA of the gene into an expression vector and culture the cell harboring the vector so as to express the encoded polypeptide, and then purify the resulting polypeptide, all performed using methods known in the art as described in, for example, Marshak et al., "Strategies for Protein Purification and Characterization. A laboratory course manual." CSHL Press (1996). (in addition, see, e.g., Bibl Haematol. 1965; 23:1165-74 Appl Microbiol. 1967 July; 15(4):851-6; Can J. Biochem. 1968 May; 46(5):441-4; Biochemistry. 1968 July; 7(7):2574-80; Arch Biochem Biophys. 1968 Sep. 10; 126(3):746-72; Biochem Biophys Res Commun. 1970 Feb. 20; 38(4):825-30).).

The expression vector can include a promoter for controlling transcription of the heterologous material and can be either a constitutive or inducible promoter to allow selective transcription. Enhancers that can be required to obtain necessary transcription levels can optionally be included. The expression vehicle can also include a selection gene.

Vectors can be introduced into cells or tissues by any one of a variety of methods known within the art. Such methods can be found generally described in Sambrook et al., Molecular Cloning: A Laboratory Manual, Cold Springs Harbor Laboratory, New York (1989, 1992), in Ausubel et al., Current Protocols in Molecular Biology, John Wiley and Sons, Baltimore, Md. (1989), Vega et al., Gene Targeting, CRC Press, Ann Arbor, Mich. (1995), Vectors: A Survey of Molecular Cloning Vectors and Their Uses, Butterworths, Boston Mass. (1988) and Gilboa et al. (1986).

Preparation of Anti-Cdc42 Antibodies

Antibodies that bind to Cdc42 or a fragment derived therefrom may be prepared using an intact polypeptide or fragments containing smaller polypeptides as the immunizing antigen. For example, it may be desirable to produce antibodies that specifically bind to the N- or C-terminal or any other suitable domains of Cdc42. The polypeptide used to immunize an animal can be derived from translated cDNA or chemical synthesis and can be conjugated to a carrier protein, if desired. Such commonly used carriers which are chemically coupled to the polypeptide include keyhole limpet hemocyanin (KLH), thyroglobulin, bovine serum albumin (BSA) and tetanus toxoid. The coupled polypeptide is then used to immunize the animal.

If desired, polyclonal or monoclonal antibodies can be further purified, for example by binding to and elution from a matrix to which the polypeptide or a peptide to which the antibodies were raised is bound. Those skilled in the art know various techniques common in immunology for purification and/or concentration of polyclonal as well as monoclonal antibodies (Coligan et al, Unit 9, Current Protocols in Immunology, Wiley Interscience, 1994).

Methods for making antibodies of all types, including fragments, are known in the art (See for example, Harlow and Lane, Antibodies: A Laboratory Manual, Cold Spring Harbor Laboratory, New York (1988)). Methods of immunization, including all necessary steps of preparing the immunogen in a suitable adjuvant, determining antibody binding, isolation of antibodies, methods for obtaining monoclonal antibodies, and humanization of monoclonal antibodies are all known to the skilled artisan The antibodies may be humanized antibodies or human antibodies. Antibodies can be humanized using a variety of techniques known in the art including CDR-grafting (EP239, 400: PCT publication WO0.91/09967; U.S. Pat. Nos. 5,225, 539; 5,530,101; and 5,585,089, veneering or resurfacing (EP 592,106; EP 519,596; Padlan, Molecular Immunology 28(4/5):489-498 (1991); Studnicka et al., Protein Engineering 7(6):805-814 (1994); Roguska et al., PNAS 91:969-973 (1994)), and chain shuffling (U.S. Pat. No. 5,565,332).

The monoclonal antibodies as defined include antibodies derived from one species (such as murine, rabbit, goat, rat, human, etc.) as well as antibodies derived from two (or more) species, such as chimeric and humanized antibodies.

Completely human antibodies are particularly desirable for therapeutic treatment of human patients. Human antibodies can be made by a variety of methods known in the art including phage display methods using antibody libraries derived from human immunoglobulin sequences. See also U.S. Pat. Nos. 4,444,887 and 4,716,111; and PCT publications WO 98/46645, WO 98/50433, WO 98/24893, WO 98/16654, WO 96/34096, WO 96/33735, and WO 91/10741, each of which is incorporated herein by reference in its entirety.

Additional information regarding all types of antibodies, including humanized antibodies, human antibodies and antibody fragments can be found in WO 01/05998, which is incorporated herein by reference in its entirety.

Neutralizing antibodies can be prepared by the methods discussed above, possibly with an additional step of screening for neutralizing activity by, for example, a survival assay.

Embodiments disclosed herein also relate to the preparation and use of affibodies, binding proteins of non-Ig origin developed by combinatorial protein engineering principles, as described, for example, in Nygren PA 2008 FEBS Journal 275:2668-2676.

The polypeptides employed in embodiments disclosed herein may also be modified, optionally chemically modified, in order to improve their therapeutic activity. "Chemically modified"—when referring to the polypeptides, refers to a polypeptide where at least one of its amino acid residues is modified either by natural processes, such as processing or other post-translational modifications, or by chemical modification techniques which are well known in the art. Among the numerous known modifications typical, but not exclusive examples include: acetylation, acylation, amidation, ADP-ribosylation, glycosylation, GPI anchor formation, covalent attachment of a lipid or lipid derivative, methylation, myristylation, pegylation, prenylation, phosphorylation, ubiquitination, or any similar process.

Additional possible polypeptide modifications (such as those resulting from nucleic acid sequence alteration) include substitutions, deletions, and insertions.

A "conservative substitution" refers to the substitution of an amino acid in one class by an amino acid of the same class, where a class is defined by common physicochemical amino acid side chain properties and high substitution frequencies in homologous polypeptides found in nature, as determined, for example, by a standard Dayhoff frequency exchange matrix or BLOSUM matrix.

A "non-conservative substitution" refers to the substitution of an amino acid in one class with an amino acid from another class; for example, substitution of an Ala, a class II residue, with a class III residue such as Asp, Asn, Glu, or Gln.

A "deletion" refers to a change in either nucleotide or amino acid sequence in which one or more nucleotides or amino acid residues, respectively, are absent.

An "insertion" or "addition" refers to a change in a nucleotide or amino acid sequence which has resulted in the addition of one or more nucleotides or amino acid residues, respectively, as compared to the naturally occurring sequence.

A "substitution" refers to the replacement of one or more nucleotides or amino acids by different nucleotides or amino acids, respectively. As regards amino acid sequences the substitution may be conservative or non-conservative.

Embodiments disclosed herein also include polypeptides (e.g., dominant negative polypeptides or antibodies) that can have the following degrees of homology or identity to a Cdc42-specific inhibitory polypeptide: 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99%. Candidate Cdc42-specific inhibitory polypeptides having greater than or equal to 35% homology or identity can be identified by methods known in the art and can be subsequently examined using functional assays, for example, the assays described herein and those known in the art.

Methods for Mobilization and Treatments

Methods are provided to induce mobilization of peripheral blood precursor cells, to elevate circulating levels of peripheral blood precursor cells, or to enhance or facilitate hematopoietic reconstitution or engraftment, in mammals, including humans. "Peripheral blood precursor cells", as used herein, include stem cells, that are pluripotent, and early progenitor cells, that are more differentiated than stem cells. In some embodiments, mobilization of peripheral blood precursor cells in a mammal can be induced by administering to the mammal an effective amount of an active compound (e.g., a Cdc42-specific inhibitor, such as CASIN).

The method of mobilizing progenitor cells can be used for mobilization of stem/progenitor cells in patients who will undergo cytoreductive therapy, such as chemotherapy or radiation therapy. After mobilization, the stem/progenitor cells are collected from the peripheral blood and either stored, or expanded in culture. The method of mobilizing progenitor cells can also be used for mobilization of stem/progenitor cells in individuals who will serve as allogenic donors of progenitor cells. Other diseases and disorders for which the active compound is beneficial in addition to those already described are leukopenia of various origins including, congenital leukopenia, childhood or adult cyclic neutropenia, post-infective neutropenia, and myelodysplastic syndrome. In addition, the active compound can be used for patients who are "difficult to mobilize" because, for example, they are not sensitive to growth factors. The methods can further be used to cause tolerance of a recipient for organ transplantation.

The method of mobilizing progenitor cells can also be used in cancer therapy methods and in methods for inhibiting, ameliorating, or ablation of cancer cells and/or tumors. For example, like normal HSCs, their malignant counterpart, leukemia initiating cells (LICs) reside in their BM niches that provide the structural and physiological conditions supporting their survival and growth. LICs are resistant to traditional cancer therapy (e.g., chemotherapy) by interacting with their BM microenvironment, which can be the culprits of leukemia relapses after a period of remission induced by a cancer therapy (e.g., chemotherapy). Detachment of LICs from their niche by inducing mobilization of LICs (e.g., by administering a Cdc42-specific inhibitor) can be a used in combination with traditional cancer therapies (e.g., chemotherapy or radiotherapy) to provide more effective or improved cancer therapy methods and methods for inhibiting, ameliorating, or ablation of cancer cells and/or tumors.

The methods can additionally be used for gene therapy. Because pluripotent stem cells are self-renewing, and give rise to cell progenitors as well as mature blood cells, the stem cells are an appropriate target for gene therapy. After mobilization, stem/progenitor cells can be collected. The stem/progenitor cells can be modified to deliver gene products upon reintroduction to the individual. After modification, the cells are reinfused into the affected individual.

In some contexts, the terms "ameliorating," "treating," "treatment," "therapeutic," or "therapy" do not necessarily mean total cure or abolition of the disease or condition. Any alleviation of any undesired signs or symptoms of a disease or condition, to any extent, can be considered amelioration, and in some respects a treatment and/or therapy.

As used herein, the term "progenitor cells" refers to cells that, in response to certain stimuli, can form differentiated hematopoietic or myeloid cells. The presence of progenitor cells can be assessed by the ability of the cells in a sample to form colony-forming units of various types, including, for example, CFU-GM (colony-forming units, granulocyte-macrophage); CFU-GEMM (colony-forming units, multipotential); BFU-E (burst-forming units, erythroid); HPP-CFC (high proliferative potential colony-forming cells); or other types of differentiated colonies that can be obtained in culture using known protocols. As used herein, "stem" cells are less differentiated forms of progenitor cells. Typically, such cells are often positive for CD34 in humans. Some stem cells do not contain this marker, however.

Typical conditions that can be ameliorated or otherwise benefited by the treatment methods herein include, but are not limited to, hematopoietic disorders, such as aplastic anemia, Fanconi anemia, leukemias, drug-induced anemias, and hematopoietic deficits from chemotherapy or radiation therapy. The methods are also useful in enhancing the success of transplantation during and following immunosuppressive treatments as well as in effecting more efficient wound healing and treatment of bacterial inflammation. The methods are also useful for treating subjects who are immunocompromised or whose immune system is otherwise impaired. Typical conditions that are ameliorated or otherwise benefited by the method of the present invention, include retrovirus infections and more specifically human immunodeficiency virus (HIV) infections. The methods thus target a broad spectrum of conditions for which elevation of progenitor cells and/or stem cells in a subject would be beneficial or, where harvesting of progenitor cells and/or stem cell for subsequent stem cell transplantation would be beneficial. The compounds can also be administered to regenerate myocardium by mobilizing bone marrow stem cells.

The compounds of preferred embodiments can be used in relation to disorders arising from bone marrow cells. In normal bone marrow, the myelocytic series (polymorphoneuclear cells) make up approximately 60% of the cellular elements, and the erythrocytic series, 20-30%. Lymphocytes, monocytes, reticular cells, plasma cells and megakaryocytes together constitute 10-20%. Lymphocytes make up 5-15% of normal adult marrow. In the bone marrow, cell types are add mixed so that precursors of red blood cells (erythroblasts), macrophages (monoblasts), platelets (megakaryocytes), polymorphoneuclear leukocytes (myeloblasts), and lymphocytes (lymphoblasts) can be visible in one microscopic field. In addition, stem cells exist for the different cell lineages, as well as a precursor stem cell for the committed progenitor cells of the different lineages. The various types of cells and stages of each are known to the person of ordinary skill in the art and are found, for example, in *Immunology, Immunopathology and Immunity*, Fifth Edition, Sell et al. Simon and Schuster (1996), which is incorporated herein by reference in its entirety. Accordingly, the preferred embodiments are directed to disorders arising from these cells. These disorders include but are not limited to the following: diseases involving hematopoietic stem cells; committed lymphoid progenitor cells; lymphoid cells including B and T-cells; committed myeloid progenitors, including monocytes, granulocytes, and megakaryocytes; and committed erythroid progenitors.

These include but are not limited to the leukemias, including B-lymphoid leukemias, T-lymphoid leukemias, undifferentiated leukemias; erythroleukemia, megakaryoblastic leukemia, monocytic; [leukemias are encompassed with and without differentiation]; chronic and acute lymphoblastic leukemia, chronic and acute lymphocytic leukemia, chronic and acute myelogenous leukemia, lymphoma, myelo dysplastic syndrome, chronic and acute myeloid leukemia, myelomonocytic leukemia; chronic and acute myeloblastic leukemia, chronic and acute myelogenous leukemia, chronic and acute promyelocytic leukemia, chronic and acute myelocytic leukemia, hematologic malignancies of monocyte-macrophage lineage, such as juvenile chronic myelogenous leukemia; secondary AML, antecedent hematological disorder; refractory anemia; aplastic anemia; Fanconi anemia; reactive cutaneous angioendotheliomatosis; fibrosing disorders involving altered expression in dendritic cells, disorders including systemic sclerosis, E-M syndrome, epidemic toxic oil syndrome, eosinophilic fasciitis localized forms of scleroderma, keloid, and fibrosing colonopathy; angiomatoid malignant fibrous histiocytoma; carcinoma, including primary head and neck squamous cell carcinoma; sarcoma, including kaposi's sarcoma; fibroadenoma and phyllodes tumors, including mammary fibroadenoma; stromal tumors; phyllodes tumors, including histiocytoma; erythroblastosis; neurofibromatosis; diseases of the vascular endothelium; demyelinating, particularly in old lesions; gliosis, vasogenic edema, vascular disease, Alzheimer's and Parkinson's disease; T-cell lymphomas; B-cell lymphomas.

The preferred embodiments relate to methods of treatment of disorders involving T-cells include, but are not limited to, cell-mediated hypersensitivity, such as delayed type hypersensitivity and T-cell-mediated cytotoxicity, and transplant rejection; autoimmune diseases, such as systemic lupus erythematosus, Sjogren syndrome, systemic sclerosis, inflammatory myopathies, mixed connective tissue disease, and polyarteritis nodosa and other vasculitides; immunologic deficiency syndromes, including but not limited to, primary immunodeficiencies, such as thymic hypoplasia, severe combined immunodeficiency diseases, and AIDS; leukopenia; reactive (inflammatory) proliferations of white cells, including but not limited to, leukocytosis, acute nonspecific lymphadenitis, and chronic nonspecific lymphadenitis; neoplastic proliferations of white cells, including but not limited to lymphoid neoplasms, such as precursor T-cell neoplasms, such as acute lymphoblastic leukemia/lymphoma, peripheral T-cell and natural killer cell neoplasms that include peripheral T-cell lymphoma, unspecified, adult T-cell leukemia/lymphoma, mycosis fungoides and Szary syndrome, and Hodgkin disease.

The compounds of preferred embodiments can be used in relation to diseases of the skin. Diseases of the skin, include but are not limited to, disorders of pigmentation and melanocytes, including but not limited to, vitiligo, freckle, melasma, lentigo, nevocellular nevus, dysplastic nevi, and malignant melanoma; benign epithelial tumors, including but not limited to, seborrheic keratoses, acanthosis nigricans, fibroepithelial polyp, epithelial cyst, keratoacanthoma, and adnexal (appendage) tumors; premalignant and malignant epidermal tumors, including but not limited to, actinic keratosis, squamous cell carcinoma, basal cell carcinoma, and merkel cell carcinoma, tumors of the dermis, including but not limited to, benign fibrous histiocytoma, dermatofibrosarcoma protuberans, xanthomas, and dermal vascular tumors; tumors of cellular immigrants to the skin, including but not limited to, histiocytosis X, mycosis fungoides (cutaneous T-cell lymphoma), and mastocytosis; disorders of epidermal maturation, including but not limited to, ichthyosis; acute inflammatory dermatoses, including but not limited to, urticaria, acute eczematous dermatitis, and erythema multiforme; chronic inflammatory dermatoses, including but not limited to, psoriasis, lichen planus, and lupus erythematosus; blistering (bullous) diseases, including but not limited to, pemphigus, bullous pemphigoid, dermatitis herpetiformis, and noninflammatory blistering diseases: epidermolysis bullosa and porphyria; disorders of epidermal appendages, including but not limited to, acne vulgaris; panniculitis, including but not limited to, erythema nodosum and erythema induratum; and infection and infestation, such as verrucae, molluscum contagiosum, impetigo, superficial fungal infections, and arthropod bites, stings, and infestations.

The compounds of preferred embodiments can be used in relation to disorders involving the spleen. Disorders involving the spleen include, but are not limited to, splenomegaly, including nonspecific acute splenitis, congestive spenomegaly, and spenic infarcts; neoplasms, congenital anomalies, and rupture. Disorders associated with splenomegaly include infections, such as nonspecific splenitis, infectious mononucleosis, tuberculosis, typhoid fever, brucellosis, cytomegalovirus, syphilis, malaria, histoplasmosis, toxoplasmosis, kala-azar, trypanosomiasis, schistosomiasis, leishmaniasis, and echinococcosis; congestive states related to partial hypertension, such as cirrhosis of the liver, portal or splenic vein thrombosis, and cardiac failure; lymphohematogenous disorders, such as Hodgkin disease, non-Hodgkin lymphomas/leukemia, multiple myeloma, myeloproliferative disorders, hemolytic anemias, and thrombocytopenic purpura; immunologic-inflammatory conditions, such as rheumatoid arthritis and systemic lupus erythematosus; storage diseases such as Gaucher disease, Niemann-Pick disease, and mucopolysaccharidoses; and other conditions, such as amyloidosis, primary neoplasms and cysts, and secondary neoplasms.

The compounds of preferred embodiments can be used in relation to disorders involving blood vessels. Disorders involving blood vessels include, but are not limited to, responses of vascular cell walls to injury, such as endothelial dysfunction and endothelial activation and intimal thickening; vascular diseases including, but not limited to, congenital anomalies, such as arteriovenous fistula, atherosclerosis, and hypertensive vascular disease, such as hypertension; inflammatory disease—the vasculitides, such as giant cell (temporal) arteritis, Takayasu arteritis, polyarteritis nodosa (classic), Kawasaki syndrome (mucocutaneous lymph node syndrome), microscopic polyanglitis (microscopic polyarteritis, hypersensitivity or leukocytoclastic anglitis), Wegener granulomatosis, thromboanglitis obliterans (Buerger disease), vasculitis associated with other disorders, and infectious arteritis; Raynaud disease; aneurysms and dissection, such as abdominal aortic aneurysms, syphilitic (luetic) aneurysms, and aortic dissection (dissecting hematoma); disorders of veins and lymphatics, such as varicose veins, thrombophlebitis and phlebothrombosis, obstruction of superior vena cava (superior vena cava syndrome), obstruction of inferior vena cava (inferior vena cava syndrome), and lymphangitis and lymphedema; tumors, including benign tumors and tumor-like conditions, such as hemangioma, lymphangioma, glomus tumor (glomangioma), vascular ectasias, and bacillary angiomatosis, and intermediate-grade (borderline low-grade malignant) tumors, such as Kaposi sarcoma and hemangloendothelioma, and malignant tumors, such as angiosarcoma and hemangiopericytoma; and pathology of therapeutic interventions in vascular disease, such as balloon angioplasty and related techniques and vascular replacement, such as coronary artery bypass graft surgery.

The compounds of preferred embodiments can be used in relation to disorders involving red cells. Disorders involving red cells include, but are not limited to, anemias, such as hemolytic anemias, including hereditary spherocytosis, hemolytic disease due to erythrocyte enzyme defects: glucose-6-phosphate dehydrogenase deficiency, sickle cell disease, thalassemia syndromes, paroxysmal nocturnal hemoglobinuria, immunohemolytic anemia, and hemolytic anemia resulting from trauma to red cells; and anemias of diminished erythropoiesis, including megaloblastic anemias, such as anemias of vitamin B12 deficiency: pernicious anemia, and anemia of folate deficiency, iron deficiency anemia, anemia of chronic disease, aplastic anemia, pure red cell aplasia, and other forms of marrow failure.

The compounds of preferred embodiments can be used in relation to disorders involving B-cells. Disorders involving B-cells include, but are not limited to precursor B-cell neoplasms, such as lymphoblastic leukemia/lymphoma. Peripheral B-cell neoplasms include, but are not limited to, chronic lymphocytic leukemia/small lymphocytic lymphoma, follicular lymphoma, diffuse large B-cell lymphoma, Burkitt lymphoma, plasma cell neoplasms, multiple myeloma, and related entities, lymphoplasmacytic lymphoma (Waldenstrom macroglobulinemia), mantle cell lymphoma, marginal zone lymphoma (MALToma), and hairy cell leukemia.

The compounds of preferred embodiments can be used in relation to disorders related to reduced platelet number. Disorders related to reduced platelet number, thrombocytopenia, include idiopathic thrombocytopenic purpura, including acute idiopathic thrombocytopenic purpura, drug-induced thrombocytopenia, HIV-associated thrombocytopenia, and thrombotic microangiopathies: thrombotic thrombocytopenic purpura and hemolytic-uremic syndrome.

The compounds of preferred embodiments can be used in relation to disorders involving precursor T-cell neoplasms. Disorders involving precursor T-cell neoplasms include precursor T lymphoblastic leukemia/lymphoma. Disorders involving peripheral T-cell and natural killer cell neoplasms include T-cell chronic lymphocytic leukemia, large granular lymphocytic leukemia, mycosis fungoides and Szary syndrome, peripheral T-cell lymphoma, unspecified, angioimmunoblastic T-cell lymphoma, angiocentric lymphoma (NK/T-cell lymphoma4a), intestinal T-cell lymphoma, adult T-cell leukemia/lymphoma, and anaplastic large cell lymphoma.

The compounds of preferred embodiments can be used in relation to disorders of the bone. Bone-forming cells include the osteoprogenitor cells, osteoblasts, and osteocytes. The disorders of the bone are complex because they can have an impact on the skeleton during any of its stages of development. Hence, the disorders can have variable manifestations and can involve one, multiple or all bones of the body. Such disorders include, congenital malformations, achondroplasia and thanatophoric dwarfism, diseases associated with abnormal matrix such as type 1 collagen disease, osteoporosis, Paget disease, rickets, osteomalacia, high-turnover osteodystrophy, low-turnover of aplastic disease, osteonecrosis, pyogenic osteomyelitis, tuberculous osteomyelitism, osteoma, osteoid osteoma, osteoblastoma, osteosarcoma, osteochondroma, chondromas, chondroblastoma, chondromyxoid fibroma, chondrosarcoma, fibrous cortical defects, fibrous dysplasia, fibrosarcoma, malignant fibrous histiocytoma, Ewing sarcoma, primitive neuroectodermal tumor, giant cell tumor, and metastatic tumors.

The compounds of preferred embodiments can be used in relation to disorders involving the tonsils. Disorders involving the tonsils include, but are not limited to, tonsillitis, Peritonsillar abscess, squamous cell carcinoma, dyspnea, hyperplasia, follicular hyperplasia, reactive lymphoid hyperplasia, non-Hodgkin's lymphoma and B-cell lymphoma.

The compounds of preferred embodiments can be used in relation to disorders involving the liver. Disorders involving the liver include, but are not limited to, hepatic injury; jaundice and cholestasis, such as bilirubin and bile formation; hepatic failure and cirrhosis, such as cirrhosis, portal hypertension, including ascites, portosystemic shunts, and splenomegaly; infectious disorders, such as viral hepatitis, including hepatitis A-E infection and infection by other hepatitis viruses, clinicopathologic syndromes, such as the carrier state, asymptomatic infection, acute viral hepatitis, chronic viral hepatitis, and fulminant hepatitis; autoimmune hepatitis, drug- and toxin-induced liver disease, such as alcoholic liver disease; inborn errors of metabolism and pediatric liver disease, such as hemochromatosis, Wilson disease, alpha.1-antitrypsin deficiency, and neonatal hepatitis; intrahepatic biliary tract disease, such as secondary biliary cirrhosis, primary biliary cirrhosis, primary sclerosing cholangitis, and anomalies of the biliary tree; circulatory disorders, such as impaired blood flow into the liver, including hepatic artery compromise and portal vein obstruction and thrombosis, impaired blood flow through the liver, including passive congestion and centrilobular necrosis and peliosis hepatis, hepatic vein outflow obstruction, including hepatic vein thrombosis (Budd-Chiari syndrome) and veno-occlusive disease; hepatic disease associated with pregnancy, such as preeclampsia and eclampsia, acute fatty liver of pregnancy, and intrehepatic cholestasis of pregnancy; hepatic complications of organ or bone marrow transplantation, such as drug toxicity after bone marrow transplantation, graft-versus-host disease and liver rejection, and nonimmunologic damage to liver allografts; tumors and tumorous conditions, such as nodular hyperplasias, adenomas, and malignant tumors, including primary carcinoma of the liver and metastatic tumors.

The compounds of preferred embodiments can be used in relation to disorders involving the colon. Disorders involving the colon include, but are not limited to, congenital anomalies, such as atresia and stenosis, Meckel diverticulum, congenital aganglionic megacolon-Hirschsprung disease; enterocolitis, such as diarrhea and dysentery, infectious enterocolitis, including viral gastroenteritis, bacterial enterocolitis, necrotizing enterocolitis, antibiotic-associated colitis (pseudomembranous colitis), and collagenous and lymphocytic colitis, miscellaneous intestinal inflammatory disorders, including parasites and protozoa, acquired immunodeficiency syndrome, transplantation, drug-induced intestinal injury, radiation enterocolitis, neutropenic colitis (typhlitis), and diversion colitis; idiopathic inflammatory bowel disease, such as Crohn disease and ulcerative colitis; tumors of the colon, such as non-neoplastic polyps, adenomas, familial syndromes, colorectal carcinogenesis, colorectal carcinoma, and carcinoid tumors.

The compounds of preferred embodiments can be used in relation to disorders involving the lung. Disorders involving the lung include, but are not limited to, congenital anomalies; atelectasis; diseases of vascular origin, such as pulmonary congestion and edema, including hemodynamic pulmonary edema and edema caused by microvascular injury, adult respiratory distress syndrome (diffuse alveolar damage), pulmonary embolism, hemorrhage, and infarction, and pulmonary hypertension and vascular sclerosis; chronic obstructive pulmonary disease, such as emphysema, chronic bronchitis, bronchial asthma, and bronchiectasis; diffuse interstitial (infiltrative, restrictive) diseases, such as pneumoconioses, sarcoidosis, idiopathic pulmonary fibrosis, desquamative interstitial pneumonitis, hypersensitivity pneumonitis, pulmonary eosinophilia (pulmonary infiltration with eosinophilia), Bronchiolitis obliterans-organizing pneumonia, diffuse pulmonary hemorrhage syndromes, including Goodpasture syndrome, idiopathic pulmonary hemosiderosis and other hemorrhagic syndromes, pulmonary involvement in collagen vascular disorders, and pulmonary alveolar proteinosis; complications of therapies, such as drug-induced lung disease, radiation-induced lung disease, and lung transplantation; tumors, such as bronchogenic carcinoma, including paraneoplastic syndromes, bronchioloalveolar carcinoma, neuroendocrine tumors, such as bronchial carcinoid, miscellaneous tumors, and metastatic tumors; pathologies of the pleura, including inflammatory pleural effusions, noninflammatory pleural effusions, pneumothorax, and pleural tumors, including solitary fibrous tumors (pleural fibroma) and malignant mesothelioma.

The compounds described herein can be administered as sole active ingredients and/or in a mixture with one or more additional active ingredients or agents that are therapeutically or nutritionally useful, such as antibiotics, vitamins, herbal extracts, anti-inflammatories, glucose, antipyretics, analgesics, growth factors (e.g., granulocyte-macrophage colony stimulating factor (GM-CSF), Interleukins (IL-1, IL-2, IL-3, IL-4, IL-5, IL-6, IL-7, IL-8, IL-9, IL-10 IL-11, IL-12, IL-13, IL-14, or IL-15), TPO, or SCF), or other growth factors such as CSF-1, SF, EPO, leukemia inhibitory factor (LIF), or fibroblast growth factor (FGF), as well as C-KIT ligand, M-CSF and TNF-α, PIXY-321 (GM-CSF/IL-3 fusion protein), macrophage inflammatory protein, stem cell factor, thrombopoietin, growth related oncogene, G-CSF, VEGF, chemical agents (e.g., AMD3100) or chemotherapy and the like.

The term, "in conjunction with", as used herein, refers to concurrent administration of the active compound with and additional agent (e.g., a growth factor or chemical agent), as well as administration of the active compound within several days (e.g., within approximately 1 to 7 days) of administration of the growth factor. Administration of the additional agent can be before, concurrent, or after administration of the active compound.

In some embodiments, the active compound can be administered alone, or in conjunction with other compounds or agents that mobilize stem cells, such as growth factors (e.g., G-CSF), chemical agents (e.g., AMD3100), drugs, such as cyclophosphamide or 5-fluorouracil; and/or certain antibodies, such as anti-VLA4. Combinations of these other compounds can also be used.

Some embodiments disclosed herein concern improved therapeutic approaches, wherein an effective amount of a Cdc42-specific inhibitor is combined or co-administered with at least one additional therapeutic agent (including, but not limited to, chemotherapeutic antineoplastics, apoptosis modulating agents, immunotherapeutics, antimicrobials, antivirals, antifungals, and anti-inflammatory agents) and/or therapeutic technique (e.g., surgical intervention, and/or radiotherapies). In some embodiments, compounds disclosed herein (e.g., a Cdc42-specific inhibitor) can sensitize a subject or cells within the subject to a second agent (e.g., a chemotherapeutic agent) or therapeutic technique (e.g., radiotherapy).

The terms "sensitize" and "sensitizing," as used herein, refer to making, through the administration of a first agent (e.g., a Cdc42-specific inhibitor), an animal or a cell within an animal more susceptible, or more responsive, to the biological effects (e.g., promotion or retardation of an aspect of cellular function including, but not limited to, cell growth, proliferation, invasion, angiogenesis, or apoptosis) of a second agent or therapeutic technique. The sensitizing effect of a first agent on a target cell can be measured as the difference in the intended biological effect (e.g., promotion or retardation of an aspect of cellular function including, but not limited to, cell growth, proliferation, invasion, angiogenesis, or apoptosis) observed upon the administration of a second agent or therapeutic technique with and without administration of the first agent. The response of the sensitized cell can be increased by at least 10%, at least 20%, at least 30%, at least 40%, at least 50%, at least 60%, at least 70%, at least 80%, at least 90%, at least 100%, at least 150%, at least 200%, at least 250%, at least 300%, at least 350%, at least 400%, at least 450%, or at least 500% over the response in the absence of the first agent.

The term "hyperproliferative disease" or "hyperproliferative disorder" as used herein, refers to any condition in which a localized population of proliferating cells in an animal is not governed by the usual limitations of normal growth. Examples of hyperproliferative disorders include tumors, neoplasms, lymphomas and the like. A neoplasm is said to be benign if it does not undergo invasion or metastasis and malignant if it does either of these. A "metastatic" cell means that the cell can invade and destroy neighboring body structures. Hyperplasia is a form of cell proliferation involving an increase in cell number in a tissue or organ without significant alteration in structure or function. Metaplasia is a form of controlled cell growth in which one type of fully differentiated cell substitutes for another type of differentiated cell.

The term "neoplastic disease," as used herein, refers to any abnormal growth of cells being either benign (non-cancerous) or malignant (cancerous).

The terms "anticancer agent" and "anticancer drug," as used herein, refer to any therapeutic agents (e.g., chemotherapeutic compounds and/or molecular therapeutic compounds), radiation therapies, or surgical interventions, used in the treatment of hyperproliferative diseases such as cancer (e.g., in mammals).

The term "anti-neoplastic agent," as used herein, refers to any compound that retards the proliferation, growth, or spread of a targeted (e.g., malignant) neoplasm.

The term "apoptosis modulating agents," as used herein, refers to agents which are involved in modulating (e.g., inhibiting, decreasing, increasing, promoting) apoptosis. Examples of apoptosis modulating agents include, but are not limited to, proteins and nucleic acids, which comprise a death domain or encode a death domain such as, but not limited to, Fas/CD95, TRAMP, TNF R1, DR1, DR2, DR3, DR4, DR5, DR6, FADD, and RIP. Small RNAs such as MIR RNAs can also be apoptosis modulating agents (e.g., MIR-34a). Other examples of apoptotic modulating agents include, but are not limited to, TNF-alpha, Fas ligand, antibodies to Fas/CD95 and other TNF family receptors, TRAIL, antibodies to TRAILR1 or TRAILR2, Bcl-2, p53, BAX, BAD, Akt, CAD, PI3 kinase, PPI, and caspase proteins. Modulating agents broadly include agonists and antagonists of TNF family receptors and TNF family ligands. Apoptosis modulating agents may be soluble or membrane bound (e.g. ligand or receptor). Preferred apoptosis modulating agents are inducers of apoptosis, such as TNF or a TNF-related ligand, particularly a TRAMP ligand, a Fas/CD95 ligand, a TNFR-1 ligand, or TRAIL.

A number of suitable anticancer agents are contemplated for combination or co-administration with a Cdc42-specific inhibitor to treat, prevent, or ameliorate any of the aforementioned diseases, maladies, conditions, or disorders. Indeed, some embodiments contemplate, but are not limited to, administration of a Cdc42-specific inhibitor in combination or co-administered with numerous anticancer agents such as: agents that induce apoptosis; polynucleotides (e.g., antisense, ribozymes, siRNA); polypeptides (e.g., enzymes and antibodies); biological mimetics (e.g., gossypol or BH3 mimetics); agents that bind (e.g., oligomerize or complex) Cdc42; alkaloids; alkylating agents; antitumor antibiotics; antimetabolites; hormones; platinum compounds; monoclonal or polyclonal antibodies (e.g., antibodies conjugated with anticancer drugs, toxins, defensins), toxins; radionuclides; biological response modifiers (e.g., interferons (e.g., IFN-alpha) and interleukins (e.g., IL-2)); adoptive immunotherapy agents; hematopoietic growth factors; agents that induce tumor cell differentiation (e.g., all-trans-retinoic acid); gene therapy reagents (e.g., antisense therapy reagents and nucleotides); tumor vaccines; angiogenesis inhibitors; proteasome inhibitors: NF-KB modulators; anti-CDK compounds; HDAC inhibitors; and the like. Numerous other examples of chemotherapeutic compounds and anticancer therapies suitable for mixture or co-administration with the disclosed inhibitors of Cdc42 are known to those skilled in the art.

In more embodiments, the Cdc42-specific inhibitors described herein and used in the methods disclosed are mixed or combined or co-administered with anticancer agents that induce or stimulate apoptosis. Agents that induce apoptosis which are suitable in such compositions, mixtures, therapies and methods include, but are not limited to, radiation (e.g., X-rays, gamma rays, UV); tumor necrosis factor (TNF)-related factors (e.g., TNF family receptor proteins, TNF family ligands, TRAIL, antibodies to TRAILR1 or TRAILR2); kinase inhibitors (e.g., epidermal growth factor receptor (EGFR) kinase inhibitor, vascular growth factor receptor (VGFR) kinase inhibitor, fibroblast growth factor receptor (FGFR) kinase inhibitor, platelet-derived growth factor receptor (PDGFR) kinase inhibitor, and Bcr-Abl kinase inhibitors (such as GLEEVEC®)); antisense molecules; antibodies (e.g., HERCEPTIN®, RITUXAN®, ZEVALIN®, and AVASTIN®); anti-estrogens (e.g., raloxifene and tamoxifen); anti-androgens (e.g., flutamide, bicalutamide, finasteride, aminoglutethamide, ketoconazole, and corticosteroids); cyclooxygenase 2 (COX-2) inhibitors (e.g., celecoxib, meloxicam, NS-398, and non-steroidal anti-inflammatory drugs (NSAIDs)); anti-inflammatory drugs (e.g., butazolidin, DECADRON®, DELTASONE®, dexamethasone, dexamethasone intensol, DEXONE®, HEXADROL®, hydroxychloroquine, METICORTEN®, oradexon, ORASONE®, oxyphenbutazone, PEDIAPRED®, phenyl butazone, PLAQUENIL®, prednisolone, prednisone, PRELONE®, and TANDEARIL®); and cancer chemotherapeutic drugs (e.g., irinotecan (CAMPTOSAR®), CPT-11, fludarabine (FLUDARA®), dacarbazine (DTIC®), dexamethasone, mitoxantrone, MYLOTARG®, VP-16®, cisplatin, carboplatin, oxaliplatin, 5-FU®, doxorubicin, gemcitabine, bortezomib, gefitinib, bevacizumab, TAXOTERE® or TAXOL®); cellular signaling molecules; ceramides and cytokines; staurosporine, and the like.

In still other embodiments, compositions and methods described provide a Cdc42-specific inhibitor and at least one anti-hyperproliferative or antineoplastic agent selected from alkylating agents, antimetabolites, and natural products (e.g., herbs and other plant and/or animal derived compounds).

Alkylating agents suitable for use in the present compositions, mixtures, therapies, and methods include, but are not limited to: 1) nitrogen mustards (e.g., mechlorethamine, cyclophosphamide, ifosfamide, melphalan (L-sarcolysin); and chlorambucil); 2) ethylenimines and methylmelamines (e.g., hexamethylmelamine and thiotepa); 3) alkyl sulfonates (e.g., busulfan); 4) nitrosoureas (e.g., carmustine (BCNU); lomustine (CCNU); semustine (methyl-CCNU); and streptozocin (streptozotocin)); and 5) triazenes (e.g., dacarbazine (DTIC®; dimethyltriazenoimid-azolecarboxamide).

In some embodiments, antimetabolites suitable for use in the present compositions, mixtures, therapies, and methods include, but are not limited to: 1) folic acid analogs (e.g., methotrexate (amethopterin)); 2) pyrimidine analogs (e.g., fluorouracil (5-fluorouracil; 5-FU®), floxuridine (fluorodeoxyuridine; FudR), and cytarabine (cytosine arabinoside)); and 3) purine analogs (e.g., mercaptopurine (6-mercaptopurine; 6-MP), thioguanine (6-thioguanine; TG), and pentostatin (2'-deoxycoformycin)).

In still further embodiments, chemotherapeutic agents suitable for use with the compositions, mixtures, therapies, and methods described herein include, but are not limited to: 1) vinca alkaloids (e.g., vinblastine (VLB), vincristine); 2) epipodophyllotoxins (e.g., etoposide and teniposide); 3) antibiotics (e.g., dactinomycin (actinomycin D), daunorubicin (daunomycin; rubidomycin), doxorubicin, bleomycin, plicamycin (mithramycin), and mitomycin (mitomycin C)); 4) enzymes (e.g., L-asparaginase); 5) biological response modifiers (e.g., interferon-alfa); 6) platinum coordinating complexes (e.g., cisplatin (cis-DDP) and carboplatin); 7) anthracenediones (e.g., mitoxantrone); 8) substituted ureas (e.g., hydroxyurea); 9) methylhydrazine derivatives (e.g., procarbazine (N-methylhydrazine; M1H)); 10) adrenocortical suppressants (e.g., mitotane (o,p'-DDD) and aminoglutethimide); 11) adrenocorticosteroids (e.g., prednisone); 12) progestins (e.g., hydroxyprogesterone caproate, medroxyprogesterone acetate, and megestrol acetate); 13) estrogens (e.g., diethylstilbestrol and ethinyl estradiol); 14) antiestrogens (e.g., tamoxifen); 15) androgens (e.g., testosterone propionate and fluoxymesterone); 16) antiandrogens (e.g., flutamide): and 17) gonadotropin-releasing hormone analogs (e.g., leuprolide).

Any oncolytic agent that is routinely used in a cancer therapy context finds use in the compositions and methods disclosed herein. For example, the U.S. Food and Drug Administration maintains a formulary of oncolytic agents approved for use in the United States. International counterpart agencies to the U.S.F.D.A. maintain similar formularies.

In some embodiments, conventional anticancer agents for use in administration with the present compounds include, but are not limited to, adriamycin, 5-fluorouracil, etoposide, camptothecin, actinomycin D, mitomycin C, cisplatin, docetaxel, gemcitabine, carboplatin, oxaliplatin, bortezomib, gefitinib, bevacizumab, demethylating agents, inhibitors of her-2, inhibitors of IGF-1R, VEGF, inhibitors of VEGFR, mTOR inhibitors, mitotic inhibitors, Smad inhibitors and taxanes. These agents can be prepared and used singularly, in combined therapeutic compositions, in kits, or in combination with immunotherapeutic agents, and the like.

For a more detailed description of anticancer agents and other therapeutic agents, those skilled in the art are referred to any number of instructive manuals including, but not limited to, the Physician's Desk Reference and to Goodman and Gilman's "Pharmaceutical Basis of Therapeutics" tenth edition, Eds. Hardman et al., 2002.

Some embodiments disclosed herein relate to an improved radiation therapy, wherein a Cdc42-specific inhibitor is provided before, during, or after a radiation therapy. Embodiments disclosed herein are not limited by the types, amounts, or delivery and administration systems used to deliver the therapeutic dose of radiation to a subject. For example, the subject may receive photon radiotherapy, particle beam radiation therapy, other types of radiotherapies, and combinations thereof. In some embodiments, the radiation is delivered to the subject using a linear accelerator. In still other embodiments, the radiation is delivered using a gamma knife, and in others, the radiation administered in the form of a radioactive implantable pellet.

The source of radiation can be external or internal to the subject. External radiation therapy is most common and involves directing a beam of high-energy radiation to a tumor site through the skin using, for instance, a linear accelerator. While the beam of radiation is localized to the tumor site, it is nearly impossible to avoid exposure of normal, healthy tissue. However, external radiation is usually well tolerated by patients. Internal radiation therapy involves implanting a radiation-emitting source, such as beads, wires, pellets, capsules, particles, and the like, inside the body at or near the tumor site including the use of delivery systems that specifically target cancer cells (e.g., using particles attached to cancer cell binding ligands). Such implants can be removed following treatment, or left in the body inactive. Types of internal radiation therapy include, but are not limited to, brachytherapy, interstitial irradiation, intracavity irradiation, radioimmunotherapy, and the like.

The subject may optionally receive radiosensitizers in addition to the Cdc42-specific inhibitor and radiation (e.g., metronidazole, misonidazole, intra-arterial Budr, intravenous iododeoxyuridine (IudR), nitroimidazole, 5-substituted-4-nitroimidazoles, 2H-isoindolediones, [[(2-bromoethyl)-amino]methyl]-nitro-1H-imidazole-1-ethanol, nitroaniline derivatives, DNA-affinic hypoxia selective cytotoxins, halogenated DNA ligand, 1,2,4 benzotriazine oxides, 2-nitroimidazole derivatives, fluorine-containing nitroazole derivatives, benzamide, nicotinamide, acridine-intercalator, 5-thiotretrazole derivative, 3-nitro-1,2,4-triazole, 4,5-dinitroimidazole derivative, hydroxylated texaphrins, cisplatin, mitomycin, tiripazamine, nitrosourea, mercaptopurine, methotrexate, fluorouracil, bleomycin, vincristine, carboplatin, epirubicin, doxorubicin, cyclophosphamide, vindesine, etoposide, paclitaxel, heat (hyperthermia), and the like), radioprotectors (e.g., cysteamine, aminoalkyl dihydrogen phosphorothioates, amifostine (WR 2721), IL-1, IL-6, and the like). Radiosensitizers enhance the killing of cancer cells. Radioprotectors protect healthy tissue from the harmful effects of radiation.

Any type of radiation can be administered to a patient, so long as the dose of radiation is tolerated by the patient without unacceptable negative side-effects. Suitable types of radiotherapy include, for example, ionizing (electromagnetic) radiotherapy (e.g., X-rays or gamma rays) or particle beam radiation therapy (e.g., high linear energy radiation). Ionizing radiation refers to radiation comprising particles or photons that have sufficient energy to produce ionization, e.g., gain or loss of electrons (as described in, for example, U.S. Pat. No. 5,770,581 incorporated herein by reference in its entirety). The effects of radiation can be at least partially controlled by the clinician. The dose of radiation can be fractionated for maximal target cell exposure and reduced toxicity.

Methods of Identifying Cells in Peripheral Blood

Any methods including quantitative and qualitative methods can be used to identify that the hematopoietic stem cells have been mobilized into the peripheral blood. The methods typically involve isolating a quantity of the patient's blood and analyzing the quantity of the cells within the blood. Any method can be used to analyze the number of cells, including but not limited to: ELISA to identify the specific cells, FACS analysis, coulter counters and other blood counting devices, morphological identification, and PCR. The cells can be identified by any method known to one of skill in the art, including but not limited to, the identification of one or more proteins which are specifically expressed by the stem cells, by morphology, by mRNA expression, and by PCR. The identification of the cells can be done at any time after administration of the GTPase inhibitor (e.g., a Cdc42-specific inhibitor), including but not limited to: 5 minutes, 10 minutes, 20 minutes, 30 minutes, 45 minutes, 1 hour, 1.5 hours, 2 hours, 3 hours, 4 hours, 5 hours, 6 hours, 7 hours, 8 hours, 9 hours, 10 hours, 12 hours, 1 day, 2 days, 3 days, 4 days, 5 days, 6 days, 7 days, 2 weeks, 1 month, 2 months, 3 months, 4 months, 5 months, 6 months, 7 months, 8 months, 9 months, 10 months, 1 year, 2 years. Further, the mobilization can be identified soon after treatment to identify whether the treatment is working. If the treatment does not appear to be working, an alternative Cdc-42-specific inhibitor or a second inhibitor can be administered.

The efficacy of the mobilization can be tested throughout treatment with the GTPase inhibitor (e.g., Cdc42-specific inhibitor), or alternatively, an initial test to determine efficacy can be performed. In some embodiments, a test can be performed 1 day after treatment and again 1 week after treatment.

Pharmaceutical Compositions and Administration

Compounds, or mixtures of compounds described herein, can be synthetic, naturally-occurring, or a combination thereof. Compounds, or mixtures of compounds described herein can comprise amino acids, nucleotides, hydrocarbons, lipids, polysaccharides, etc. Compounds, or mixtures of compounds described herein preferably comprise a Cdc42-specific inhibitor (e.g., CASIN). Compounds, or mixtures of compounds described herein, can be formulated into pharmaceutical composition comprising a pharmaceutically acceptable carrier and other excipients as apparent to the skilled worker. Such composition can additionally contain effective amounts of other compounds, especially for the treatment of conditions, diseases, and/or disorders described herein.

Some embodiments comprise the administration of a pharmaceutically effective quantity of active agent or its pharmaceutically acceptable salts or esters, active agent analogs or their pharmaceutically acceptable salts or esters, or a combination thereof.

The compositions and preparations described preferably contain at least 0.1% of active agent. The percentage of the compositions and preparations can, of course, be varied, and can contain between about 2% and 60% of the weight of the amount administered. Preferably, the percentage of the compositions and preparations can contain between about 2, 5, 10, or 15% and 30, 35, 40, 45, 50, 55, or 60% of the weight of the amount administered. The amount of active compounds in such pharmaceutically useful compositions and preparations is such that a suitable dosage will be obtained.

The active agent can form salts, which are also within the scope of the preferred embodiments. Reference to a compound of the active agent herein is understood to include reference to salts thereof, unless otherwise indicated. The term "salt(s)", as employed herein, denotes acidic and/or basic salts formed with inorganic and/or organic acids and bases. In addition, when an active agent contains both a basic moiety, such as, but not limited to an amine or a pyridine or imidazole ring, and an acidic moiety, such as, but not limited to a carboxylic acid, zwitterions ("inner salts") can be formed and are included within the term "salt(s)" as used herein. Pharmaceutically acceptable (e.g., non-toxic, physiologically acceptable) salts are preferred, although other salts are also useful, e.g., in isolation or purification steps, which can be employed during preparation. Salts of the compounds of the active agent can be formed, for example, by reacting a compound of the active agent with an amount of acid or base, such as an equivalent amount, in a medium such as one in which the salt precipitates or in an aqueous medium followed by lyophilization.

The active agents which contain a basic moiety, such as, but not limited to an amine or a pyridine or imidazole ring, can form salts with a variety of organic and inorganic acids. Exemplary acid addition salts include acetates (such as those formed with acetic acid or trihaloacetic acid, for example, trifluoroacetic acid), adipates, alginates, ascorbates, aspartates, benzoates, benzenesulfonates, bisulfates, borates, butyrates, citrates, camphorates, camphorsulfonates, cyclopentanepropionates, digluconates, dodecylsulfates, ethanesulfonates, fumarates, glucoheptanoates, glycerophosphates, hemisulfates, heptanoates, hexanoates, hydrochlorides (formed with hydrochloric acid), hydrobromides (formed with hydrogen bromide), hydroiodides, 2-hydroxyethanesulfonates, lactates, maleates (formed with maleic acid), methanesulfonates (formed with methanesulfonic acid), 2-naphthalenesulfonates, nicotinates, nitrates, oxalates, pectinates, persulfates, 3-phenylpropionates, phosphates, picrates, pivalates, propionates, salicylates, succinates, sulfates (such as those formed with sulfuric acid), sulfonates (such as those mentioned herein), tartrates, thiocyanates, toluenesulfonates such as tosylates, undecanoates, and the like.

The active agents which contain an acidic moiety, such as, but not limited to a carboxylic acid, can form salts with a variety of organic and inorganic bases. Exemplary basic salts include ammonium salts, alkali metal salts such as sodium, lithium, and potassium salts, alkaline earth metal salts such as calcium and magnesium salts, salts with organic bases (for example, organic amines) such as benzathines, dicyclohexylamines, hydrabamines [formed with N,N-bis(dehydro-abietyl)ethylenediamine], N-methyl-D-glucamines, N-methyl-D-glucamides, t-butyl amines, and salts with amino acids such as arginine, lysine and the like. Basic nitrogen-containing groups can be quaternized with agents such as lower alkyl halides (e.g., methyl, ethyl, propyl, and butyl chlorides, bromides and iodides), dialkyl sulfates (e.g., dimethyl, diethyl, dibutyl, and diamyl sulfates), long chain halides (e.g., decyl, lauryl, myristyl and stearyl chlorides, bromides and iodides), aralkyl halides (e.g., benzyl and phenethyl bromides), and others.

Prodrugs and solvates of the compounds of the preferred embodiments are also contemplated herein. The term "prodrug", as employed herein, denotes a compound which, upon administration to a subject, undergoes chemical conversion by metabolic or chemical processes to yield a compound of the active agent, and/or a salt and/or solvate thereof. Solvates of the active agent are preferably hydrates.

Active agent, and salts thereof, can exist in their tautomeric form (for example, as an amide or imino ether). All such tautomeric forms are contemplated herein as part of the preferred embodiments.

All stereoisomers of the present compounds, such as those, for example, which can exist due to asymmetric carbons on any of the substituents, including enantiomeric forms (which can exist even in the absence of asymmetric carbons) and diastereomeric forms, are contemplated and within the scope of the preferred embodiments. Individual stereoisomers of the compounds of the preferred embodiments can, for example, be substantially free of other isomers, or can be admixed, for example, as racemates or with all other or other selected, stereoisomers. The chiral centers of the preferred embodiments can have the S or R configuration as defined by the IUPAC 1974 Recommendations.

When the compounds according to the preferred embodiments are in the forms of salts, they are preferably pharmaceutically acceptable salts. Such salts include pharmaceutically acceptable acid addition salts, pharmaceutically acceptable base addition salts, pharmaceutically acceptable metal salts, ammonium and alkylated ammonium salts. Acid addition salts include salts of inorganic acids as well as organic acids. Representative examples of suitable inorganic acids include hydrochloric, hydrobromic, hydroiodic, phosphoric, sulfuric, nitric acids and the like. Representative examples of suitable organic acids include formic, acetic, trichloroacetic, trifluoroacetic, propionic, benzoic, cinnamic, citric, fumaric, glycolic, lactic, maleic, malic, malonic, mandelic, oxalic, picric, pyruvic, salicylic, succinic, methanesulfonic, ethanesulfonic, tartaric, ascorbic, pamoic, bismethylene salicylic, ethanedisulfonic, gluconic, citraconic, aspartic, stearic, palmitic, EDTA, glycolic, p-aminobenzoic, glutamic, benzenesulfonic, p-toluenesulfonic acids, sulphates, nitrates, phosphates, perchlorates, borates, acetates, benzoates, hydroxynaphthoates, glycerophosphates, ketoglutarates and the like. Examples of metal salts include lithium, sodium, potassium, magnesium salts and the like. Examples of ammonium and alkylated ammonium salts include ammonium, methylammonium, dimethylammonium, trimethylammonium, ethylammonium, hydroxyethylammonium, diethylammonium, butylammonium, tetramethylammonium salts and the like. Examples of organic bases include lysine, arginine, guanidine, diethanolamine, choline and the like.

The pharmaceutically acceptable salts can be prepared by reacting the active agent with 1 to 4 equivalents of a base such as sodium hydroxide, sodium methoxide, sodium hydride, potassium t-butoxide, calcium hydroxide, magnesium hydroxide and the like, in solvents like ether, THF, methanol, t-butanol, dioxane, isopropanol, ethanol, etc. Mixture of solvents can be used. Organic bases like lysine, arginine, diethanolamine, choline, guandine and their derivatives etc. can also be used. Alternatively, acid addition salts wherever applicable are prepared by treatment with acids such as hydrochloric acid, hydrobromic acid, nitric acid, sulfuric acid, phosphoric acid, p-toluenesulphonic acid, methanesulfonic acid, fonic acid, acetic acid, citric acid, maleic acid salicylic acid, hydroxynaphthoic acid, ascorbic acid, palmitic acid, succinic acid, benzoic acid, benzenesulfonic acid, tartaric acid and the like in solvents like ethyl acetate, ether, alcohols, acetone, THF, dioxane, etc. Mixture of solvents can also be used.

As indicated above, a further object of the preferred embodiments relates to a pharmaceutical composition comprising at least one compound (e.g., a Cdc42-specific inhibitor such as CASIN) and a pharmaceutically acceptable vehicle or support.

The compounds can be formulated in various forms, including solid and liquid forms, such as tablets, gel, syrup, powder, aerosol, etc.

The compositions of the preferred embodiments can contain physiologically acceptable diluents, fillers, lubricants, excipients, solvents, binders, stabilizers, and the like. Diluents that can be used in the compositions include but are not limited to dicalcium phosphate, calcium sulphate, lactose, cellulose, kaolin, mannitol, sodium chloride, dry starch, powdered sugar and for prolonged release tablet-hydroxy propyl methyl cellulose (HPMC). The binders that can be used in the compositions include but are not limited to starch, gelatin and fillers such as sucrose, glucose, dextrose and lactose.

Natural and synthetic gums that can be used in the compositions include but are not limited to sodium alginate, ghatti gum, carboxymethyl cellulose, methyl cellulose, polyvinyl pyrrolidone and veegum. Excipients that can be used in the compositions include but are not limited to microcrystalline cellulose, calcium sulfate, dicalcium phosphate, starch, magnesium stearate, lactose, and sucrose. Stabilizers that can be used include but are not limited to polysaccharides such as acacia, agar, alginic acid, guar gum and tragacanth, amphotsics such as gelatin and synthetic and semi-synthetic polymers such as carbomer resins, cellulose ethers and carboxymethyl chitin.

Solvents that can be used include but are not limited to Ringers solution, water, distilled water, dimethyl sulfoxide to 50% in water, propylene glycol (neat or in water), phosphate buffered saline, balanced salt solution, glycol and other conventional fluids.

The dosages and dosage regimen in which the compounds are administered will vary according to the dosage form, mode of administration, the condition being treated and particulars of the patient being treated. Accordingly, optimal therapeutic concentrations will be best determined at the time and place through routine experimentation.

The compounds according to the preferred embodiments can also be used enterally. Orally, the compounds according to the preferred embodiments are suitable administered at the rate of 100 μg to 100 mg per day per kg of body weight. Preferably, orally, the compounds according to the preferred embodiments are suitable administered at the rate of about 100, 150, 200, 250, 300, 350, 400, 450, or 500 μg to about 1, 5, 10, 25, 50, 75, 100 mg per day per kg of body weight. The required dose can be administered in one or more portions. For oral administration, suitable forms are, for example, tablets, gel, aerosols, pills, dragees, syrups, suspensions, emulsions, solutions, powders and granules; a preferred method of administration consists in using a suitable form containing from 1 mg to about 500 mg of active substance. Preferably, a method of administration consists in using a suitable form containing from about 1, 2, 5, 10, 25, or 50 mg to about 100, 200, 300, 400, 500 mg of active substance.

The compounds according to the preferred embodiments can also be administered parenterally in the form of solutions or suspensions for intravenous or intramuscular perfusions or injections. In that case, the compounds according to the preferred embodiments are generally administered at the rate of about 10 μg to 10 mg per day per kg of body weight; a preferred method of administration consists of using solutions or suspensions containing approximately from 0.01 mg to 1 mg of active substance per ml. Preferably, the compounds according to the preferred embodiments are generally administered at the rate of about 10, 20, 30, 40, 50, 60, 70, 80, 90, or 100 μg to 1, 2, 3, 4, 5, 6, 7, 8, 9, or 10 mg per day per kg of body weight; a preferred method of administration consists of using solutions or suspensions containing approximately from 0.01, 0.02, 0.03, 0.04, or 0.5 mg to 0.1, 0.2, 0.3, 0.4, 0.5, 0.6, 0.7, 0.8, 0.9, or 1 mg of active substance per ml.

The compounds can be used in a substantially similar manner to other known anti-tumor agents for treating (both chemopreventively and therapeutically) various tumors. For the compounds of the preferred embodiments, the anti-tumor dose to be administered, whether a single dose, multiple dose, or a daily dose, will of course vary with the particular compound employed because of the varying potency of the compound, the chosen route of administration, the size of the recipient, the type of tumor, and the nature of the patient's condition. The dosage to be administered is not subject to definite bounds, but it will usually be an effective amount, or the equivalent on a molar basis of the pharmacologically active free form produced from a dosage formulation upon the metabolic release of the active drug to achieve its desired pharmacological and physiological effects. For example, an oncologist skilled in the art of cancer treatment will be able to ascertain, without undue experimentation, appropriate protocols for the effective administration of the compounds of the preferred embodiments related to cancer therapy, such as by referring to the earlier published studies on compounds found to have anti-tumor properties.

The active compounds and/or pharmaceutical compositions of the embodiments disclosed herein can be administered according to various routes, typically by injection, such as local or systemic injection(s). For example, intratumoral injections are preferred for treating existing cancers. However, other administration routes can be used as well, such as intramuscular, intravenous, intradermic, subcutaneous, etc. Furthermore, repeated injections can be performed, if needed, although it is believed that limited injections will be needed in view of the efficacy of the compounds.

For ex vivo administration, the active agent can be administered by any standard method that would maintain viability of the cells, such as by adding it to culture medium (appropriate for the target cells) and adding this medium directly to the cells. As is known in the art, any medium used in this method can be aqueous and non-toxic so as not to render the cells non-viable. In addition, it can contain standard nutrients for maintaining viability of cells, if desired. For in vivo administration, the complex can be added to, for example, to a pharmaceutically acceptable carrier, e.g., saline and buffered saline, and administered by any of several means known in the art. Examples of administration include parenteral administration, e.g., by intravenous injection including regional perfusion through a blood vessel supplying the tissues(s) or organ(s) having the target cell(s), or by inhalation of an aerosol, subcutaneous or intramuscular injection, topical administration such as to skin wounds and lesions, direct transfection into, e.g., bone marrow cells prepared for transplantation and subsequent transplantation into the subject, and direct transfection into an organ that is subsequently transplanted into the subject. Further administration methods include oral administration, particularly when the active agent is encapsulated, or rectal administration, particularly when the active agent is in suppository form.

It is contemplated that such target cells can be located within a subject or human patient, in which case a safe and effective amount of the active agent, in pharmacologically acceptable form, would be administered to the patient. Generally speaking, it is contemplated that useful pharmaceutical compositions of the preferred embodiments will include the selected active compound derivative in a convenient amount, e.g., from about 0.001% to about 10% (w/w) that is diluted in a pharmacologically or physiologically acceptable carrier, such as, for example, phosphate buffered saline. The route of administration and ultimate amount of material that is administered to the subject under such circumstances will depend upon the intended application and will be apparent to those of skill in the art in light of the examples which follow.

Any composition chosen should be of low or non-toxicity to the cell. Toxicity for any given compound can vary with the concentration of compound used. It is also beneficial if the compound chosen is metabolized or eliminated by the body and if this metabolism or elimination is done in a manner that will not be harmfully toxic.

The examples are illustrative of the types of compounds to be used in the method claimed herein; the list is not exhaustive. Derivatives of the above compounds that fit the criteria of the claims are preferably also be considered when choosing an active compound.

The compound is preferably administered such that a therapeutically effective concentration of the compound is in contact with the affected cells of the body. The dose administered to a subject, particularly a human, in the context of the preferred embodiments is preferably sufficient to effect a therapeutic response in the subject over a reasonable period of time. The dose will be determined by the strength of the particular compound employed and the condition of the subject, as well as the body weight of the subject to be treated. The existence, nature, and extent of any adverse side effects that might accompany the administration of a particular compound also will determine the size of the dose and the particular route of administration employed with a particular patient. In general, the compounds of the preferred embodiments are therapeutically effective at low doses. The generally useful dose range is from about 0.001 mM, or less, to about 100 mM, or more. Preferably, the effective dose range is from about 0.01, 0.05, 0.1, 0.5, 0.6, 0.7, 0.8, or 0.9 mM, to about 1, 2, 3, 4, 5, 6, 7, 8, 9, or 10 mM. Accordingly, the compounds will be generally administered in low doses.

The compound can be administered in a pharmaceutically acceptable carrier. Pharmaceutically acceptable carriers are well-known to those who are skilled in the art. The choice of carrier will be determined in part by the particular compound, as well as by the particular method used to administer the composition. Accordingly, there is a wide variety of suitable formulations of the pharmaceutical composition of the preferred embodiments.

The compounds can be administered orally, topically, parenterally, by inhalation or spray, vaginally, rectally or sublingually in dosage unit formulations. The term "administration by injection" includes but is not limited to: intravenous, intraarticular, intramuscular, subcutaneous and parenteral injections, as well as use of infusion techniques. Dermal administration can include topical application or transdermal administration. One or more compounds can be present in association with one or more non-toxic pharmaceutically acceptable carriers and if desired other active ingredients.

Compositions intended for oral use can be prepared according to any suitable method known to the art for the manufacture of pharmaceutical compositions. Such compositions can contain one or more agents selected from the group consisting of diluents, sweetening agents, flavoring agents, coloring agents and preserving agents in order to provide palatable preparations. Tablets contain the active ingredient in admixture with non-toxic pharmaceutically acceptable excipients that are suitable for the manufacture of tablets. These excipients can be, for example, inert diluents, such as calcium carbonate, sodium carbonate, lactose, calcium phosphate or sodium phosphate; granulating and disintegrating agents, for example, corn starch, or alginic acid; and binding agents, for example magnesium stearate, stearic acid or talc. The tablets can be uncoated or they can be coated by known techniques to delay disintegration and adsorption in the gastrointestinal tract and thereby provide a sustained action over a longer period. For example, a time delay material such as glyceryl monostearate or glyceryl distearate can be employed. These compounds can also be prepared in solid, rapidly released form.

Formulations for oral use can also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin or olive oil.

Aqueous suspensions containing the active materials in admixture with excipients suitable for the manufacture of aqueous suspensions can also be used. Such excipients are suspending agents, for example sodium carboxymethylcellulose, methylcellulose, hydroxypropyl-methylcellulose, sodium alginate, polyvinylpyrrolidone, gum tragacanth and gum acacia; dispersing or wetting agents can be a naturally-occurring phosphatide, for example, lecithin, or condensation products of an alkylene oxide with fatty acids, for example polyoxyethylene stearate, or condensation products of ethylene oxide with long chain aliphatic alcohols, for example heptadecaethylene oxycetanol, or condensation products of ethylene oxide with partial esters derived from fatty acids and hexitol such as polyoxyethylene sorbitol monooleate, or condensation products of ethylene oxide with partial esters derived from fatty acids and hexitol anhydrides, for example polyethylene sorbitan monooleate. The aqueous suspensions can also contain one or more preservatives, for example ethyl, or n-propyl p-hydroxybenzoate, one or more coloring agents, one or more flavoring agents, and one or more sweetening agents, such as sucrose or saccharin.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example, sweetening, flavoring and coloring agents, can also be present.

The compounds can also be in the form of non-aqueous liquid formulations, e.g., oily suspensions which can be formulated by suspending the active ingredients in a vegetable oil, for example arachis oil, olive oil, sesame oil or peanut oil, or in a mineral oil such as liquid paraffin. The oily suspensions can contain a thickening agent, for example beeswax, hard paraffin or cetyl alcohol. Sweetening agents such as those set forth above, and flavoring agents can be added to provide palatable oral preparations. These compositions can be preserved by the addition of an anti-oxidant such as ascorbic acid.

Compounds of the preferred embodiments can also be administrated transdermally using methods known to those skilled in the art. For example, a solution or suspension of an active agent in a suitable volatile solvent optionally containing penetration enhancing agents can be combined with additional additives known to those skilled in the art, such as matrix materials and bacteriocides. After sterilization, the resulting mixture can be formulated following known procedures into dosage forms. In addition, on treatment with emulsifying agents and water, a solution or suspension of an active agent can be formulated into a lotion or salve.

Suitable solvents for processing transdermal delivery systems are known to those skilled in the art, and include lower alcohols such as ethanol or isopropyl alcohol, lower ketones such as acetone, lower carboxylic acid esters such as ethyl acetate, polar ethers such as tetrahydrofuran, lower hydrocarbons such as hexane, cyclohexane or benzene, or halogenated hydrocarbons such as dichloromethane, chloroform, trichlorotrifluoroethane, or trichlorofluoroethane. Suitable solvents can also include mixtures of one or more materials selected from lower alcohols, lower ketones, lower carboxylic acid esters, polar ethers, lower hydrocarbons, halogenated hydrocarbons.

Suitable penetration enhancing materials for transdermal delivery system are known to those skilled in the art, and include, for example, monohydroxy or polyhydroxy alcohols such as ethanol, propylene glycol or benzyl alcohol, saturated or unsaturated C8-C18 fatty alcohols such as lauryl alcohol or cetyl alcohol, saturated or unsaturated C8-C18 fatty acids such as stearic acid, saturated or unsaturated fatty esters with up to 24 carbons such as methyl, ethyl, propyl, isopropyl, n-butyl, sec-butyl, isobutyl, tertbutyl or monoglycerin esters of acetic acid, capronic acid, lauric acid, myristinic acid, stearic acid, or palmitic acid, or diesters of saturated or unsaturated dicarboxylic acids with a total of up to about 24 carbons such as diisopropyl adipate, diisobutyl adipate, diisopropyl sebacate, diisopropyl maleate, or diisopropyl fumarate. Additional penetration enhancing materials include phosphatidyl derivatives such as lecithin or cephalin, terpenes, amides, ketones, ureas and their derivatives, and ethers such as dimethyl isosorbid and diethyleneglycol monoethyl ether. Suitable penetration enhancing formulations can also include mixtures of one or more materials selected from monohydroxy or polyhydroxy alcohols, saturated or unsaturated C8-C18 fatty alcohols, saturated or unsaturated C8-C18 fatty acids, saturated or unsaturated fatty esters with up to 24 carbons, diesters of saturated or unsaturated discarboxylic acids with a total of up to 24 carbons, phosphatidyl derivatives, terpenes, amides, ketones, ureas and their derivatives, and ethers.

Suitable binding materials for transdermal delivery systems are known to those skilled in the art and include polyacrylates, silicones, polyurethanes, block polymers, styrenebutadiene copolymers, and natural and synthetic rubbers. Cellulose ethers, derivatized polyethylenes, and silicates can also be used as matrix components. Additional additives, such as viscous resins or oils can be added to increase the viscosity of the matrix.

Pharmaceutical compositions of the preferred embodiments can also be in the form of oil-in-water emulsions. The oil phase can be a vegetable oil, for example olive oil or arachis oil, or a mineral oil, for example, liquid paraffin or mixtures of these. Suitable emulsifying agents can be naturally-occurring gums, for example, gum acacia or gum tragacanth, naturally-occurring phosphatides, for example, soy bean, lecithin, and esters or partial esters derived from fatty acids and hexitol anhydrides, for example, sorbitan monooleate, and condensation products of the said partial esters with ethylene oxide, for example, polyoxyethylene sorbitan monooleate. The emulsions can also contain sweetening and flavoring agents. Syrups and elixirs can be formulated with sweetening agents, for example glycerol, propylene glycol, sorbitol or sucrose. Such formulations can also contain a demulcent, a preservative and flavoring and coloring agents.

The compounds can also be administered in the form of suppositories for rectal or vaginal administration of the drug. These compositions can be prepared by mixing the drug with a suitable nonirritating excipient which is solid at ordinary temperatures but liquid at the rectal temperature or vaginal temperature and will therefore melt in the rectum or vagina to release the drug. Such materials include cocoa butter and polyethylene glycols.

For all regimens of use disclosed herein for active agent, the daily oral dosage regimen will preferably be from about 0.01 to about 200 mg/Kg of total body weight. Preferably, the daily oral dosage regimen will preferably be from about 0.01, 0.05, 0.1, 0.5, 1, 2, 3, 4, or 5 to about 10, 50, 100, 110, 120, 130, 140, 150, 160, 170, 180, 190, or 200 mg/Kg of total body weight. The daily dosage for administration by injection, including intravenous, intramuscular, subcutaneous and parenteral injections, and use of infusion techniques will preferably be from 0.01 to 200 mg/Kg of total body weight. Preferably, the daily dosage for administration by injection, including intravenous, intramuscular, subcutaneous and parenteral injections, and use of infusion techniques will preferably be from about 0.01, 0.05, 0.1, 0.5, 1, 2, 3, 4, or 5 to about 10, 50, 100, 110, 120, 130, 140, 150, 160, 170, 180, 190, or 200 mg/Kg of total body weight. The daily vaginal dosage regime will preferably be from 0.01 to 200 mg/Kg of total body weight. The daily topical dosage regimen will preferably be from 0.01 to 200 mg administered between one to four times daily. The concentration for vaginal dosage and topical dosage will preferably be that required to maintain a daily dose is of from 0.1 to 200 mg/Kg. Preferably, the daily oral dosage regimen will preferably be from about 0.01, 0.05, 0.1, 0.5, 1, 2, 3, 4, or 5 to about 10, 50, 100, 110, 120, 130, 140, 150, 160, 170, 180, 190, or 200 mg/Kg of total body weight. The daily inhalation dosage regimen will preferably be from 0.01 to 10 mg/Kg of total body weight. Preferably, the daily inhalation dosage regimen will preferably be from about 0.01, 0.05, 0.1, 0.5, to about 1, 2, 3, 4, 5, or 10, mg/Kg of total body weight.

It will be appreciated by those skilled in the art that the particular method of administration will depend on a variety of factors, all of which are considered routinely when administering therapeutics. It will also be understood, however, that the specific dose level for any given patient will depend upon a variety of factors, including, the activity of the specific compound employed, the age of the patient, the body weight of the patient, the general health of the patient, the gender of the patient, the diet of the patient, time of administration, route of administration, rate of excretion, drug combinations, and the severity of the condition undergoing therapy. It will be further appreciated by one skilled in the art that the optimal course of treatment, i.e., the mode of treatment and the daily number of doses of an active agent or a pharmaceutically acceptable salt thereof given for a defined number of days, can be ascertained by those skilled in the art using conventional treatment tests.

The active compounds can be incorporated into pharmaceutical compositions suitable for administration to a subject, e.g., a human. Such compositions typically comprise the nucleic acid molecule, protein, modulator, or antibody and a pharmaceutically acceptable carrier.

As used herein the language "pharmaceutically acceptable carrier" is intended to include any and all solvents, dispersion media, coatings, antibacterial and antifungal agents, isotonic and absorption delaying agents, and the like, compatible with pharmaceutical administration. The use of such media and agents for pharmaceutically active substances is well known in the art. Except insofar as any conventional media or agent is incompatible with the active compound, such media can be used in the compositions of the preferred embodiments. Supplementary active compounds can also be incorporated into the compositions. A pharmaceutical composition of the preferred embodiments is formulated to be compatible with its intended route of administration. Examples of routes of administration include parenteral, e.g., intravenous, intradermal, subcutaneous, oral (e.g., inhalation), transdermal (topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfate; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes) can also be used as pharmaceutically acceptable carriers. These can be prepared according to methods known to those skilled in the art.

It is especially advantageous to formulate oral or parenteral compositions in dosage unit form for ease of administration and uniformity of dosage. "Dosage unit form" as used herein refers to physically discrete units suited as unitary dosages for the subject to be treated, each unit containing a predetermined quantity of active compound calculated to produce the desired therapeutic effect in association with the required pharmaceutical carrier. The specification for the dosage unit forms of the preferred embodiments are dictated by and directly dependent on the unique characteristics of the active compound and the particular therapeutic effect to be achieved, and the limitations inherent in the art of compounding such an active compound for the treatment of individuals.

As used herein, the term "therapeutically effective amount" means the total amount of each active component of the pharmaceutical composition or method that is sufficient to show a meaningful patient benefit, e.g., healing of chronic conditions or in an increase in rate of healing of such conditions, or in a reduction in aberrant conditions. This includes both therapeutic and prophylactic treatments. Accordingly, the compounds can be used at very early stages of a disease, or before early onset, or after significant progression. When applied to an individual active ingredient, administered alone, the term refers to that ingredient alone. When applied to a combination, the term refers to combined amounts of the active ingredients that result in the therapeutic effect, whether administered in combination, serially or simultaneously.

In practicing the method of treatment or use of the preferred embodiments, a therapeutically effective amount of one, two, or more of the active agents of the preferred embodiments is administered to a subject afflicted with a disease or disorder related to the mobilization of hematopoietic stem cells or progenitor cells, or to a tissue which has such disease or disorder. The active agents of the preferred embodiments can be administered in accordance with the method of the preferred embodiments either alone of in combination with other known therapies. When co-administered with one or more other therapies, the active agents of the preferred embodiments can be administered either simultaneously with the other treatment(s), or sequentially. If administered sequentially, the attending physician will decide on the appropriate sequence of administering the active agents of the preferred embodiments in combination with the other therapy.

Generally, a therapeutically effective amount of active agent (i.e., an effective dosage) ranges from about 0.001 to 5000 mg/kg body weight, more preferably about 0.01 to 1000 mg/kg body weight, more preferably about 0.01 to 500 mg/kg body weight, more preferably about 0.01 to 250 mg/kg body weight, more preferably about 0.01 to 100 mg/kg body weight, more preferably about 0.001 to 60 mg/kg body weight, more preferably about 0.01 to 25 mg/kg body weight, more preferably about 0.1 to 20 mg/kg body weight, and even more preferably about 1 to 10 mg/kg, 2 to 9 mg/kg, 3 to 8 mg/kg, 4 to 7 mg/kg, or 5 to 6 mg/kg body weight.

The skilled artisan will appreciate that certain factors can influence the dosage required to effectively treat a subject, including but not limited to the severity of the disease or disorder, previous treatments, the general health and/or age of the subject, and other diseases present. Moreover, treatment of a subject with a therapeutically effective amount can include a single treatment or, preferably, can include a series of treatments. In a preferred example, a subject is treated in the range of between about 0.1 to 20 mg/kg body weight, one time per week for between about 1 to 10 weeks, preferably between 2 to 8 weeks, more preferably between about 3 to 7 weeks, and even more preferably for about 4, 5, or 6 weeks. It will also be appreciated that the effective dosage used for treatment can increase or decrease over the course of a particular treatment. Changes in dosage can result and become apparent from the results of diagnostic assays as described herein.

The preferred embodiments encompass one or more additional agents that modulate expression or activity of Cdc42 GTPase. An agent can, for example, be a small molecule. For example, such small molecules include, but are not limited to, peptides, peptidomimetics, amino acids, amino acid analogs, polynucleotides, polynucleotide analogs, nucleotides, nucleotide analogs, organic or inorganic compounds (i.e., including heteroorganic and organometallic compounds) having a molecular weight less than about 10,000 grams per mole, organic or inorganic compounds having a molecular weight less than about 5,000 grams per mole, organic or inorganic compounds having a molecular weight less than about 1,000 grams per mole, organic or inorganic compounds having a molecular weight less than about 500 grams per mole, and salts, esters, and other pharmaceutically acceptable forms of such compounds.

In one embodiment, the additional agent can be a prenylation inhibitor, such as disclosed by U.S. Pat. Nos. 6,649,638; 5,420,245; 5,574,025; 5,523,430; 5,602,098; 5,631,401; 5,705,686; 5,238,922; 5,470,832; and 6,191,147, all of which are incorporated herein by reference in their entirety.

In another embodiment, the additional agent comprises one or more inhibitor of farnesyl protein transferase (FPTase), prenyl-protein transferase or geranylgeranyl-protein transferase as described in U.S. Pat. Nos. 6,572,850; 6,458,783; 6,423,751; 6,387,926; 6,242,433; 6,191,147; 6,166,067; 6,156,746; 6,083,979; 6,011,029; 5,929,077; 5,928,924; 5,843,941; 5,786,193; 5,629,302; 5,618,964; 5,574,025; 5,567,841; 5,523,430; 5,510,510; 5,470,832; 5,447,922; 6,596,735; 6,586,461; 6,586,447; 6,579,887; 6,576,639; 6,545,020; 6,539,309; 6,535,820; 6,528,523; 6,511,800; 6,500,841; 6,495,564; 6,492,381; 6,458,935; 6,451,812; 6,441,017; 6,440,989; 6,440,974; 6,432,959; 6,426,352; 6,410,541; 6,403,581; 6,399,615; 6,387,948; 6,387,905; 6,387,903; 6,376,496; 6,372,747; 6,362,188; 6,358,968; 6,329,376; 6,316,462; 6,294,552; 6,277,854; 6,268,394; 6,265,382; 6,262,110; 6,258,824; 6,248,756; 6,242,458; 6,239,140; 6,228,865; 6,228,856; 6,225,322; 6,218,401; 6,214,828; 6,214,827; 6,211,193; 6,194,438, which are specifically incorporated herein by reference in their entirety.

A "farnesyl protein transferase inhibitor" or "FPT inhibitor" or "FTI" is defined herein as a compound which: (i) potently inhibits FPT (but generally not geranylgeranyl protein transferase I) and (ii) blocks intracellular farnesylation of ras. FPT catalyzes the addition of an isoprenyl lipid moiety onto a cysteine residue present near the carboxy-terminus of the Ras protein. This is the first step in a post-translational processing pathway that is essential for both Ras membrane-association and Ras-induced oncogenic transformation. A number of FPT inhibitors have been reported, including a variety of peptidomimetic inhibitors as well as other small molecule inhibitors.

Farnesyl transferase inhibitors generally fall into two classes: analogs of farnesyl diphosphate; and protein substrates for farnesyl transferase. Farnesyl transferase inhibitors have been described in U.S. Pat. No. 5,756,528, U.S. Pat. No. 5,141,851, U.S. Pat. No. 5,817,678, U.S. Pat. No. 5,830,868, U.S. Pat. No. 5,834,434, and U.S. Pat. No. 5,773,455, all of which are incorporated herein by reference in their entirety. Among the farnesyl transferase inhibitors shown to be effective for inhibiting the transfer of the farnesyl moiety to Ras-related proteins are L-739,749 (a peptidomimetic analog of the C-A-A-X sequence), L-744,832 (a peptidomimetic analog of the C-A-A-X sequence), SCH 44342 (1-(4-pyridy-lacetyl)-4-(8-chloro-5,6 dihydro-IIH benzo[5,6]cyclohepta [1,2-b]pyridin-11-yhdene)piperidine), BZA-5B (a benzodiazepine peptidomimetic), FTI-276 (a C-A-A-X peptidomimetic), and B1086 (a C-A-A-X peptidomimetic). Administration of farnesyl transferase inhibitors (FTIs) is accomplished by standard methods known to those of skill in the art, most preferably by administration of tablets containing the FTI, and is expected to fall approximately within a range of about 0.1 mg/kg of body to weight to about 20 mg/kg of body weight per day.

In another embodiment, the additional agent comprises one or more inhibitor of geranylgeranyl-protein transferase (GGT) as have been described in U.S. Pat. No. 5,470,832 (Gibbs & Graham), which is incorporated herein by reference in its entirety. These compounds can be administered to an individual in dosage amounts of between 0.5 mg/kg of body weight to about 20 mg/kg of body weight. Alternatively, one or more inhibitors of isoprenylation, including farnesyl transferase (FT) inhibitors and/or geranylgeranyl transferase inhibitors (GGT) are administered to a patient.

In another embodiment, the additional agent comprises one or more toxins such as toxins A and B from *C. difficile* and *C. sordellii* lethal toxin (LT). In addition, Rac 1 and Rac2 can be inhibited when Rho is specifically ADP ribosylated by C3 enzyme, which is one of the botulinum toxins, and Staphylococcal toxin EDIN (Narumiya, S, and Morii, S., *Cell Signal*, 5, 9-19, 1993; Sekine, A. et al., *J. Biol. Chem.*, 264, 8602-8605, 1989, all of which are incorporated herein by reference in their entirety).

It is understood that appropriate doses of small molecule agents depends upon a number of factors within the ken of the ordinarily skilled physician, veterinarian, or researcher. The dose(s) of the small molecule will vary, for example, depending upon the identity, size, and condition of the subject or sample being treated, further depending upon the route by which the composition is to be administered, if applicable, and the effect which the practitioner desires the small molecule to have upon the nucleic acid or polypeptide of the preferred embodiments. Exemplary doses include milligram or microgram amounts of the small molecule per kilogram of subject or sample weight (e.g., about 1 microgram per kilogram to about 500 milligrams per kilogram, about 100 micrograms per kilogram to about 5 milligrams per kilogram, or about 1 microgram per kilogram to about 50 micrograms per kilogram. It is furthermore understood that appropriate doses of a small molecule depend upon the potency of the small molecule with respect to the expression or activity to be modulated. Such appropriate doses can be determined using the assays described herein. When one or more of these small molecules is to be administered to a subject (e.g., a human) in order to modulate expression or activity of a polypeptide or nucleic acid of the preferred embodiments, a physician, veterinarian, or researcher can, for example, prescribe a relatively low dose at first, subsequently increasing the dose until an appropriate response is obtained. In addition, it is understood that the specific dose level for any particular subject will depend upon a variety of factors including the activity of the specific compound employed, the age, body weight, general health, gender, and diet of the subject, the time of administration, the route of administration, the rate of excretion, any drug combination, and the degree of expression or activity to be modulated.

Suitable dosage ranges for the active compound can vary according to these considerations, but in general, the compounds are administered in the range of about 0.1 µg/kg-5 mg/kg of body weight; preferably the range is about 1 µg/kg-300 µg/kg of body weight; more preferably about 10 µg/kg-100 µg/kg of body weight. For a typical 70-kg human subject, thus, the dosage range is from about 0.7 µg-350 mg; preferably about 700 µg-21 mg; most preferably about 700 µg-7 mg. Dosages can be higher when the compounds are administered orally or transdermally as compared to, for example, i.v. administration. The compounds can be administered as a single bolus dose, a dose over time, as in i.v. or transdermal administration, or in multiple dosages.

The amount of active compound to be administered can vary according to the discretion of the skilled artisan. The amount of active compound to be administered to the recipient is within the ranges described above for stem cell mobilization. However, the administration of such amounts will vary according to the standards set forth by clinicians in the field of stem cell enhancement therapy. Administration should generally occur daily following chemotherapy or other treatment for 1 or more days, preferably daily or intermittently for up to 200 days.

The dosage regimen for increasing white blood cell survival following chemotherapy and mobilizing hematopoietic progenitor cells from bone marrow into peripheral blood with the active compounds is based on a variety of factors, including the type of injury, the age, weight, sex, medical condition of the individual, the severity of the condition, the route of administration, and the particular compound employed. Thus, the dosage regimen can vary widely, but can be determined routinely by a physician using standard methods. Dosage levels of the order of between 0.1 ng/kg and 10 mg/kg body weight of the active compounds per body weight are useful for all methods of use disclosed herein.

The treatment regime will also vary depending on the disease being treated, based on a variety of factors, including the type of injury, the age, weight, sex, medical condition of the individual, the severity of the condition, the route of administration, and the particular compound employed. For example, the active compounds are administered to an oncology patient for up to 30 days prior to a course of chemotherapy and for up to 60 days post-chemotherapy. The therapy is administered for 1 to 6 times per day at dosages as described above.

In a preferred embodiment, the active compound is administered subcutaneously. A suitable subcutaneous dose of the active compound is preferably between about 0.1 ng/kg and about 10 mg/kg administered twice daily for a time sufficient to increase mobilization of hematopoietic stem and progenitor cells from bone marrow into peripheral blood. This dosage regimen maximizes the therapeutic benefits of the treatments while minimizing the amount of agonist needed. Such an application minimizes costs as well as possible deleterious side effects.

For subcutaneous administration, the active ingredient can comprise from 0.0001% to 10% w/w, e.g. from 1% to 2% by weight of the formulation, although it can comprise as much as 10% w/w, but preferably not more than 5% w/w, and more preferably from 0.1% to 1% of the formulation. In a most preferred embodiment, subcutaneous administration of between about 1 to 1000 mg/kg/day of the active compounds is initiated at between one week before to one week after administration of a cancer therapy (e.g., a chemotherapeutic agent).

In another preferred embodiment, a subject undergoes repeated cycles of treatment according to the method disclosed herein. Preferably, a subsequent treatment cycle commences only after the administration of the compounds disclosed herein have been terminated and the subject's blood cell counts (e.g., white blood cell count) have returned to a therapeutically acceptable level (as determined by the attending veterinarian or physician), permitting the repeated chemotherapy.

In all of these embodiments, the compounds can be administered prior to, simultaneously with, or subsequent to chemotherapeutic exposure or any other therapeutic exposure.

The active compounds can be administered by any suitable route, including orally, parentally, by inhalation spray, rectally, or topically in dosage unit formulations containing conventional pharmaceutically acceptable carriers, adjuvants, and vehicles. The term parenteral as used herein includes, subcutaneous, intravenous, intraarterial, intramuscular, intrasternal, intratendinous, intraspinal, intracranial, intrathoracic, infusion techniques or intraperitoneally.

The active compounds can be made up in a solid form (including granules, powders or suppositories) or in a liquid form (e.g., solutions, suspensions, or emulsions). The compounds can be applied in a variety of solutions. Suitable solutions for use in accordance with the preferred embodiments are sterile, dissolve sufficient amounts of the peptide, and are not harmful for the proposed application. In this regard, the compounds disclosed herein are very stable but are hydrolyzed by strong acids and bases. The compounds are soluble in organic solvents and in aqueous solutions at pH 5-8.

The active compounds can be subjected to conventional pharmaceutical operations such as sterilization and/or can contain conventional adjuvants, such as preservatives, stabilizers, wetting agents, emulsifiers, buffers etc.

For administration, the active compounds are ordinarily combined with one or more adjuvants appropriate for the indicated route of administration. The compounds can be admixed with lactose, sucrose, starch powder, cellulose esters of alkanoic acids, stearic acid, talc, magnesium stearate, magnesium oxide, sodium and calcium salts of phosphoric and sulphuric acids, acacia, gelatin, sodium alginate, polyvinylpyrrolidine, and/or polyvinyl alcohol, and tableted or encapsulated for conventional administration. Alternatively, the compounds disclosed herein can be dissolved in saline, water, polyethylene glycol, propylene glycol, carboxymethyl cellulose colloidal solutions, ethanol, corn oil, peanut oil, cottonseed oil, sesame oil, tragacanth gum, and/or various buffers. Other adjuvants and modes of administration are well known in the pharmaceutical art. The carrier or diluent can include time delay material, such as glyceryl monostearate or glyceryl distearate alone or with a wax, or other materials well known in the art.

Kits

In a further aspect, kits are provided for increasing mobilization of hematopoietic stem and progenitor cells from bone marrow into peripheral blood, wherein the kits comprise an effective amount of the active compounds for increasing mobilization of hematopoietic progenitor cells from bone marrow into peripheral blood, and instructions for using the amount effective of active compound as a therapeutic. In a preferred embodiment, the kit further comprises a pharmaceutically acceptable carrier, such as those adjuvants described above. In another preferred embodiment, the kit further comprises a means for delivery of the active compound to a subject. Such devices include, but are not limited to syringes, matrical or micellar solutions, bandages, wound dressings, aerosol sprays, lipid foams, transdermal patches, topical administrative agents, polyethylene glycol polymers, carboxymethyl cellulose preparations, crystalloid preparations (e.g., saline, Ringer's lactate solution, phosphate-buffered saline, etc.), viscoelastics, polyethylene glycols, and polypropylene glycols. The means for delivery can either contain the effective amount of the active compounds, or can be separate from the compounds, that are then applied to the means for delivery at the time of use.

In another aspect a method is disclosed that comprises pharmaceutical compositions for increasing mobilization of hematopoietic stem and progenitor cells from bone marrow into peripheral blood following cancer therapy (e.g., chemotherapy), comprising the active compounds disclosed herein, an amount effective for decreasing the growth or neoplastic cells of an anti-neoplastic agent, and a pharmaceutically acceptable carrier. According to this aspect, any cytotoxic agent can be included in the pharmaceutical composition, including, but not limited to, cyclophosphamide, taxol, 5-fluorouracil, adriamycin, cisplatinun, methotrexate, cytosine arabinoside, mitomycin C, prednisone, vindesine, carbaplatinum, and vincristine. The cytotoxic agent can also be an antiviral compound that is capable of destroying proliferating cells.

The compositions and preparations described preferably contain at least 0.1% of active compound. The percentage of the compositions and preparations can, of course, be varied, and can contain between about 2% and 60% of the weight of the amount administered. The amount of active compounds in such pharmaceutically useful compositions and preparations is such that a suitable dosage will be obtained.

One embodiment also pertains to kits useful in the methods. Such a kit contains an appropriate quantity of active compound, and other components useful for the methods. For example, a kit used to facilitate in vivo expansion of hematopoietic stem cells contains an appropriate amount of the active compound to facilitate mobilization, as well as an amount of the active compound to enhance the expansion of the stem cells by growth factors. Such a kit can also contain an appropriate amount of a growth factor.

The methods, kits, and pharmaceutical compositions of the present invention, by increasing white blood cell survival following chemotherapy and mobilizing hematopoietic progenitor cells from bone marrow into peripheral blood, significantly enhance the utility of presently available treatments for clinical chemotherapeutic treatments.

The following references, to the extent that they provide exemplary procedural or other details supplementary to those set forth herein, are specifically incorporated herein by reference in their entirety where permitted: U.S. Pat. Nos. 6,410,323; 6,191,147; 6,184,203; 5,863,532; 5,574,025; 5,470,832; 5,244,916; 5,043,268, and U.S. provisional patent applications 60/523,599 (GTPase Inhibitors and Methods of Use), filed Nov. 20, 2003; 60/527,589 (Methods of Enhancing Stem Cell Engraftment), filed Dec. 5, 2003; 60/494,719 (Chimeric Peptides for the Regulation of GTPases), filed Aug. 13, 2003; 61/069,073 (Mobilization of Hematopoietic Stem Cells), filed Mar. 12, 2008; U.S. patent application publications 20050142103, filed Aug. 12, 2004; 20050069553, filed Mar. 31, 2005; 20050238666, filed Dec. 3, 2004; 20060004032, filed Nov. 19, 2004; 20070155766, filed Jul. 21, 2006; and 20060135532, filed Nov. 18, 2005.

In addition, information regarding procedural or other details supplementary to those set forth herein, are described in cited references specifically incorporated herein by reference.

The various methods and techniques described above provide a number of ways to carry out the invention. Of course, it is to be understood that not necessarily all objectives or advantages described can be achieved in accordance with any particular embodiment described herein. Thus, for example, those skilled in the art will recognize that the methods may be performed in a manner that achieves or optimizes one advantage or group of advantages as taught herein without necessarily achieving other objectives or advantages as may be taught or suggested herein.

Furthermore, the skilled artisan will recognize the interchangeability of various features from different embodiments. Similarly, the various features and steps discussed above, as well as other known equivalents for each such feature or step, can be mixed and matched by one of ordinary skill in this art to perform methods in accordance with principles described herein.

Although the invention has been disclosed in the context of certain embodiments and examples, it will be understood by those skilled in the art that the invention extends beyond the specifically disclosed embodiments to other alternative embodiments and/or uses and obvious modifications and equivalents thereof. Accordingly, the invention is not intended to be limited by the specific disclosures of preferred embodiments herein, but instead by reference to claims attached hereto.

The following examples provide illustrations of some of the embodiments described herein but are not intended to limit the invention.

EXAMPLE 1

CASIN is a Cdc42 Activity-Specific Inhibitor in Murine Fibroblasts and Hematopoietic Progenitors A lead small molecule inhibitor was identified termed CASIN, which stands for Cdc42 activity specific inhibitor, its inactive analog being used as a control (FIG. 1a). In a nucleotide exchange experiment where Cdc42 was incubated in the presence of CASIN and the fluorescent nucleotide analogue mant-GDP, and launched the exchange reaction with Cdc42 specific GEF intersectin, CASIN led to a dose-dependent inhibition of the association of mant-GDP with Cdc42 induced by intersectin (FIG. 1b). However, CASIN did not affect Tiam or Large induced nucleotide exchange of mant-GDP with Rac or Rho respectively (FIG. 6). For example, even at 10 times the $IC_{50}$ of Cdc42, a 50% inhibition of the association of mant-GDP with Rac or Rho was not achieved. These data demonstrate that CASIN interferes with the process of nucleotide exchange on Cdc42 specifically.

Figure 1C:
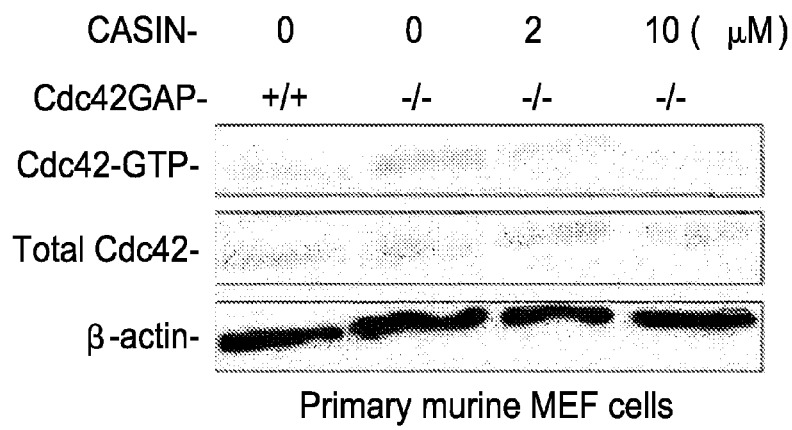
FIG. 1. Identification of CASIN as a Cdc42 activity-specific inhibitor in murine fibroblasts and hematopoietic cells. (a) Molecule structure of CASIN and its inactive analog. (b) Association of mant-GDP with Cdc42 induced by intersectin was inhibited by CASIN dose-dependently. (c) Cdc42 activity was inhibited by CASIN with a does-dependent pattern. (d) CASIN specifically suppressed Bradykinin-induced filopodia formation in Swiss 3T3 cells, while PDGF and LPA still efficiently induced formation of lamellipodia and stress fiber formation respectively in the presence of CASIN. (e) Effects of CASIN on Cdc42, Rac1, and RhoA were shown in murine LDBM cells by Rho-GTPase effector pull-down assays, and the Cdc42 activity inhibition was quantified to the right.
Figure 1D:
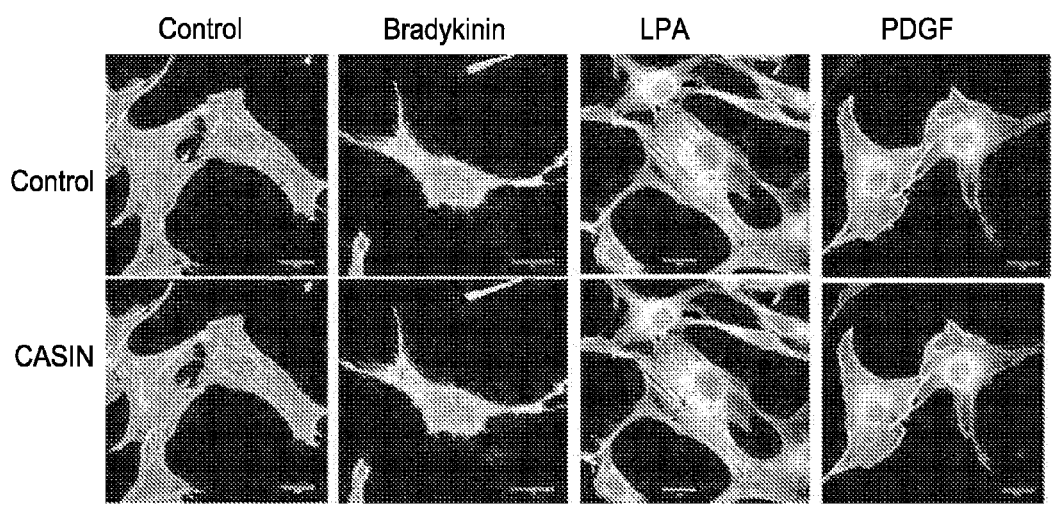

In primary murine fibroblasts, CASIN dose-dependently inhibited the Cdc42 activity in Cdc42GAP$^{-/-}$ cells where Cdc42 is highly active in comparison to Cdc42GAP$^{+/+}$ cells (FIG. 1c). To investigate the Cdc42-dependent cytoskeleton rearrangement, Swiss 3T3 fibroblasts were used since it was abundantly elaborated in Swiss 3T3 fibroblats that bradykinin induces actin filopodia formation through activating Cdc42, whereas PDGF activates Rac1 and induces Rac-mediated membrane lamellipoidia, and LPA responsible for RhoA activation, eliciting RhoA-medicated formation of actin stress fibers and focal adhesion assembly (Ridley, A. J. et al. Cell 70, 401-410 (1992); Ridley, A. J. et al. Cell 70, 389-399 (1992); Kozma, R. et al. Mol Cell Biol 15, 1942-1952 (1995)). As shown in FIG. 1d, 15 min stimulation with bradykinin, PDGF, and LPA efficiently induced formation of filopodia, lamellipodia, and actin stress fiber formation in serum-starved Swiss 3T3 cells, respectively. However, in the presence of CASIN, while PDGF and LPA still induced their respective changes in actin reorganization, bradykinin-induced filopodia formation was suppressed completely, demonstrating CASIN specifically blocks bradykinin induction of filopodia formation.

Figure 1E:
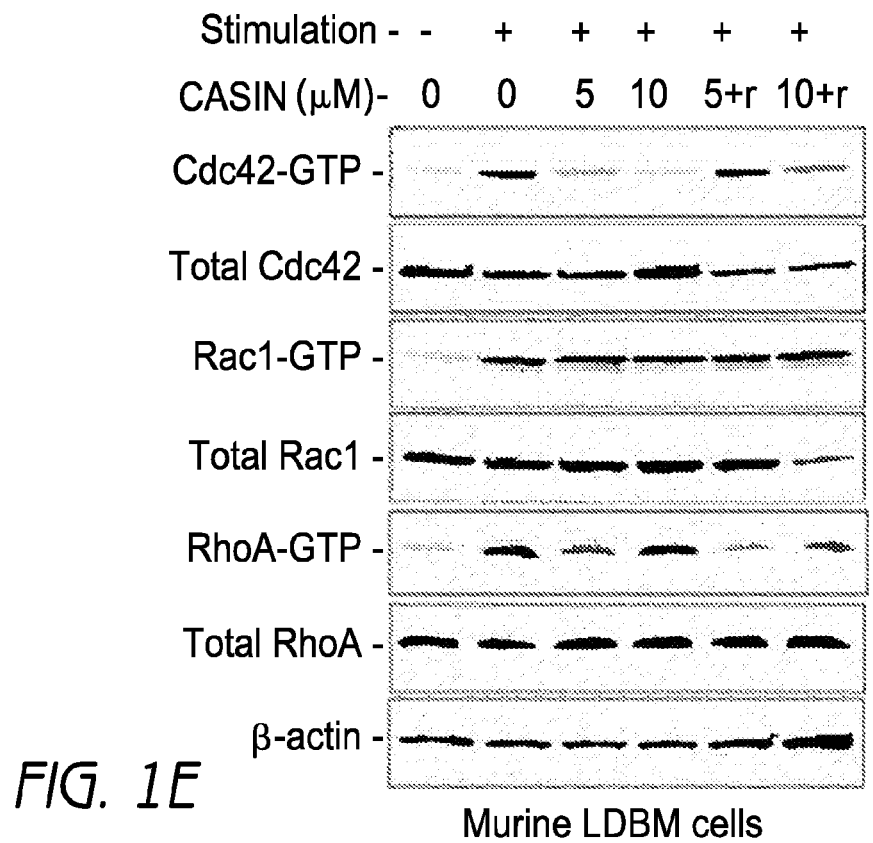
Figure 1F:
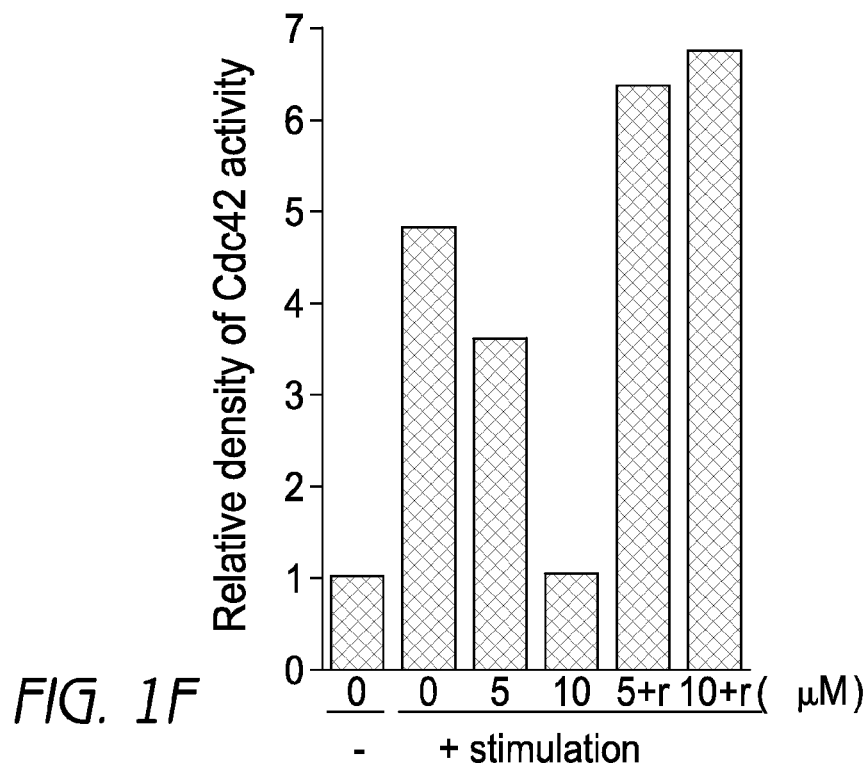

To examine if CASIN can specifically and reversibly inhibit Cdc42 activity in murine LDBM cells in which hematopoietic progenitors were enriched, Rho GTPase effector pull-down assays were carried out (FIG. 1e). Under mixed cytokine stimulation, Cdc42 activity increased significantly. Pre-treatment of cells with CASIN at doses of 5 and 10 μM led to a dose-dependent inhibition of the Cdc42 activity. Removal of CASIN by a pre-wash restored the Cdc42 activity in response to cytokine stimulation, indicating that the CASIN effect is reversible. Intriguingly, parallel pull-down assays on Rac1 and RhoA activities found no effects from the CASIN treatment, demonstrating that CASIN is specific towards Cdc42 activity.

EXAMPLE 2

Figure 2A:
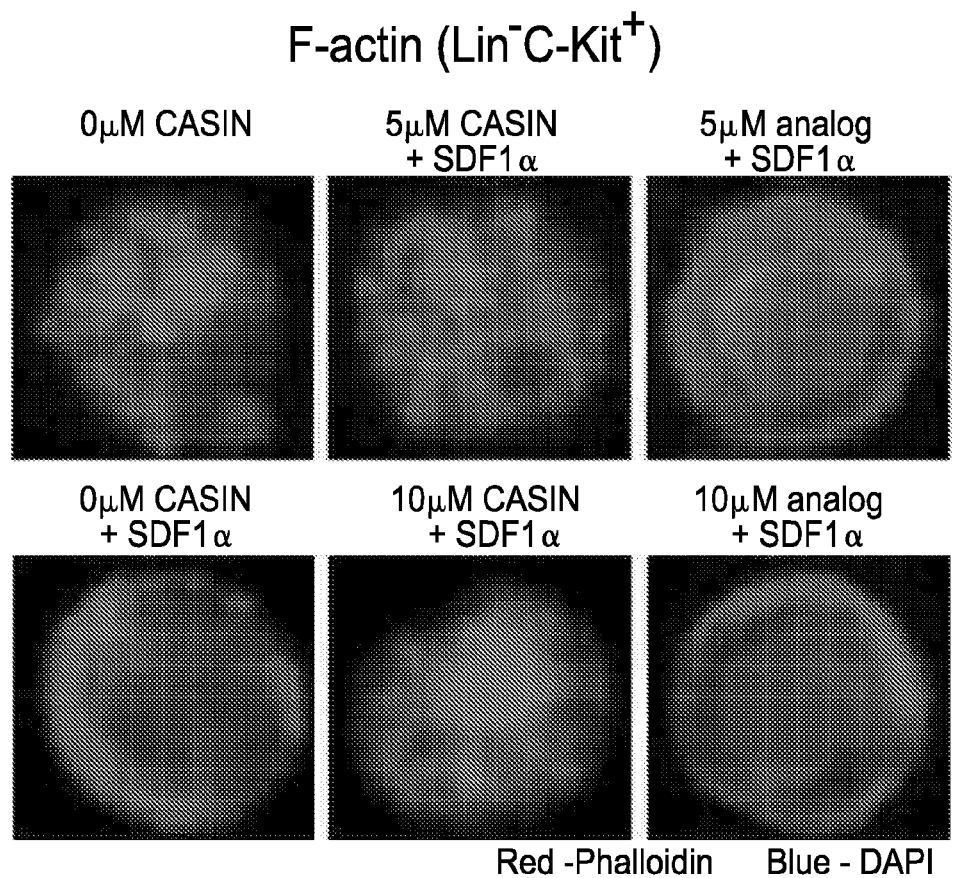
FIG. 2. CASIN caused transient defects in adhesion, migration, and F-actin polymerization in murine hematopoietic progenitors. (a) Immunofluoresence staining on F-actin showed CASIN impaired F-actin reorganization on the cortical surface of sorted Lin⁻c-kit⁺ cells, while CASIN inactive analog did not. (b) Consistently, flow cytometry on F-actin by using column-selected Lin⁻ BM cells showed that mean fluorescence intensity (MFI) of F-actin reorganization was dampened dose-dependently. (c) Western blot showed Cdc42 was completely deleted post pIpC injection in the LDBM cells isolated. (d) CASIN does not affect the proliferation of $Cdc42^{+/+}$ progenitors, nor show any side effect on the $Cdc42^{-/-}$ cells. (e) In a CFU-adhesion assay of LDBM cells, CASIN can dose-dependently inhibit adhesion of colony-forming progenitors to fibronectin surface in $Cdc42^{+/+}$ cells while not in $Cdc42^{-/-}$ cells. (f) CASIN showed similar inhibitory effect on migration of colony-forming progenitors in Cdc42$^{+/+}$ cells while not in the Cdc42$^{-/-}$ cells.
Figure 2B:
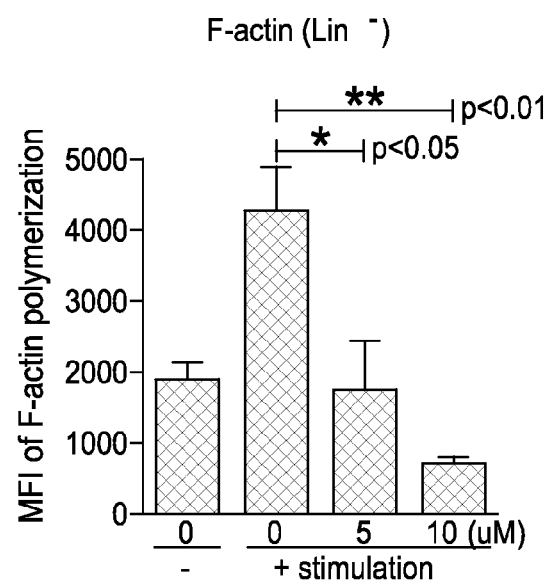
Figure 2C:
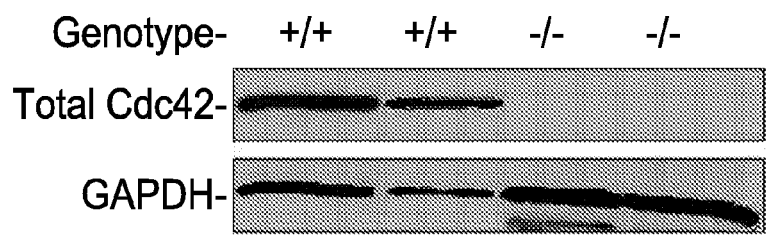
Figure 2D:
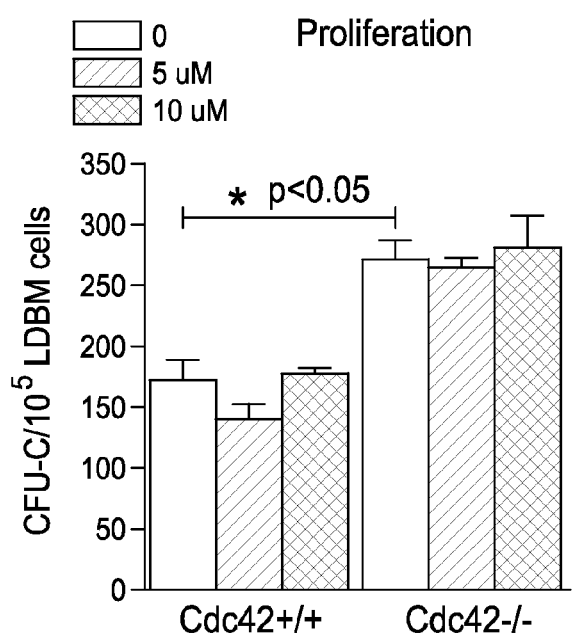
Figure 2E:
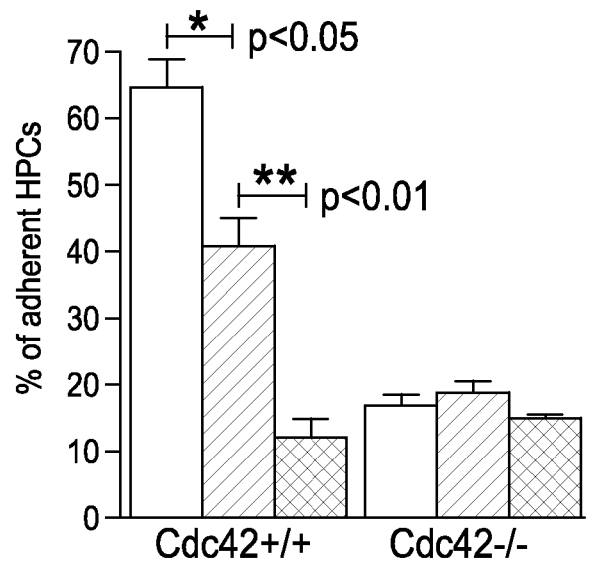
Figure 2F:
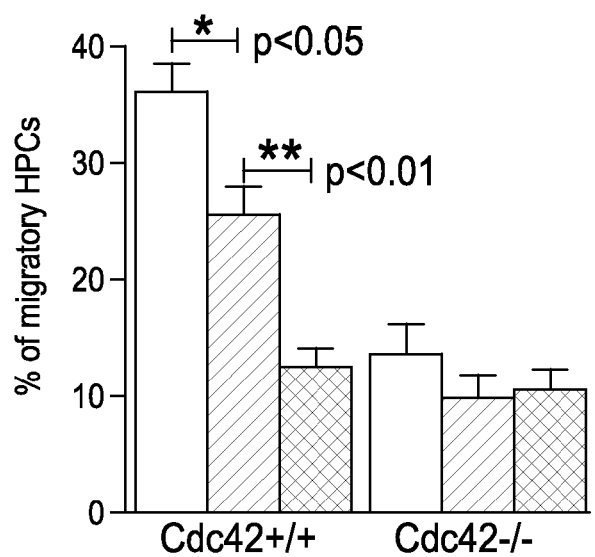
Figure 7D:
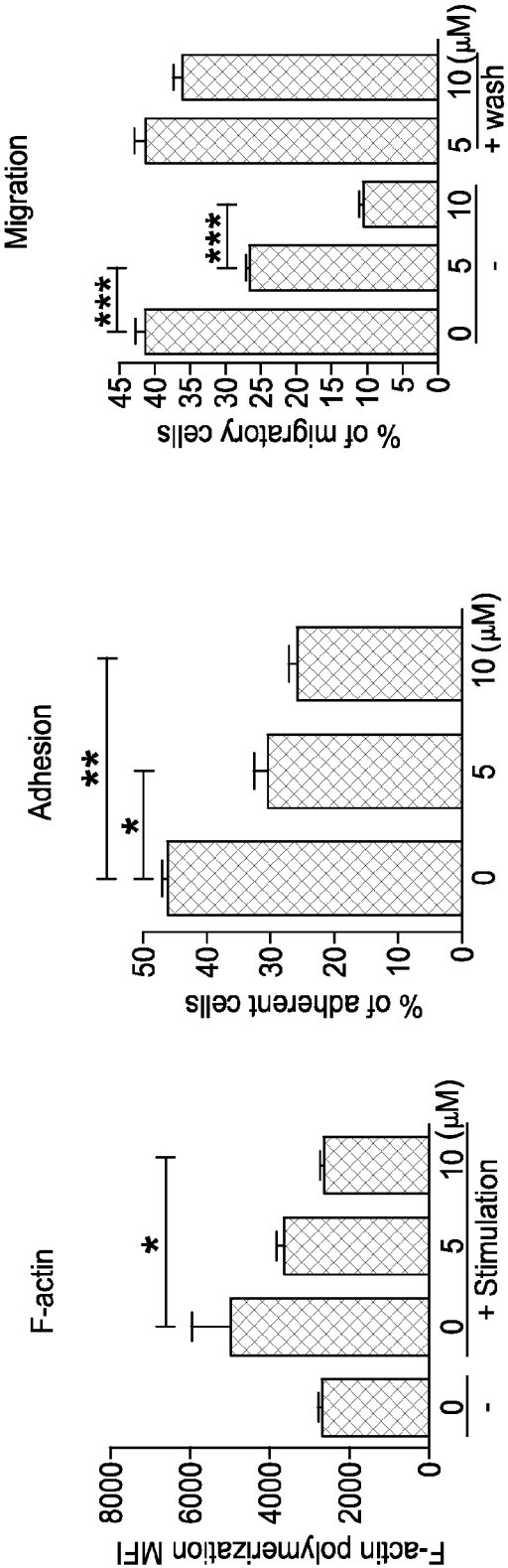
FIG. 7. CASIN impaired Cdc42-related cellular functions in eluding adhesion, migration, and F-actin reorganization in 32D cells. (a) MFI by flow cytomety indicative of F-actin polymerization in 32D cells was inhibited by gradient CASIN treatments. (b) Adhesion of 32D progenitors via CH296 was inhibited dose-dependently by CASIN pre-treatments. (c) Migration of 32D progenitors towards SDF-1α was inhibited by CASIN pre-treatments with a dose-dependent pattern. (d) CASIN treatment in 32D progenitors led to dampened phosphorylation of WASP, while phosphorylation of PAK1 or GSK-313.

CASIN Cause Transient Deficiencies in Adhesion, Migration, and F-actin Polymerization in Murine Progenitors To shed light on potential roles of CASIN in HSPC mobilization, the effects of CASIN on Cdc42-related cellular functions was studied, including adhesion, migration, and F-actin polymerization of progenitor cells in 32D myeloid progenitors. FACS analysis on F-actin stained with Phalloidin-Rhodamine showed that CASIN significantly dampened F-actin reorganization stimulated by SDF1α in 32D progenitors with a dose-dependent pattern (FIG. 7a). In an adhesion experiment of 32D progenitors to fibronectin (FN) fragment CH296 which mediates cell adhesion via α4β1, the percentages of adherent 32D cells to CH296 were significantly reduced dose-dependently by gradient CASIN treatments (FIG. 7b). In a transwell migration assay, CASIN led to significantly reduced migration of 32D progenitor cells towards SDF1α gradient with a dose-dependent manner (FIG. 7c). Secondarily, in the double-sorted Lin$^-$c-Kit$^+$ BM progenitors Immunofluorescence on F-actin with Rhodamine-Phalloidin showed F-actin is punctuated and scattered on the cells in the absence of SDF-1α. SDF-1α stimulation causes a reorganization of F-actin into a cortical ring around the cells. With CASIN pre-treatment at 5 or 10 μM the cells lost their capacities to reorganize F-actin into the cortical actin ring in response to SDF-1α. Remarkably, treatment of the cells with an inactive CASIN analog does not affect the SDF-1α mediated cortical actin reorganization (FIG. 2a). Consistently, FACS analysis on F-actin using column-selected Lin$^-$ BM cells showed similarly that CASIN impaired F-actin reorganization in response to SDF-1α with a dose-dependent pattern (FIG. 2b). Thirdly, to gain further insight into cellular specificity and efficacy of CASIN, and also to rule out possible toxic effects by CASIN, Cdc42-involved BM progenitor cell functions were examined, including proliferation, adhesion, migration, and F-actin polymerization, in $Cdc42^{+/+}$ cells in parallel with $Cdc42^{-/-}$ cells. Cdc42 was completely deleted in the LDBM cells used for the assays as shown in FIG. 2c. In line with additional studies in a Cdc42 conditional knockout mouse model as described herein, $Cdc42^{-/-}$ LDBM cells have increased CFU-forming progenitors compared to those of $Cdc42^{+/+}$. Advantageously, CASIN did not affect the proliferation of WT progenitors, nor showed any side effect on the KO cells (FIG. 2d) as compared with the Cdc42 conditional knockout mouse. For example, CASIN did not cause myeloproliferative disorders (MPDs) or hyperactivation as compared with the Cdc42 conditional knockout mouse. In a CFU-adhesion assay of LDBM cells, CASIN dose-dependently inhibited adhesion of colony-forming progenitors to fibronectin surface, to an extent mimicking $Cdc42^{-/-}$ cells, while CASIN did not have additive effects on the adhesion activity of $Cdc42^{-/-}$ cells (FIG. 2e). The migration activity of progenitors towards SDF-1α showed a similar dose-dependent effect of CASIN inhibition to that of adhesion activity in the $Cdc42^{+/+}$ cells, while CASIN did not affect the directional migration capacity of $Cdc42^{-/-}$ cells (FIG. 2f). Therefore, these experiments demonstrate that CASIN works specifically in inhibiting Cdc42-mediated cellular activities such as actin polymerization, adhesion, and directional migration.

EXAMPLE 3

CASIN Induces Mobilization of Murine HPCs and HSCs in Mice

Figure 3B:
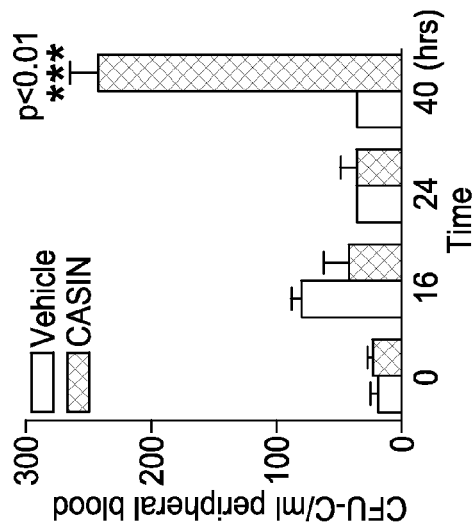
FIG. 3. CASIN efficiently caused the mobilization of HPCs and HSCs in C57Bl/6 mice. (a) Experimental setup of CFU-C assays to examine numbers of HPCs in PB from control or CASIN treatment group. (b) Numbers of colony-forming cells per ml blood over time in CASIN treated mice in comparison to vehicle control. (c) Experimental setup of serial transplantations using PB harvested from CASIN-treated mice by 40 hrs. (d) PB reconstitution of donor-derived cells in the primary recipient from the first month through the third month. (e) Multi-lineage differentiation of donor-derived cells in both PB and BM. (f) Engraftment of donor derived cells in BM from primary recipients through tertiary recipients. (g) Relative number changes of immunophenotypically defined multi-compartments of HSPCs after CASIN treatment in comparison to vehicle control. (h) CFU numbers per $10^6$ splenocytes post CASIN administration in comparison to that of vehicle control. (i) CFU numbers per $10^6$ hepatocytes post CASIN administration in comparison to that of vehicle control.
Figure 3A:
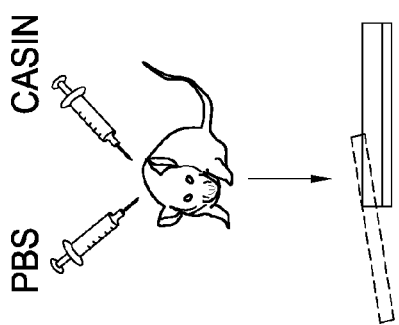
Figure 3C:
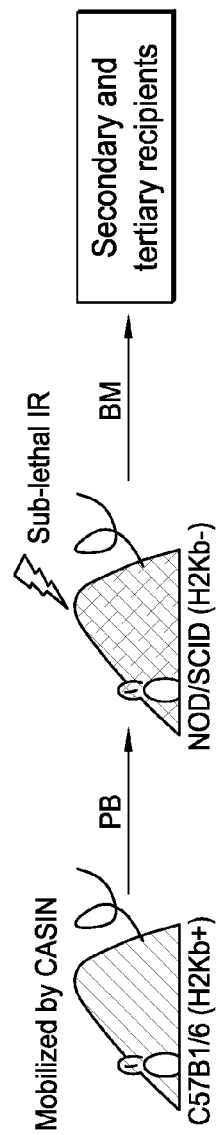

As demonstrated in experiments described herein, deletion of Cdc42 in a conditional-knockout mouse model led to massive egress of HSC/Ps to the peripheral blood associated with impaired adhesion, migration, and F-actin reorganization. Whether CASIN administration can induce mobilization of HSC/Ps to peripheral blood of C57Bl/6 mice, mimicking the phenotype observed in Cdc42 conditional knockout mice, was evaluated. First of all, mobilization of hematopoietic progenitor cells was examined by CFU-C assays functionally (FIG. 3a). Intraperitoneal injection of CASIN at dose of 2.4 mg/Kg induced more than six-fold mobilization of colony-forming progenitors to the peripheral blood by 40 hrs post CASIN administration in comparison to vehicle control group (FIG. 3b). Rho GTPase pull-down assay showed by the time Cdc42 activity was really down in the LDBM cells accordingly (FIG. 8a). In C57Bl/6 mice both G-CSF and AMD3100 can mobilize colony-forming progenitors in line with previous studies (Roberts, A. W. et al. Blood 89, 2736-2744 (1997); de Haan, G. et al. Br J Haematol 110, 638-646 (2000)), indicating combination of CASIN with either of them would be a way to solve the limitations of utilities in G-CSF or AMD3100 (Roberts, A. W. et al. Stem Cells 13, 512-516 (1995)) (FIG. 8b). Secondarily, to further explore the ability of CASIN to mobilize LT-HSC which is crucial for long-term repopulation of the mobilized cells, serial transplantations were carried out, where 20 million PB from CASIN-mobilized C57Bl/6 mice was transplanted into primary recipient of NOD/SCID mice, and subsequent secondary and tertiary transplants were finished as well using prior BMs (FIG. 3c). Donor chimerisms were assessed by using $H2K^b$ congenic marker which is positive for donors of C57Bl/6 strain and negative for recipients of NOD/SCID strain. At 1-3 mo post transplantation, the donor-derived cells reconstituted considerable percentages of total PB of the primary recipient (FIG. 3d), and the engrafted donor cells had undergone multi-lineage differentiations in both BM and PB of the primary recipients (FIG. 3e). In the BMs of primary through tertiary transplantation, engraftment of donor-derived cells was detected, indicating that CASIN mobilized peripheral blood has long-term reconstitution capacity (FIG. 3f). Therefore, the studies show CASIN can efficiently mobilize colony-forming hematopoietic progenitors and LT-HSCs with self-renewal and multi-lineage differentiation capacity. Thirdly, to further investigate the potential of CASIN to vacate the BM niche after mobilization, six-color staining of the BM cells was performed from C57Bl/6 mice with or without CASIN treatment followed by FACS analysis. The number of genotypic HSCs ($IL7Ra^-Lin^-Sca-1^+c-Kit^+$) in the BM decreased significantly after CASIN injection, correlating with an increased level of the progenitor cells found in spleen and liver detected by CFU-C assays (FIG. 3g, h, i). Therefore, a transient decrease in BM and a concomitant increase in peripheral organs of HSCs would be beneficial to facilitating the subsequent HSC transplantation.

EXAMPLE 4

Figure 4C:
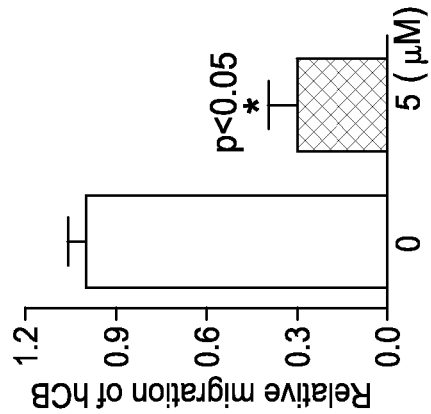
FIG. 4. CASIN can mobilize human CD45$^+$ hematopoietic cells in CD34$^+$ HCB-xenografted NOD/SCID mouse model, associated with CASIN-induced deficiencies in F-actin reorganization, adhesion, and migration. (a) SDF-1α induced F-actin polymerization over time without or with gradient CASIN treatment, determined by MFI using FACS analysis. (b) Relative adhesion of CD34$^+$ HCB cells in the presence of CASIN at dose of 5 μM in comparison to that of control. (c) relative migration of human CD34$^+$ cord blood cells in the presence of CASIN at dose of 5 μM in comparison to that of control. (d) Percentage changes of human CD45$^+$ hematopoietic cells in PB normalized to their respective basal levels, determined by FACS analysis on PB along time after CASIN treatment. (e) Average percentage changes of human CD45$^+$ hematopoietic cells in PB determined by FACS analysis on PB along time after CASIN treatment.
Figure 4B:
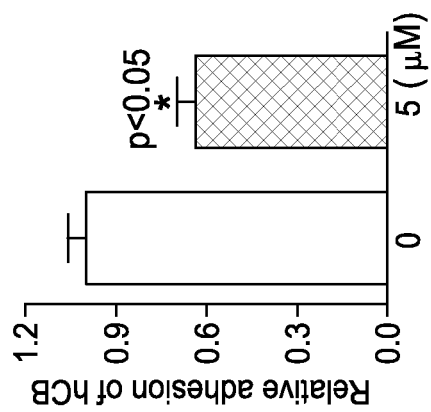
Figure 4A:
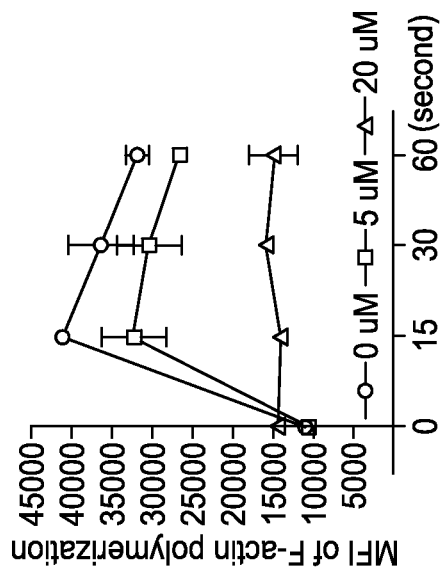
Figure 4E:
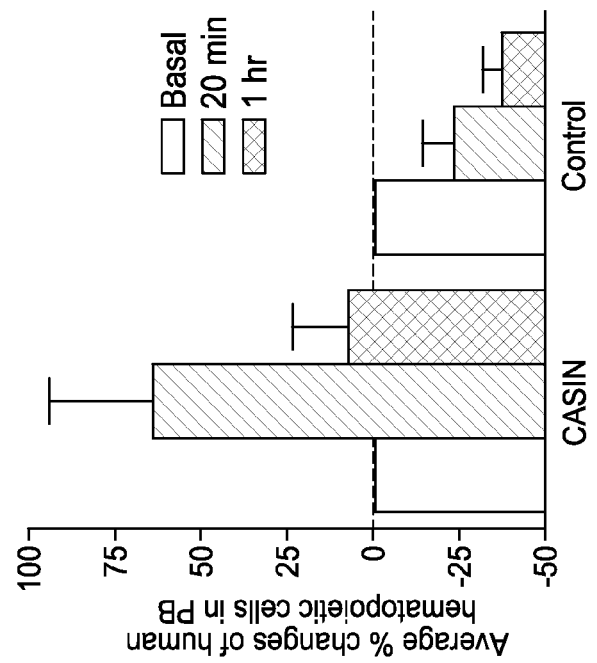
Figure 4D:
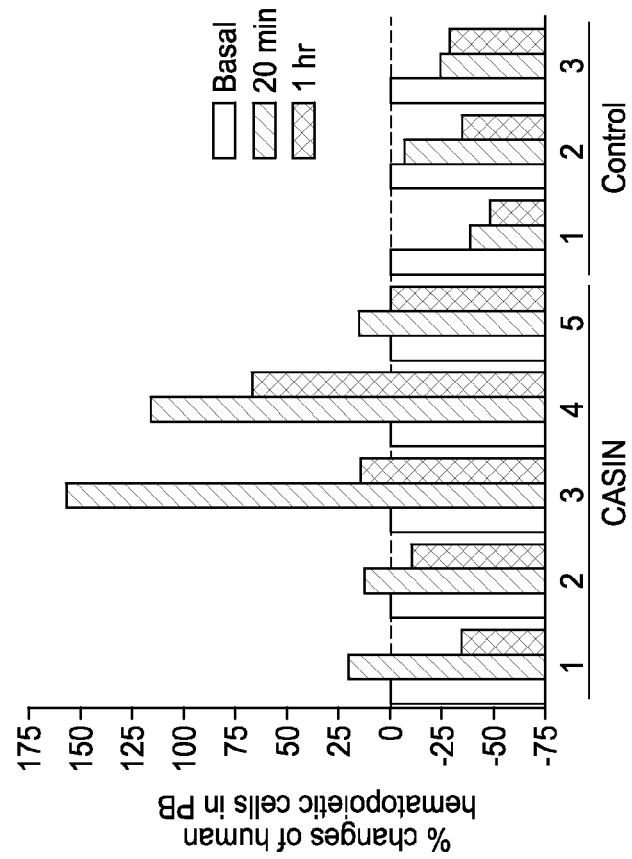
Figure 5B:
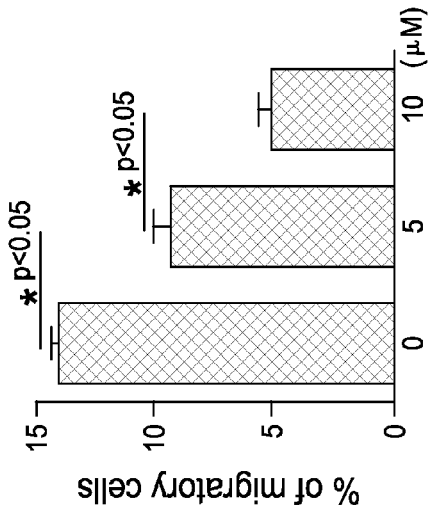
FIG. 5. CASIN can mobilize leukemia initiating cells (LICs) in human MA93NRas myeloid leukemia line xenografted NOG mouse model, associated with deficiencies in F-actin polymerization and migration. (a) SDF-1α induced F-actin polymerization without or with gradient CASIN pretreatments was determined by MFI using FACS analysis. (b) Migration of leukemia cells towards SDF-1α without or with CASIN pre-treatment at doses of 5 and 10 μM was determined by transwell assays. (c) Adhesion of leukemia cells via CH296 without or with CASIN pre-treatment at doses of 5 and 10 μM was examined. (d) CASIN precipitated leukemia cells to apoptosis after 24 hrs' CASIN pre-treatment by FACS analysis. (e) Percentage changes of human leukemia initiating cells in PB normalized to their respective basal levels, determined by FACS analysis on PB along time after CASIN treatment. (f) Average percentage changes of human LICs in PB determined by FACS analysis on PB along time after CASIN treatment.
Figure 5D:
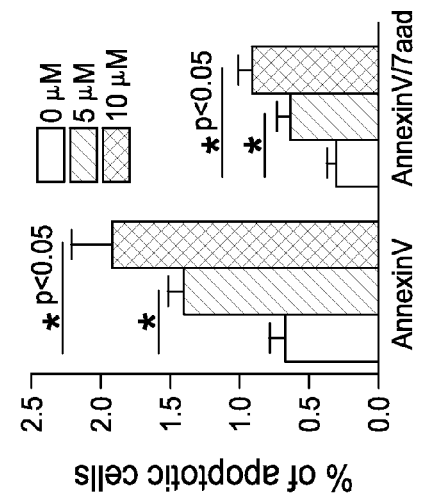
Figure 5A:
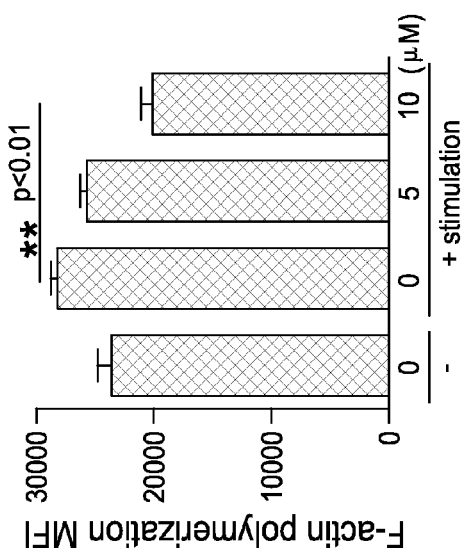
Figure 5C:
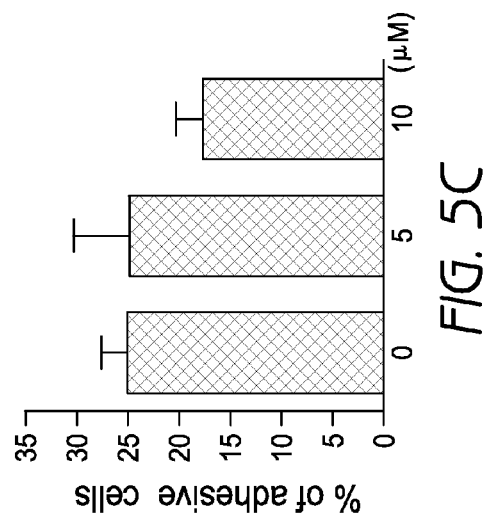
Figure 5F:
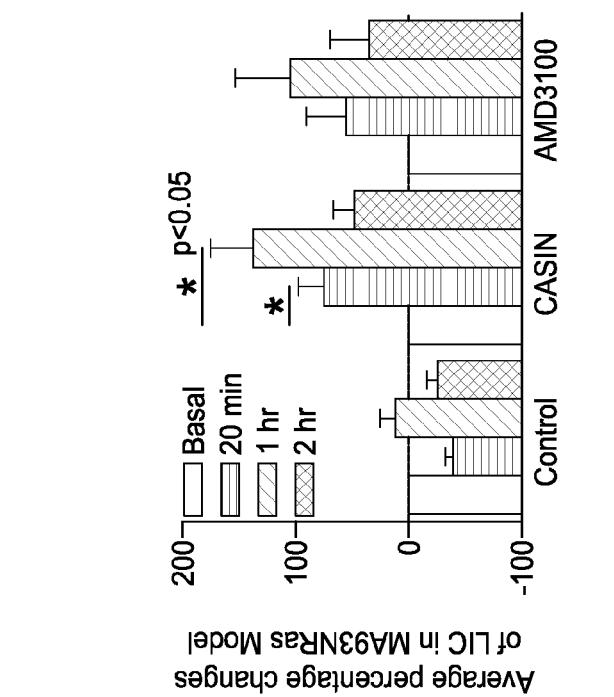
Figure 5E:
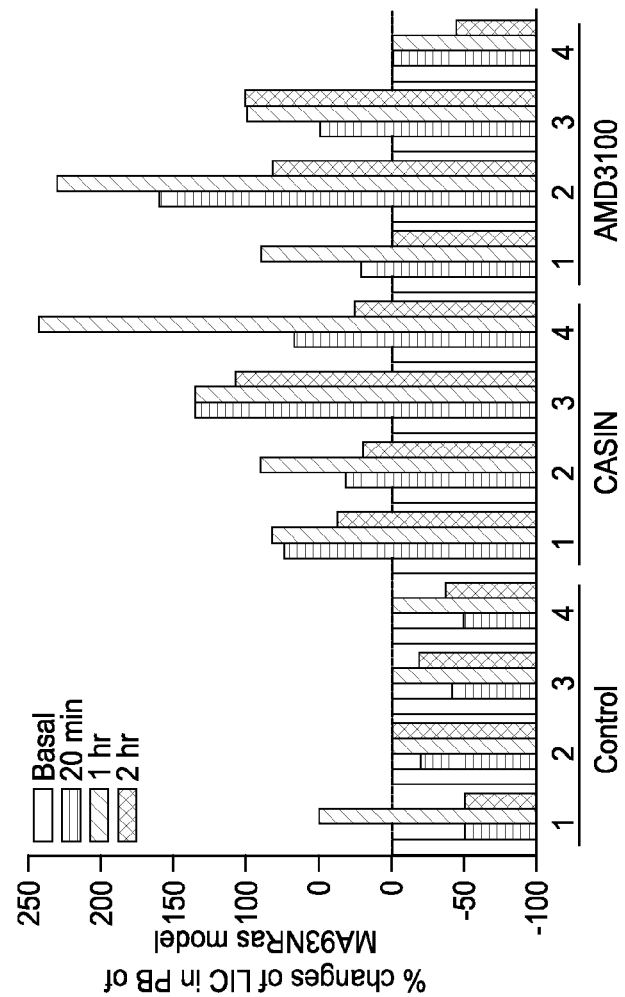
Figure 9B:
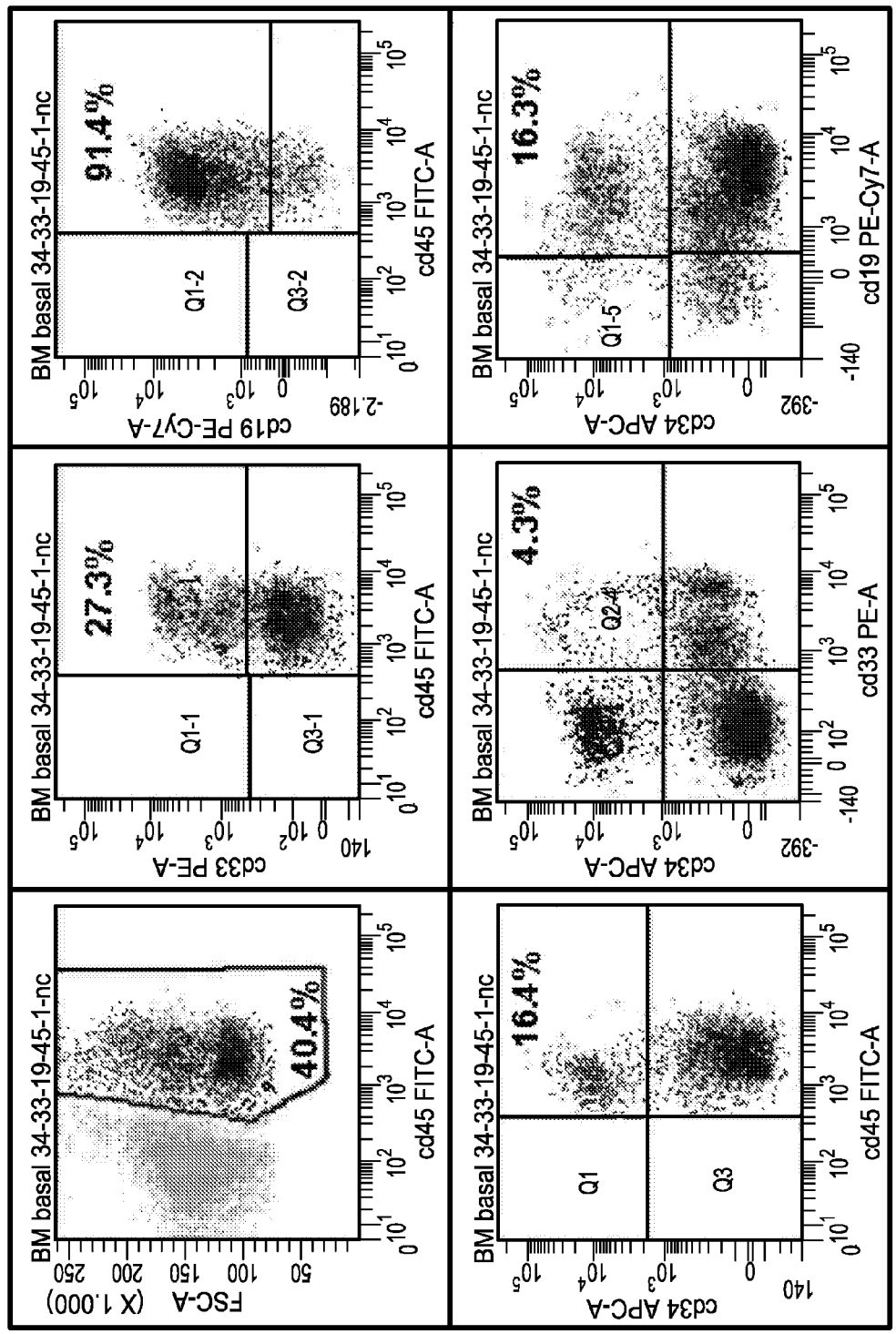
FIG. 9. CASIN efficiently inhibited Cdc42 activity in human CD34$^+$ HCB cells. (a) Cdc42 activities were decreased by CASIN treatments, while Rac1 activity was not affected. (b) Multi-lineage engraftment of HCB in NOD/SCID recipient BMs was determined by flow cytometry analyses.

CASIN Causes Mobilization of Human Hematopoietic Cells in a NOD/SCID-hCB Model To begin to study potential utility of CASIN in human hematopoietic stem cell mobilization, a series of cellular assays were carried out to determine the effects on human $CD34^+$ umbilical cord blood cells (HCBs). Rho GTPase effector pulldown experiments showed CASIN can specifically inhibit Cdc42 activity without affecting the closely related Rac1 activity (FIG. 9). Flow cytometry analysis demonstrated that CASIN inhibited F-actin polymerization of these human progenitors dose-dependently (FIG. 4a). Similarly, CASIN significantly dampened the adhesion and migration activities of human progenitors at the dose of 5 μM (FIG. 4b, c). These results indicate that CASIN could be applied to human hematopoietic stem and progenitor cells. The effects of CASIN on human hematopoietic cell mobilization was therefore tested using a well established preclinical in vivo model (NOD/SCID-Hcb) of human hematopoietic function, where fresh $CD34^+$ hCB cells were transplanted into sub-lethally irradiated NOD/SCIDS by intrafemoral injection, and repopulated and maintained human hematopoietic reconstitution in the bone marrow of NOD/SCID recipient mice (FIG. 9b, FIG. 11) (Larochelle, A. et al. Nat Med 2, 1329-1337 (1996); Bhatia, M., et al. Proc Natl Acad Sci USA 94, 5320-5325 (1997)). Intravenous injections of CASIN were applied when human cells were well engrafted in the NOD/SCID recipients. As shown in FIG. 4d, e, by 20 min post CASIN administration, there was significant amount of human $CD45^+$ hematopoietic cells mobilized to the peripheral blood for each single mouse in the CASIN group, while vehicle injections did not cause any mobilization as a comparison. Therefore, the data clearly demonstrate the potential utilities of CASIN as a mobilizer in human, similar to effects observed in mice.

EXAMPLE 5

Figure 10:
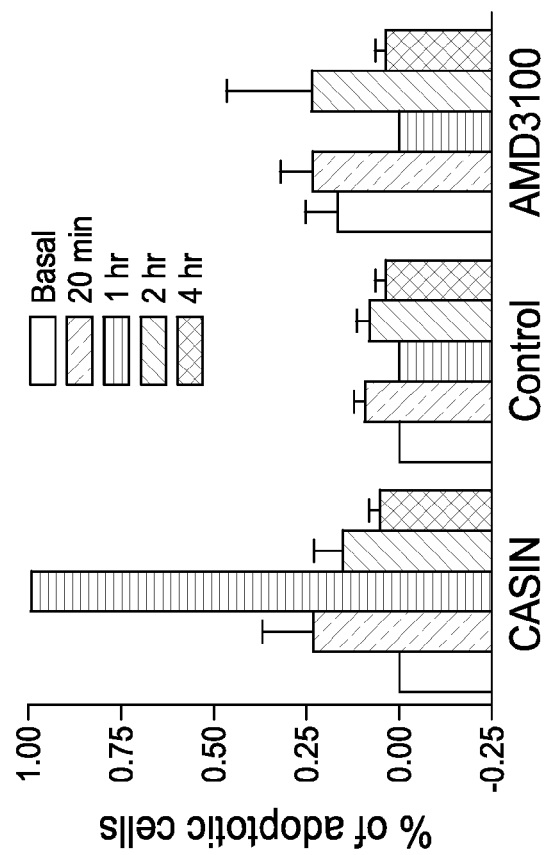
FIG. 10. In vivo CASIN short-term treatment did not elicit apoptosis of leukemia cells in the human AML mouse model.

CASIN Causes Mobilization of Human Leukemia Initiating Cells (LICs) in a Xenografted Human Leukemia Mouse Model Like normal HSCs, their malignant counterpart, leukemia initiating cells (LICs) reside in their BM niches that provide the structural and physiological conditions supporting their survival and growth. LICs are resistant to traditional chemotherapy by interacting with their BM microenvironment, which are the culprits of leukemia relapses after a period of remission induced by chemotherapy. Detachment of LICs from their niche by CASIN would be a valuable supplementary therapy to the traditional cancer therapies (e.g., chemotherapies). First of all, in vitro effects of CASIN were examined in adhesion, migration, and F-actin polymerization of LICs, each of which is independently important for the retention of LICs in BM niches. Retroviral transduction of an MLL-AF9 fusion cDNA together with N-Ras oncogene into normal human CD34$^+$ cord blood cells led to the establishment of cultures of N-Ras-MA93 cells that can initiate acute myeloid leukemia in NOG mice. These studies showed that, while the adhesion capacity was not affected significantly, CASIN significantly impaired the directional migration and F-actin reorganization capacities of N-RasMA93 cells in vitro, thus putting forth potential mobilization effects of CASIN on those LICs (FIG. a, b, c). To address it, a human AML model was set up by transplanting N-RasMA93 cells into NOG mice intravenously. CASIN was injected intravenously after leukemia was developed in this model, and found that by 20 min post injection, CASIN efficiently mobilized the LICs to the peripheral blood transiently, while the vehicle group in parallel did not show any mobilization (FIG. e, f). Moreover, short-term in vivo administration of CASIN did not elicit significant apoptosis or cell death (FIG. 10). The data suggest CASIN may be able to sensitize the LICs to traditional cancer therapies (e.g., chemotherapies or radiotherapies) by breaking up their interactions with the BM niches.

The example below describes in greater detail some of the materials and methods used in Examples 1-5.

EXAMPLE 6

Animals

C57BL/6, NOD/SCID, NOD/SCID-SGM3 and NOD/SCIDγC−/− (NOG) were in house bred in the animal barrier facility of Cincinnati Children's Hospital Medical Center (CCHMC) and used at the age of 6-8 weeks old. Cultured N-RasMA93 cells were injected into NOD/SCIDγC−/− mice by tail vein. Freshly thawed CD34$^+$ hCB cells were transplanted into NOD/SCID mice by intrafemoral injection.

CASIN

The Cdc42 activity-specific inhibitor CASIN and its inactive analog referred to in the literature as Pirl1 related compound 2 and 7 respectively (Peterson, J. R. et al. Chem Biol 13, 443-452 (2006)) were synthesized by Chembridge Corporation. The inhibitors were purified to >99% by high-performance liquid chromatography. CASIN inhibited PIP2 induced F-actin assembly in xenopus egg extracts with an IC50 (dose required to inhibit the maximum polymerization rate by 50%) of 2 μM, while its analog with that of 99 μM (Peterson, J. R. et al. Chem Biol 13, 443-452 (2006)). CASIN was formulated in DMSO at concentration of 10 mM for in vitro studies, and in 15% ethanol at 0.5 mM for in vivo studies.

Rho-GTPase Pulldown Analyses

To analyze the effects of CASIN on the formation of active GTP-bound Cdc42, RhoA, and Rac1, effector pulldown assays were carried out as described previously. Cdc42GAP$^{-/-}$ MEF, LDBM, CD34$^+$ hCB cells were treated with CASIN at doses of 5-20 μM in parallel with vehicle control for 2 hrs after overnight starvation, and stimulated with cytokines subsequently. And then cells were lysed in a buffer containing 20 mM Tris-HCL (pH 7.6), 100 mM NaCl, 1% Triton X-100, 10 mM MgCl$_2$, 2 mM NaF, and Protease inhibitor cocktail (Roche Diagnostics). Lysates were incubated with GST-P21-binding domain of PAK1 for RAC1-GTP and Cdc42-GTP, and GST-RBD domain of Rhotekin for RhoA-GTP respectively. Both bound- and unbound-form of Rho GTPases were probed by immunoblotting with antibodies specific for Rac1 (BD biosciences), Cdc42 (BD biosciences), and RhoA (cell signaling).

Cytoskeleton Reorganization Studies

NIH3T3 cells were seeded in Dulbecco's modified Eagle's medium (DMEM) supplemented with 10% calf serum on glass coverslips at a density of $10^5$ cells per well in 8-well chambers. 24 hrs after cell seeding, cells were starved in serum-free DMEM for 24 h in the presence or absence of 5 μM or 10 μM CASIN for the last 2 hrs. cells then were stimulated with 5 ng/ml PDGF, 40 ng/ml LPA, or 100 ng/ml bradykinin, then fixed for immunofluorescence analysis. Immunostaining of F-actin with Rhodamine conjugated-phalloidin (Invitrogen) was carried out as described previously (Shutes, A., et al. J Biol Chem 282, 35666-35678 (2007)).

Column selected Lin$^-$c-Kit$^+$ BM primitive hematopoietic cells from C57Bl/6 mice were serum-starved in IMDM medium in the absence or presence of 5 μM or 10 μM CASIN in parallel with inactive CASIN analog. Cells then were stimulated with 100 ng/ml SDF-1α for 45 secs, and further stained with Rhodamine/Phalloidin for actin and DAPI for nucleus as described herein.

CFU-Adhesion/Migration Studies

Murine LDBM cells from Cdc42$^{+/+}$ as well as Cdc42$^{-/-}$ mice were used for CFU-adhesion/migration experiments as described previously. Briefly, for adhesion experiment, in the presence or absence of prior CASIN treatment at doses of 5 and 10 μM, $10^5$ cells were plated onto each well of 48-well plates pre-coated with fibronectin fragment CH296, which contains integrin α4β1-binding site. Adherent cells then were harvested by cells dissociation buffer (Gibco, Carlsbad, Calif.), and further plated in CFU assay. Similarly, for directional migration assay, 100 μl serum-free medium containing $10^5$ cells were loaded onto the upper chamber of a transwell plate with 5 μm pore size filter (Costar, Cambridge, Mass.), where 0.6 ml serum-free chemotaxis buffer with 100 ng/ml SDF-1α was added to the lower chamber. The cells in the lower chamber after 4 hrs incubation at 37° C. in 5% CO$_2$ were plated in CFU assay.

HSPC Determination

To determinate the hematopoietic progenitor content in the PB of mobilized C57Bl/6 mice, colony-forming unit assay was performed as described previously. Briefly, 200 ul PB was plated in triplicate into methylcellulose (MethocultM3434; StemCell Technology, Vancouver, BC, Canada). Colonies were then counted 7 d later.

To immunophenotypically profile the multi-compartments of HSPCs in BM, FACS analysis of six-color staining was carried out as previously. Briefly, freshly isolated BM cells from mobilized C57Bl/6 mice were stained with antibodies including IL-7Rα-APC-cy7, c-Kit-APC, Sca-1-PE, CD34-FITC, FcRII/III (CD16/32)-PE-cy7, and lin-cocktail antibodies conjugated with biotin which was secondarily labeled with Percp-cy5-streptividin. The sub-compartments of HSC, LT-HSC, ST-HSC, and CLP were quantified accordingly.

To functionally define the LT-HSC, serial transplantations of mobilized PB from C57Bl/6 mice into sublethally irradiated NOD/SCID mice were carried out. Briefly, 2×$10^7$ PB cells were harvested 40 hrs after CASIN mobilization, and subsequently transplanted to a sublethally irradiated primary recipient. Chimerisms of donor-derived cells in the BM and PB were monitored over time by FACS analysis of the congenic marker H2K$^b$. Subsequent secondary and tertiary transplantations were performed using prior BM cells, and monitored by FACS analysis as well.

Statistical Analyses

A two-tailed unpaired student's t-test was used for the statistical analyses. Values of p less than 0.05 were considered statistically significant.

EXAMPLE 7

Targeting Cdc42 by CASIN can mobilize the murine and human hematopoietic stem and progenitor cells in vivo, mimicking the effect of Cdc42 knockout.

Specificity and Reversibility of CASIN on Cdc42 Activity Inhibition

To exclude the inhibitory effect of CASIN on other Rac isoforms, Rho GTPases, and Ras, broader effector pull-down experiments are performed on these possible candidates with gradient doses of CASIN in LDBM and HCB cells as previously described. In addition, CASIN has been indicated as a noncovalent and reversible inhibitor in *Xenopus* egg extract. To confirm it, reversibility is monitored in this set of effector pull-down experiments. Four treatment groups are divided for both LDBM and HCB cells: (1) Serum starvation 20 h; (2) Serum starvation 20 h+growth factors stimulation; (3) Serum starvation 20 h+CASIN treatment (doses: 1, 2.5, 5, and 10 μM) 3 h+growth factor stimulation; (4) Serum starvation 20 h+CASIN treatment (doses: 1, 2.5, 5, and 10 μM) 3 h+wash the cells, and culture for another 3 h for recovery+growth factors stimulation. After different treatments, cells are harvested and lysed in a buffer containing 1% TritonX-100 and 10 mM MgCl2, and the lysates are probed with glutathione-agarose immobilized GST-Rhotekin (for RhoA, RhoB, and RhoC), GST-PAK1 (for Cdc42, Rac1, Rac2, and Rac3), or GST-RBD (for Ras) effector domain. Bound proteins are analyzed by immunoblotting with respective antibodies (BD Biosciences). Furthermore, changes of downstream targets of Cdc42, Rac, and Rho under the four treatment groups are assessed. Phosphorylation status of PAK1, WASP (effectors of Cdc42), WAVE (effector of Rac), and ROCK (effector of Rho) are monitored by western blots using respective antibodies.

To further verify the specificity of CASIN on Cdc42 activity inhibition, adhesion, migration, Actin polymerization is evaluated in both Cdc42−/− and Cdc42WT/WT MEF cells under the following five groups: (1) Cdc42WT/WT cells without treatment; (2) Cdc42−/− cells without treatment; (3) Cdc42WT/WT cells treated with CASIN; (4) Cdc42WT/WT cells treated with control medium; (5) Cdc42−/− cells treated with CASIN, in order to verify that CASIN function through inhibiting Cdc42. similarly, activities of the down stream effectors of Cdc42, Rac, and Rho under the five groups are monitored by western blot as above.

Pharmacokinetic and Pharmacodynamic Analysis for the Mobilization of Hematopoietic Progenitor Cells by CASIN in C57Bl/6 Mice The mice are i.p. administered with CASIN at 6 different doses (0.5, 1.0, 2.5, 5.0, 7.5, and 10 mg/Kg), and ~1 ml blood are collected by cardiac puncture for PD and PK analysis predosing, 6, 12, 24, 36, 48, 60, and 72 h postdosing. 5 mice are used for each group. To do PK analysis, concentrations of CASIN in plasma are determined by high-pressure liquid chromatography (HPLC) with electrochemical detection, and then all compartmental and noncompartmental analyses are performed using WinNonlin Professional (version 2.0) software (Pharsight, Cary, N.C.). The maximum drug concentration in serum (Cmax) and the time to Cmax are determined directly from the concentration-time curves. Terminal elimination half-life is determined by linear regression of the log-transformed final concentration-time points. As for the PD analysis, the effects of CASIN on mobilization of CFU-GM, CFU-GEMM, BFU-E and CFU-E to the blood of C57Bl/6 mice are evaluated. By using the rest of blood, assays for CFU-GM, CFU-GEMM, BFU-E and CFU-E are performed using ingredients and cytokine combinations, and then the plot of CFU number versus time across the dose groups is drawn. In this way, the optimal dose and time for mobilization in C57Bl/6 mice are determined. In addition, influence of multiple injections of CASIN or control medium given once, twice, and three times one half-life time apart are compared in C57/Bl6 in order to see if the HPC-mobilizing capacity of CASIN is desensitized following the first time mobilization, or there is the additive or even synergistic effect upon multiple injections.

Mobilizing Capability of CASIN on HPCs in Comparison with G-CSF, and in Combination with G-CSF, in Three Strains of Mice Broad interindividual variability exists in mobilization of HSC/Ps in different strains of mice and man. In some patients, G-CSF is a poor mobilizer. Therefore, the mobilizing capability of CASIN in comparison with G-CSF is evaluated, and in combination with G-CSF, in strains of mice that were reported to differ in responsiveness to G-CSF. Besides C57Bl/6, included in this set of experiments are C3H/HeJ and DBA/2 mice which respond very well to the mobilizing effects of G-CSF compared with C57Bl/6 mice. For each strain of mice, four groups are divided according to regimens used for mobilization: (1) Control medium; (2) CASIN administration; (3)G-CSF: twice a day for 2 days (4) G-CSF plus CASIN administration. Mice are bled 18 h after the last injection, and blood is plated in triplicate for CFU-C assay. Numbers of HPCs in CFU-E, BFU-E, CFU-GM, and CFU-GEMM are calculated per ml of blood later on reflecting the mobilization capacity of different regimens on HPCs.

CASIN Effects on Murine HSCs in C57Bl/6 Mice, with and without G-CSF

Although mobilization of HPC may be of use for short-term repopulation in a transplant setting, HSCs are required for long-term repopulation. To assess mobilization effect of CASIN on murine HSCs, a competitive repopulating assay is used. Basically, donor cells are harvested from peripheral blood of C5781/6 mice (CD45.2) after mobilization with CASIN or control medium. BM cells from nonirradiated B6.BoyJ (CD45.1) mice are served as competitor cells. Dilutions of donor blood cells from mobilized C57Bl/6 mice that contain long-term repopulating (LTR) cells compete with marrow cells of recipient B6.BoyJ mice at ratio of 3:1, 2:1, and 1:1 for engraftment in lethally-irradiated recipients. Donor chimerism is assessed using CD45 congenic markers by flow cytometry at 1, 2, 3, and 4 months posttransplantation. To further test self-renewal of CASIN-mobilized LTR cells, marrow cells that are obtained from competitively engrafted mice at 4-month posttransplantation are injected into lethally-irradiated secondary B6.BoyJ mice in a non-competitive setting. Donor chimerism again is assessed in the secondary mice based on the CD45 congenic markers. This set of experiments demonstrates that CASIN can rapidly mobilize LTR, self-renewing mouse HSCs.

The mobilization effect of CASIN on HSCs in comparison or combination with G-CSF is assessed under the following four mobilization groups: (1) Control medium mobilization group; (2) CASIN mobilization group; (3) G-CSF mobilization group (G-CSF: twice a day for 2 days); (4) CASIN plus G-CSF (twice a day for 2 days) mobilization group. And then the primary transplantation in a competitive setting at different ratios and secondary transplantation in a non-competitive setting are performed as above. The mobilization effects under different groups are analyzed based on the chimerism of donor-derived cells.

CASIN Effects on Human HSC/Ps, with and without G-CSF

The mobilization effects of CASIN on human HSC/Ps using an established preclinical in vivo mouse model are examined. Direct intrafemoral transplantation of a subset of primitive hematopoietic cells has been shown to repopulate and sustain human hematopoietic reconstitution in the bone marrow of immune-deficient NOD-SCID recipient mice. This reconstituting population of human hematopoietic cells is operationally defined as SCID-repopulating cells (SRCs), and accordingly represents candidate human HSCs.

Primitive CD34+ human neonatal umbilical cord blood cells are transplanted into sublethally irradiated recipients. Around 10-week posttransplantation, human multilineage repopulating capacity of transplanted HSCs is examined using flow cytometry for surface markers representing human lymphoid (CD19, CD20), myeloid (CD15, CD33) and primitive (CD34, CD38) hematopoietic subsets. Once it is found that all reconstituted recipients contain multilineage human donor-derived cells indicative of human HSC function, CASIN, in parallel with control medium as negative control and G-CSF as positive control, are administrated into mice, and the frequency and total number of primitive human hematopoietic cells (CD45+CD34+CD38−) in peripheral blood is determined along different time points postinjection of CASIN by flow cytometry. To further characterize the effect of CASIN on mobilization of primitive human HSC mobilization, progenitor potential is determined using functional clonogenic assays of hematopoietic colony-forming units (CFUs) derived from HPCs33. Numbers of CFUs are counted posinjection of CASIN treatment, in comparison with control medium and G-CSF administration.

Results

The experiments further confirm the specificity and reversibility of inhibitory effect of CASIN. Both HCB and LDBM cells CASIN can specifically inhibit the activity of Cdc42 in a dose-dependent manner without affecting activities of other Rho GTPases and Ras; and the activity of Cdc42 recovers 3 h after CASIN is washed away since in *Xenopus* egg extract CASIN is considered to function noncovalently. Stimulation of starved cells with growth factor is used as internal control here. Upon stimulation, the activities of Cdc42, Rac, Rho, and Ras increase significantly, indicating that the effector pull-down experiment works. In the experiments to evaluate the phosphorylation of downstream effectors of Cdc42, Rac, and Rho, CASIN can inhibit the phosphorylation of PAK1 and WASP without affecting that of WAVE and ROCK in both HCB and LDBM cells. Moreover, functionally, compared to the group of Cdc42WT/WT MEF cells without any treatment, CASIN treatment in Cdc42WT/WT MEF cells impairs MEF cells' ability of adhesion, migration and actin polymerization in vitro, similar to effects in Cdc42−/− MEF cell group. Because CASIN functions through Cdc42, in Cdc42−/− cells administration of CASIN do not increase the effects caused by Cdc42 KO at all. The phosphorylation activity of PAK1 and WASP are inhibited upon CASIN in WT MEF cells, while there is no inhibition shown in Cdc42 KO MEF cells upon CASIN. And the activity of WAVE and ROCK are be affected by CASIN in both WT and KO MEF cells.

The studies show that CASIN is capable of mobilization of HSC/Ps from the bone marrow to peripheral blood in C57Bl/6 mice. The purpose of PK and PD analyses is to characterize the exposure-response relationship of CASIN in mobilization when administered as a single dose agent in C57Bl/6 mice. The PK analysis based on the plasma concentration of CASIN by HPLC gives a plasma concentration versus time profile of CASIN across the different dose groups, and then can produce the values of Cmax, Tmax, and Half-life time. The half-life time is the basis to design the regimen of multiple-time CASIN administration. As for the PD analysis, plots are obtained of colony number versus time across the dose groups. Mobilization of HPCs with CASIN shows a dose-dependent pattern: with dose-increasing, the colony numbers of progenitors in CFU-E, BFU-E, CFU-GM, and CFU-mix increase gradually till reaching the peak number. This determines optimal time and dose of CASIN administration for maximal mobilization. CASIN enters the bone marrow and interferes with the HSC-niche interaction through multiple targets by inhibiting Cdc42 activity. As a result of the distribution and indirect effect of CASIN on mobilization, there is a delay in the concentration-effect relationship. In addition, multiple injections of CASIN one half-life time apart in C57/Bl6 give rise to stronger mobilization effects than that of single CASIN injection.

The three stains of mice used to test mobilization variability of CASIN are C57Bl/6, DBA/2, and C3H/HeJ. It has been demonstrated that C57Bl/6 is the most difficult mouse strain to be mobilized and studies described herein show that CASIN can rapidly mobilized HSC/Ps in C57Bl/6 mice, therefore CASIN can effectively mobilize DBA/2 mice and C3H/HeJ mice as well. G-CSF induces mobilization mainly through cleaving several adhesion molecules including c-Kit, VCAM-1, CXCR-4, and SDF-130, while CASIN induced mobilization involves targeting the cytoskeleton dynamics, expression and activation of Integrin, regulation of SDF-1 mediated migration, and expression of N-Cadherin. Compared to G-CSF induced mobilization, CASIN has its own unique mechanism for mobilization. Therefore, in comparison with G-CSF, CASIN produces more effective mobilization than G-CSF; while in combination with G-CSF, CASIN plus G-CSF induces an additive, even a synergistic effect on mobilization.

As such, similar results are obtained in the competitive repopulating experiments in C57Bl/6 mice which can not be mobilized by G-CSF. In the recipient B6.BoyJ mice, significant engraftment of donor derived cells in a dilution-dependent pattern in which ratio of dilution at 3:1 (donor:competitor) gives rise to the highest chimerism of donor engraftment. Additionally, the secondary transplantation in a non-competitive setting shows reasonable amount of engraftment from donor derived cells indicating self-renewal capacity of CASIN-mobilized HSCs. Moreover, in comparison or combination with G-CSF, CASIN alone or in combination with G-CSF shows the advantage of mobilization on HSCs over G-CSF alone in both primary competitive transplantation and secondary non-competitive transplantation.

Consistent with our and others preliminary studies, in the NOD-SCID mouse model which is transplanted with CD34+ HCB cells, around 10-week posttransplantation, the mice show human multilineage repopulation indicative of human HSC function by flow cytometry for surface markers representing human lymphoid (CD19, CD20), myeloid (CD15, CD33) and primitive (CD34, CD38) hematopoietic subsets. Upon administration of CASIN after the model show multilineage repopulation of human blood cells, the frequency and total number of primitive human hematopoietic cells (CD45+

CD34+CD38−) in peripheral blood increases significantly by flow cytometry; meanwhile, functionally by CFU-C assay, the colony numbers of human HPCs increases as well. These results strongly suggest that CASIN is very much useful clinically in mobilization for HSC transplantation.

EXAMPLE 8

HSC mobilization by targeting Cdc42 with CASIN coordinates with a transient proliferation of LT-HSCs and ST-HSCs
Experimental Designs and Methods:

To monitor the kinetics of CASIN effects on cell number, proliferation, and cell cycle change of HSCs, four time points post-CASIN-administration are focused on in this part. The determination of the four time points depends on the PD analysis to reflect the kinetics of HSCs from relatively quiescent state through proliferative state back to the quiescent state. In this study, the following time points are used: 0, 24, 48, and 96 hours postdosing as an example. Again C57Bl/6 mice are used here. Three subpopulations of HSC/P are investigated and phenotypically defined by flow cytometry: (1) Long-term reconstituting Flk-2-HSC (LT-HSC) subset (Lin−/c-Kit+/Sca-1+/Thy 1.1 int/FLK2−) capable of extensive self-renewal; (2) Short-term reconstituting Flk-2 int HSC (ST-HSCF) subset (Lin−/c-Kit+/Sca-1+/Thy1.1int/FLK21nt), which self-renews for a limited interval; (3) Nonself-renewing Flk-2+ multipotent progenitor (MPPF)subset (Lin−/c-Kit+/Sca-1+/Thy1.11nt/FLK2+).
Targeting Cdc42 by CASIN Results in Dynamic Alteration of the Frequency and Total Number of HSC/Ps in BM and PB Harvest of PB and BM: At 0, 24, 48, and 96 h post CASIN injection, the mice are sacrificed, and then the marrow is flushed from the femurs and tibias of C57Bl/6 mice and the blood cells are collected by cardiac incision.

Determination of the total cellularity of BM and PB: The numbers of cells in harvested PB and BM re counted after red blood cell lysis, and then the total cellularity is calculated.

Change of the frequency and total number of subpopulations of HSC/Ps in BM and PB: Both PB and BM cells are further prepared for flow cytometry analysis. Then, the frequencies of LT-HSC, ST-HSC, and MPP along the four time points are determined using the combinations of cell surface markers mentioned above phenotypically by flow cytometry. The absolute numbers of different subpopulations of HSC in BM and PB are calculated according to the total cellularity of BM and PB of the mice.
The Kinetic Change of BM HSC Cell Cycle and Proliferation State in Three Subpopulations Upon CASIN Administration FACS sorting: Each subpopulation of HSCs is purified by double FACS sorting from the total BM cells isolated from the mice at the different time points.

Cell cycle analysis: To characterize the cell cycle status of subpopulations of HSCs following treatment with CASIN, double-sorted cells are stained with Hoechst 33342 and Pyronin Y (H/PY), allowing simultaneous assessment of the fraction of cells with more than 2n DNA content (Hoechst 33342), as well as relative levels of total double-stranded RNA (PY). The stained cells are subjected to flow cytometry analysis and resorted into G0, G1, or S-G2/M subpopulations.

Short-term kinetic analysis of BrdU incorporation: Mice are injected with a single dose of CASIN, and BrdU is administrated intropertioneally 1 h or 12 h before sacrificing them at the end of day 0, 1, 2, or 4 postinjection. Each subset is analyzed for BrdU incorporation together with PI staining for DNA content by flow cytometry.

The Impact of Mobilization on BM LT-HSC Function in Hematopoietic Reconstitution Double FACS-sorted LT-HSC isolated from BM of untreated and 3 time points post injection are tested for their reconstitution capacity in limited dilution competitive reconstitution assays. Briefly, 50 LT-HSCs from donor C57Bl/6 mice (CD45.2) are transplanted into lethally irradiated congenic B6.BoyJ recipient mice (CD45.1) together with 3×105 CD45.1 helper BM cells. Then, the frequencies of CD45.2 donor-derived myeloid (M, Gr-1+, or Mac-1+) or lymphoid (L, B220+, or CD3+) cells are tested in the PB of the recipients at 4, 8, 12 weeks posttransplantation by flow cytometry for the hematopoietic reconstitution capacity. Recipient mice are considered to be reconstituted by CD45.2 donor cells if the frequencies of the donor-derived cells in the PB are greater than background levels.

Finally, reconstitution frequency of donor BM LT-HSC at each time point is calculated as the percentage of number of reconstituted mice out of total number of transplanted mice.
The Proliferation and Cell Cycle State of the Mobilized LT-HSCs Upon CASIN Administration Since it has been demonstrated that LT-HSC function in hematopoietic reconstitution after transplantation critically depends on maintenance of the quiescent state, the cell cycle status of mobilized peripheral LT-HSCs is tested. Double sorted LT-HSC in PB at 48 hr posttransplantation are stained with H/PY for DNA/RNA, resorted into G0, G1, or S-G2/M subpopulations for the cell cycle analysis.

To determine whether a subset of noncycling HSC could also be released into the bloodstream during HSC mobilization, BrdU incorporation into mobilized PB is analyzed at 48 h post CASIN treatment. Briefly, the mice are injected intraperitoneally with 1 mg BrdU every 6 h for a total of 36 h before sacrificing them at the end of mobilization protocol. Then the double FACS-sorted LT-HSC are analyzed for BrdU incorporation by flow cytometry.
CASIN Treatment Leads to Gene Transcription Change of Several Key Regulators in BM HSCs To determine if the kinetic change of cell cycle status is associated with the cell cycle regulator genes, the expression profile of a number of cell cycle regulators is examined, such as p21Cip1, c-Myc, Cyclin D1 and p27Kip1, in the three subpopulations of BM HSCs by real-time reverse-transcriptase quantitative PCR (RT-PCR) analysis along the different time points of CASIN administration.
Results CASIN administration leads to a transient self-renewing proliferative response of BM HSC and induce HSC migration from the BM into the blood stream. Therefore, both the numbers and frequencies of LT-HSC, ST-HSC, and MPP population in BM increase dramatically up to 48 h post-CASIN administration, and then decline and be back to normal up to 96 h post-CASIN administration. Additionally, in the Cdc42 conditional KO mice, Cdc42 deficiency in HSCs did not cause a change in the total cellularity of BM and PB3, thus there is a change of the total cellularity of BM and PB upon CASIN administration.

H/PY is used for staining for the cell cycle analysis. Based on the staining of Hoechst 33342 (for DNA content) and PY (for relative levels of total double-stranded RNA, each subgroup of HSC/Ps is resorted into G0, G1, and S/G2/M three subpopulations. Among the three subpopulation of HSC/Ps, LT-HSC has highest percentage of cells in G0 phase than ST-HSC and MPP before CASIN administration. After CASIN administration, all of three populations show decreased frequencies of cells in G0 phase, and more cells in G1 and S/G2/M phases. With the clearance of CASIN at 96 hours post-injection, the frequencies are back to the physiologic condition.

The short-term kinetics of BrdU incorporation are tested for cell proliferation analysis. For each time point in each subpopulation, there is an increased percentage of BrdU+ cells 12 hours post BrdU injection compared to 1 hour post BrdU injection. The proliferation of these three subpopulations along time after CASIN injection compared to non-treated mice shows similar kinetics to that of cell cycle.

The reconstitution frequency of BM LT-HSCs at 48 hours post injection significantly decreases compared to non-treated mice; while up to 96 hours post injection, with the recovery of the BM LT-HSC activity, its reconstitution frequency are back to normal. As such, the long-term repopulating capacity of HSCs in donor BM after CASIN administration is not impaired.

Since LT-HSC function in hematopoietic reconstitution after transplantation critically depends on maintenance of the quiescent state and data disclosed herein shows that the mobilized PB derived HSCs have very good long-term repopulating capacity as shown in the serial transplantation experiments, the mobilized PB HSCs are mainly in the quiescent state. Furthermore, our short-term BrdU incorporation experiment reveals whether a subset of noncycling HSC is also be released into the bloodstream during HSC mobilization. Mobilized HSCs are released into the bloodstream only after having recently divided. Therefore, in the BrdU incorporation experiment substantially every mobilized HSC in PB is BrdU positive.

Either a decreased level of P21Cip1 or an increased level of c-Myc could influence HSC self-renewal and proliferation in the BM microenvironment and may cause a loss of quiescence. And in the Cdc42 KO mice, a decreased P21Cip1 and an increased c-Myc was observed. Therefore, upon CASIN administration the expression of these two genes shows kinetic changes along the time.

EXAMPLE 9

HSC mobilization by CASIN opens up niches, thus being taken as a preparative regimen for hematopoietic stem cell transplantation.

Upon CASIN Treatment, LT-HSCs Mobilize Out of Niche, thus Opening Up the Niches

These studies use a double-labeling technique to monitor the localization change of LT-HSCs upon mobilization by CASIN.

AMD3100 and G-CSF induced mobilization are used as positive controls, while the control medium is used as a negative control. DBA/2, PeP3b, and C57Bl/6 mice are used in parallel to test the effects of variable mobilization capacity on the movement of LT-HSCs.

Basically, mice are fed BrdU (0.8 mg/ml) in drinking water for 10 days, followed by a chase period of seventy days, after which only the slow cycling LT-HSCs are found to retain the BrdU-label. At the end of the chase period of BrdU labeling, CASIN, AMD3100, G-CSF, or control is administered on the mice and 3H-TdR is pulse-labeled 1 h before sacrificing the mice. Mice are sacrificed at different time points post administration of mobilizers or control in order to reflect the kinetic changes of HSC localization upon mobilization. And then bone sections are immunochemically stained with anti-BrdU antibody and alkaline phosphatase-labeled secondary IgG, followed by visualization with red substrate. In the meantime, autoradiography is performed to visualize cell incorporated with 3H-TdR. A cell is considered to be double-labeled if it contains greater than 5 silver grains per nucleus over a bright nuclear pattern of red staining.

Mobilization by CASIN Can Be Taken as Preparative Regimen for Hematopoietic Stem Cell Transplantation If the microenvironmental niches are vacated after CASIN exposure, donor HSCs might engraft better in hosts treated with a mobilizing agent such as CASIN compared with non-mobilized controls. To test this, bone marrow transplantation is performed on recipient mice which are pre-conditioned with CASIN. To see different effects of mouse strains, three mouse strains with different mobilization potential as demonstrated in Aim1 supposedly are used in parallel as well: PeP3b, C57Bl/6, and C3H/HeJ mice. Additionally, AMD3100, G-CSF, and control medium are used in parallel with CASIN as controls.

Briefly, mice are treated with CASIN, and $4 \times 10^7$ donor bone marrow cells from congenic mouse strain are transplanted 48 h later. Donor cell engraftment is assayed at 3 months using the congenic markers by flow cytometry.

Additionally, multiple cycles of mobilization with CASIN may increase the number of available niches. Therefore, this study investigates whether repeated cycles of CASIN mobilization, each followed by donor cell transplantation, could result in increased engraftment. Briefly, mice receive one weekly injection of CASIN on 3 consecutive weeks and $4 \times 10^7$ donor marrow cells are transplanted 48 hours after each mobilization. Control animals also received 3 weekly infusions of $4 \times 10^7$ donor marrow cells but no CASIN. And the donor engraftment is assayed at 3 months after transplantation as well.

Results

As presented above, to proliferate, HSCs need to move out of their quiescent niche and into a proliferation zone. As such, before CASIN administration, LT-HSCs are mainly located in the bone marrow niche and labeled with BrdU (red stained nuclei), while the cycling HSCs are located somewhere in the proliferative zone and labeled with 3HdR (dark grains); 48 hours or earlier after mobilization, some of LT-HSCs move to the proliferative zone and undergo proliferation, thus these studies show some double labeled cells in the proliferation zone, and the number of BrdU-labeled LT-HSC in bone marrow niche is reduced; at 96 hours post-mobilization, with the clearance of CASIN, proliferated LT-HSC labeled with 3H-TdR are back to quiescent state, thus the number of LT-HSCs in the endosteal BM niche are recovered with some 3H-TdR+ cells. Additionally, different mouse strains show different potential of movement from quiescent zone to proliferative zone. DBA/2 mice have the greatest potential, while the C57Bl/6 mice have the poorest.

Since vacating the niche could lead to better engraftment, CASIN, G-CSF, or AMD3100 treatment result in significantly increased engraftment of donor cells in the pre-conditioned recipients, compared to the non-mobilization control. Moreover, the different mouse strains show different effects of CASIN on engraftment improvement, comparable to their different capacities for mobilization. Similar to the niche-vacating, DBA-2 mice get the greatest improvement on engraftment upon pre-condition with CASIN.

As indicated that additional microenvironmental niches become available with repeated mobilization cycles, that engraftment in the mice with 3-cycle administration of CASIN and subsequent transplantation is further improved compared to one cycle.

EXAMPLE 10

This studies investigate the application of CASIN to Fancc−/− Fanconi anemia mouse model for both mobilization and preconditioning.

To Assess the Mobilization Effect of CASIN in Fancc−/− Mice in Parallel with WT Mice, with or without G-CSF The effects of CASIN on HSC/P mobilization in Fancc−/− mice are investigated under four groups in parallel with WT mice: (1) Control group; (2) G-CSF group: 2.5 μg G-CSF per mouse, twice a day for 4 d120; (3) CASIN group: 2.5 mg/Kg; (4) combination of CASIN and G-CSF: one injection of CASIN is given 40 h before the end of 4 d G-CSF administration.

Fancc−/− or WT mice are mobilized with regimens corresponding to the four experimental groups. Then PB are harvested by cardiac puncture. Phenotypically, the absolute number and percentage of HSC/Ps in PB after mobilization are determined as those of LSK (Lin− Sca+c-Kit+) cells by flow cytometry. Functionally, CFU-C assay is performed in triplicate for each mouse by using PB of mice from different experimental groups, and CFU-GM, CFU-GEMM, BFU-E, and CFU-E are distinguished by morphology and using cytokine combinations. Furthermore, the long-term repopulation capacity of the mobilized HSCs is evaluated using a competitive repopulating assay and subsequent secondary transplantation as discussed above.

HSC Mobilization by CASIN could be Taken as a Preparative Regimen for BM Transplantation in Fancc−/− Mice, with or without CY Four preparative regimens before BM transplantation on Fancc−/− mice are used to evaluate the capacity of CASIN as a preconditioning agent: (1) Control group; (2) CY group: a single dose of 40 mg/kg CY intraperitoneally; (3) CASIN group: 2.5 mg/Kg; (4) combination of CASIN and CY: one injection of CASIN is given in combination with reduced doses of CY.

Fancc−/− mice are preconditioned with each of these four regimens, and $4 \times 10^7$ BM cells from congenic strain mice are transplanted into preconditioned mice by tail vein injection. Mice that underwent transplantation are bled every four weeks to monitor the chimerism of donor-derived cells in PB. And at 3 m, the mice are sacrificed to evaluate the engraftment of donor-derived cells in BM.

Results

As many patients who have Fanconi anemia are poor responders to HPC mobilization with G-CSF, these experiments demonstrate G-CSF is a less effective mobilizer of HSC/Ps in Fancc−/− mice than in WT mice. Hence, after G-CSF administration, PB of WT mice contain more LSK cells by flow cytometry and more colonies of progenitors by CFU assays than Fancc−/− mice.

Unlike G-CSF, CASIN is an effective mobilizer in Fancc−/− mice, showing that in Fancc−/− mice there are increased numbers of LSK cells and progenitor colonies after mobilization comparable to that of WT mice.

As there are differences in terms of mechanism underlying CASIN and G-CSF induced mobilization, CASIN and G-CSF have additive, or synergistic effects on mobilization in Fancc−/− mice, showing that in both Fancc−/− and WT mice administration of CASIN and G-CSF in combination can mobilize much more LSK cells and progenitor colonies than CASIN or G-CSF alone.

CASIN can be used as a preparative regimen for BM transplantation in Fancc−/− mice alone or in combination with reduced amount of the myeloablative agent CY, indicated by the reasonable repopulation and engraftment of donor derived cells in PB and BM of Fancc−/− recipient mice, which is detected by flow cytometry. Preconditioning with CY as a positive control results in comparable engraftment and repopulation in Fancc−/− mice to CASIN alone or CASIN together with reduced doses of CY. Thus, toxicity, and even malignancy caused by use of myeloablative regimen is avoided or dramatically reduced by use of nonmyeloablative CASIN, therefore greatly beneficial to FA patients.

EXAMPLE 11

Rho GTPase Cdc42 Coordinates Hematopoietic Stem Cell Quiescence and Niche Interaction in the Bone Marrow Adult hematopoietic stem cells (HSCs) exist in a relatively quiescent state in the bone marrow (BM) microenvironment to execute long term self-renewal and multi-lineage differentiation functions (Bradford, G. B. et al. (1997) Exp Hematol 25, 445-53; Cheshier, S. H. et al. (1999) Proc Natl Acad Sci U S A 96, 3120-5; Morrison, S. J. & Weissman, I. L. (1994) Immunity 1, 661-73). The maintenance of HSC quiescence involves both extrinsic and intrinsic mechanisms. A number of genes that encode cell cycle or transcriptional regulators, including p21 Cip1, p27 Kip1, β-catenin/axin, cyclin D1 and c-Myc (Cheng, T. et al. (2000) Science 287, 1804-8; Lacorazza, H. D. et al. (2006) Cancer Cell 9, 175-87), have been shown to regulate the intrinsic programs of HSCs in this process. In addition, interactions of HSCs with the marrow microenvironment in specific anatomical and functional areas, referred to as niches, in the maintenance of HSC quiescence have also gained increasing recognition (Li, L. et al. (2005) Annu Rev Cell Dev Biol 21, 605-31). One hypothesis is that the intrinsic and extrinsic cues such as BMPs, Ca2+, Notch ligands and/or Ang-1/Tie2 (Arai, F. et al. (2004) Cell 118, 149-61; Calvi, L. M. et al. (2003) Nature 425, 841-6; Zhang, J. et al. (2003) Nature 425, 836-41; Adams, G. B. et al. (2005) Nature 439, 599-603) in the BM microenvironment may coordinately regulate the HSC quiescent state.

Despite of the identification of these molecular factors in HSCs and in BM that may collectively contribute to the maintenance of quiescence (Arai, F. et al. (2004) Cell 118, 149-61), the mechanism coordinating HSC cell cycle regulation and niche interaction remains unclear. Cdc42 is a ubiquitously expressed member of the Rho GTPase family involved in the regulation of multiple cell functions including actin polymerization, cell-to-cell or cell-to-extracellular matrix adhesion, and gene transcription (Etienne-Manneville, S. et al. (2002) Nature 420, 629-35). Although its function has been extensively studied in various cell systems by expression of dominant negative or constitutively active mutants, the physiological roles of Cdc42 in most primary cell lineages, particularly HSCs, remain unclear. Previously in a gain-of-Cdc42 activity, Cdc42GAP−/− mouse model, constitutively increased Cdc42-GTP species caused increased hematopoietic progenitor apoptosis, disorganized actin structure and defective engraftment without affecting the cell cycle status. To further define the role of Cdc42 in HSC regulation, the present studies present a conditional knockout mouse model in which cdc42 gene is inducibly deleted in hematopoietic cells (Wang, L. et al. (2006) Blood 107, 98-105). The results unveil a novel role of Cdc42 in maintaining HSC quiescence and in retaining HSCs in the correct location in the BM niche by regulating the expression of a number of key cell cycle regulators including c-Myc and p21Cip1, and cell adhesion molecules such as β1-integrin and N-cadherin, as well as the actin structure.

Loss of Cdc42 from HSCs Results in Altered Frequency and Distribution of HSCs

Conventional cdc42 gene-targeted mice die at E7.5 (Chen, F. et al. (2000) Curr Biol 10, 758-65), precluding a detailed analysis of Cdc42 function in HSCs with this animal model.

Figure 12A:
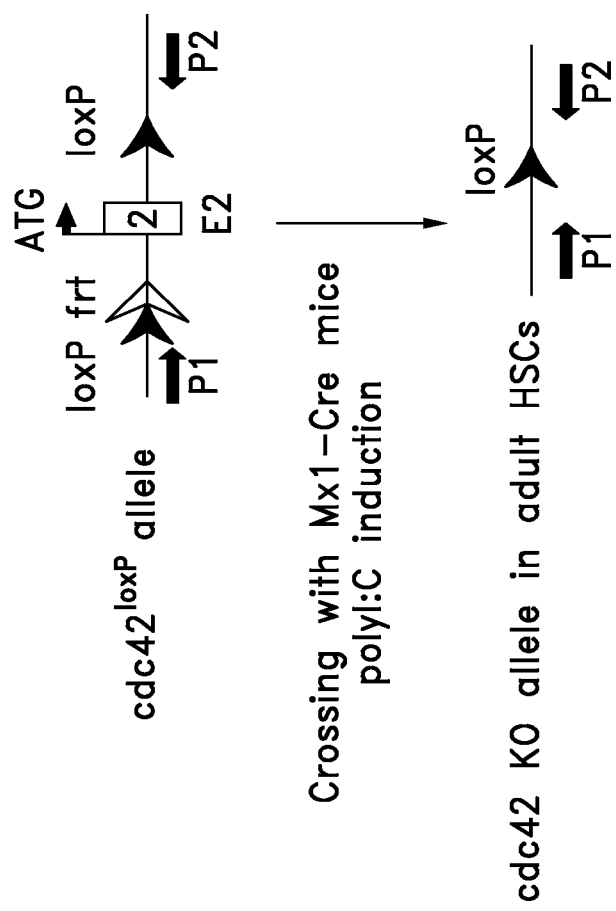
FIG. 12. Cdc42-gene targeting in hematopoietic cells causes expansion and mobilization of HSCs. (A) Inducible Cre-mediated disruption of cdc42 in Mx1-Cre;cdc42$^{loxP/loxP}$ mice. Arrows indicate the PCR primers P1 and P2. (B) Cdc42 deletion in BM was examined by PCR or anti-Cdc42 Western blotting. (C, D) Numbers of HSCs in BM, including LT-HSCs and ST-HSCs (C), and LSK cells in PB, spleen and liver (D), were determined by FACS analysis. (E) The CFU-C activities in PB, spleen and liver were determined in the methylcellulose culture. (F) BM nucleated cells were serially replated in the methylcellulose culture. The numbers of CFU-C obtained after each round of replating are shown.
Figure 12B:
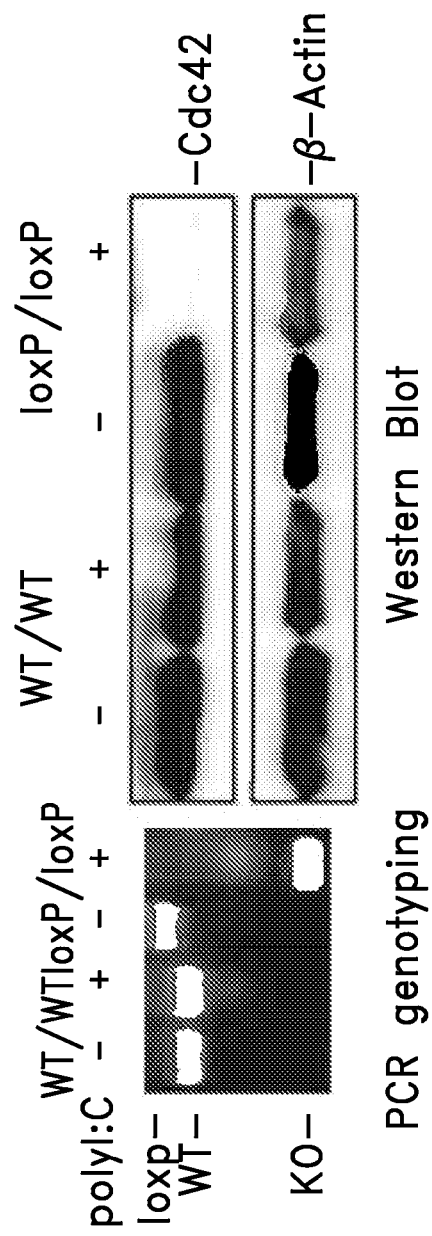

To circumvent this experimental limitation, conditional gene targeted mice were generated with exon 2 of cdc42 gene containing translation initiation codon and nucleotide binding sequences flanked by a pair of loxP sequences (FIG. 18). For examination of the role of Cdc42 in HSC regulation, cdc42$^{loxP/loxP}$ mice were cross-bred with transgenic Mx1-Cre mice to allow interferon-inducible cdc42 gene excision in hematopoietic cells (FIG. 12A). At five days after the administration of three doses of polyI:C to induce an interferon response in Mx1-Cre;cdc42$^{loxP/loxP}$ mice, the total cellularity of BM did not change but the floxed cdc42 gene sequences and Cdc42 protein became undetectable in the BM cells (FIG. 12B; hereof referred to as KO).

Figure 12D:
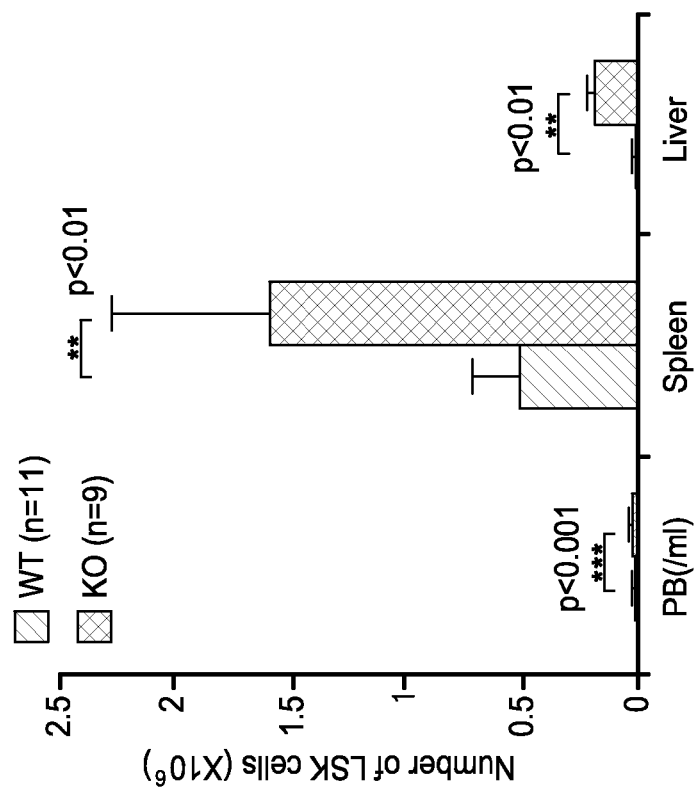
Figure 12C:
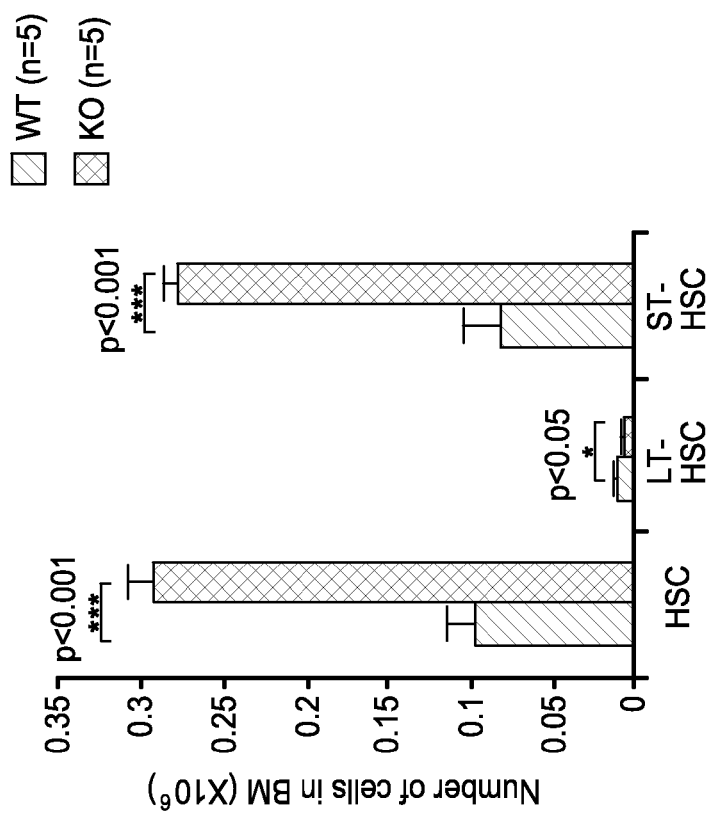

To investigate whether Cdc42 deficiency affects HSC function, the HSC frequency in the BM was first determined phenotypically by flow cytometry. Lin$^-$Sca1+ c-Kit$^+$(LSK) cells expressing high or low levels of CD34 were gated (FIG. 19) to distinguish between putative long-term repopulating HSCs (LT-HSCs) (Lin$^-$Sca1$^+$ c-Kit$^+$CD34$^{low}$) and short-term repopulating HSCs (ST-HSCs) (Lin$^-$Sca1+ c-Kit$^+$CD34$^{high}$) (Goodell, M. A. et al. (1997) Nat Med 3, 1337-45; Osawa, M. et al. (1996) Science 273, 242-5). Loss of Cdc42 led to a two to three-fold increase in phenotypically defined ST-HSCs, and to ~two fold decreases in LT-HSCs (FIG. 12C).

Figure 12E:
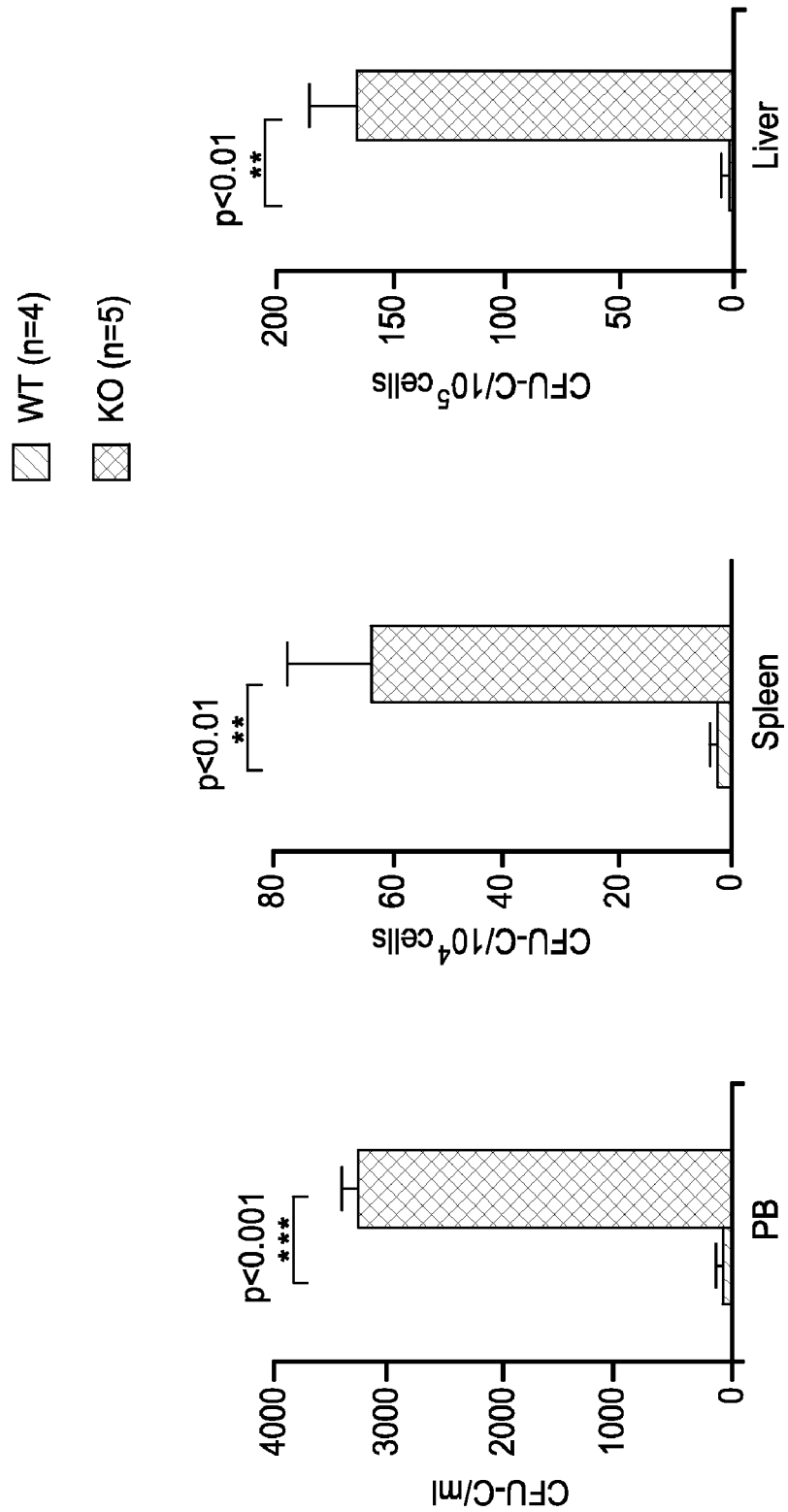
Figure 12F:
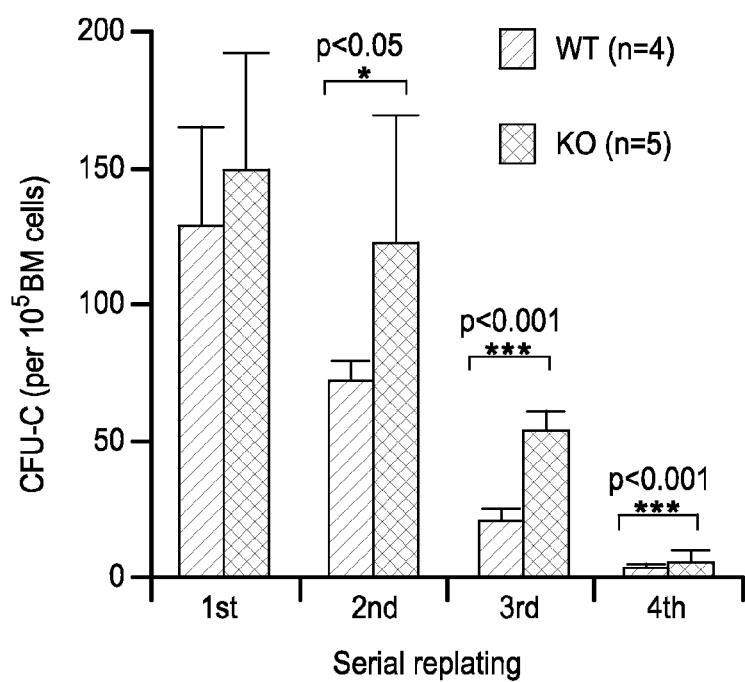

Adult HSCs are normally located in the BM and mostly absent from PB or liver (Arai, F. et al. (2004) Cell 118, 149-61; Calvi, L. M. et al. (2003) Nature 425, 841-6; Zhang, J. et al. (2003) Nature 425, 836-41; Kiel, M. J. et al. (2005) Cell 121, 1109-21). Cdc42-deletion led to a drastic increase in the content of LSK population in PB, liver and spleen in addition to BM (FIG. 12D). Consistent with these findings, there was a significant increase in the functionally defined progenitor cell numbers in peripheral blood (PB), spleen and liver upon cdc42-deletion (FIG. 12E), indicating that HSCs were mobilized to PB and other tissues by cdc42-deletion. PolyI:C treated WT mice reconstituted with Mx1-Cre; cdc42$^{loxP/loxP}$ BM cells showed similar alterations of tissue distribution of LSK and progenitor cells compared with the KO mice, indicating that the HSC and progenitor mobilization phenotypes are intrinsic to the hematopoietic cells. Serial replating experiments further demonstrated a significantly higher proliferative potential of the KO cells as defined by replating efficiency in colony-forming progenitors (FIG. 12F). These results indicate that Cdc42 deficiency increases the number and alters the distribution of HSCs leading to a massive mobilization of HSCs and progenitors into peripheral circulation.

Cdc42-Deficiency in HSCs Results in Defective Engraftment

Figure 13A:
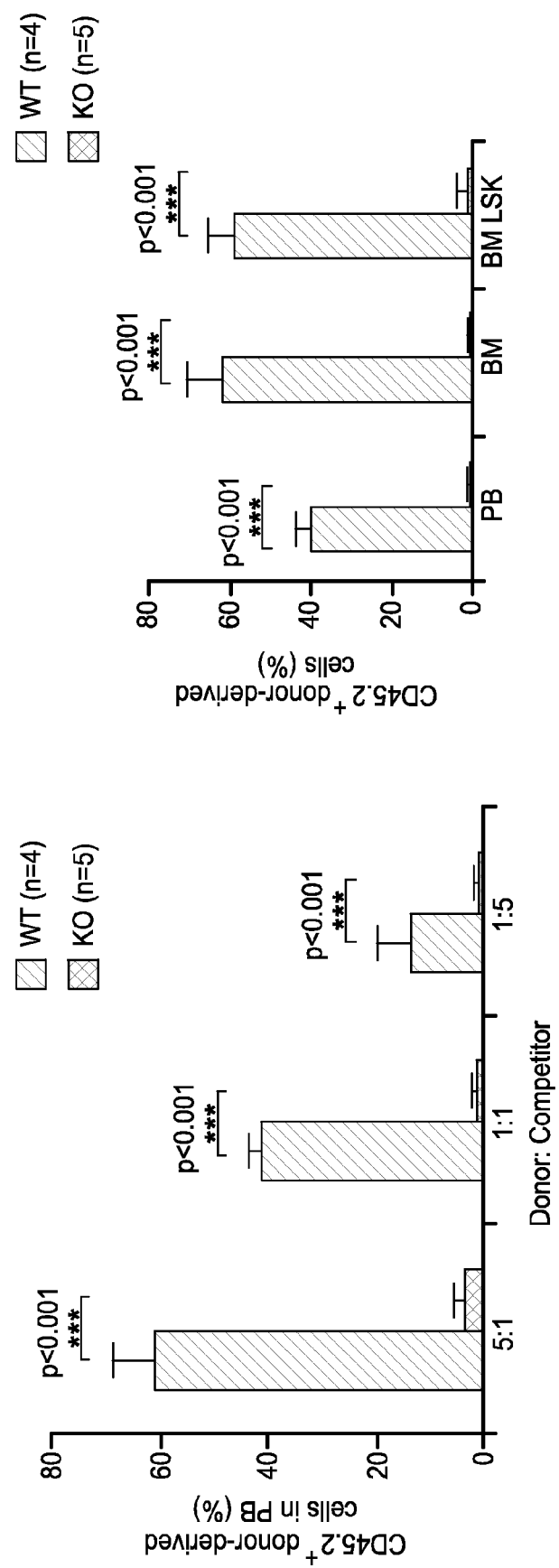
FIG. 13. Cdc42-deficiency causes an engraftment failure of HSCs. (A) CD45.2$^+$WT or KO BM nucleated cells were transplanted into lethally irradiated, CD45.1$^+$BoyJ recipient mice at 5:1, 1:1 or 1:5 ratio with CD45.1$^+$WT competitor cells, and the CD45.2$^+$ cell population in recipients were determined by flow cytometry 20 weeks post-transplantation (left hand panel). The chimerism was also measured in PB, BM and BM LSK cell populations of 1:1 competitive transplantation recipient mice at the 12 week time point (right hand panel). (B) Sub-lethally irradiated NOD/SCID recipient mice were used as the transplantation recipients in the absence of competitors. The H2 Kb+ donor cells in the PB and BM of recipient mice were determined 8 weeks post-transplantation. (C) The BM cells of the Mx-Cre;cdc42$^{WT/WT}$ or Mx-Cre;cdc42$^{loxP/loxP}$ genotype were transplanted along with WT competitors at 1:1 ratio into lethally irradiated WT recipients. 8 weeks after reconstitution, mice were treated with polyI:C to delete cdc42 as shown in the scheme (left hand panel). The donor-derived Gr1$^+$/Mac1$^+$ lineages in PB (middle panel), and LSK cells in BM (right hand panel), were quantified at the indicated time points after the polyI:C treatment.
Figure 13B:
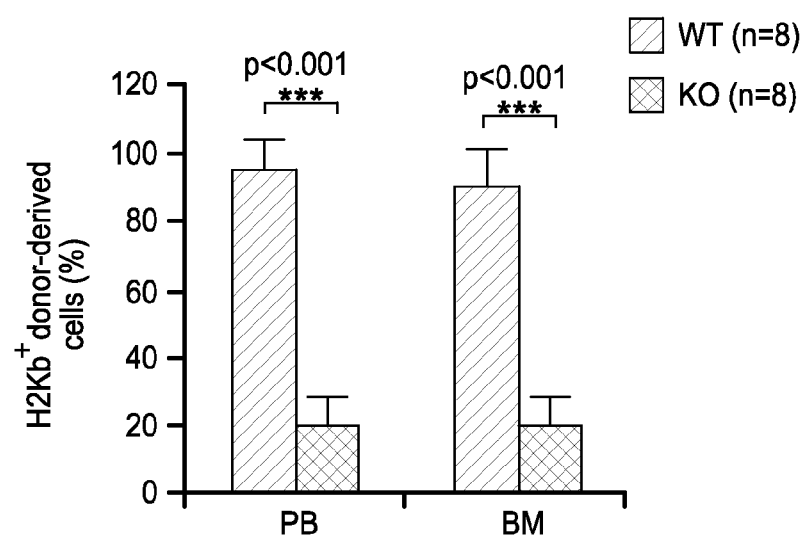
Figure 13C:
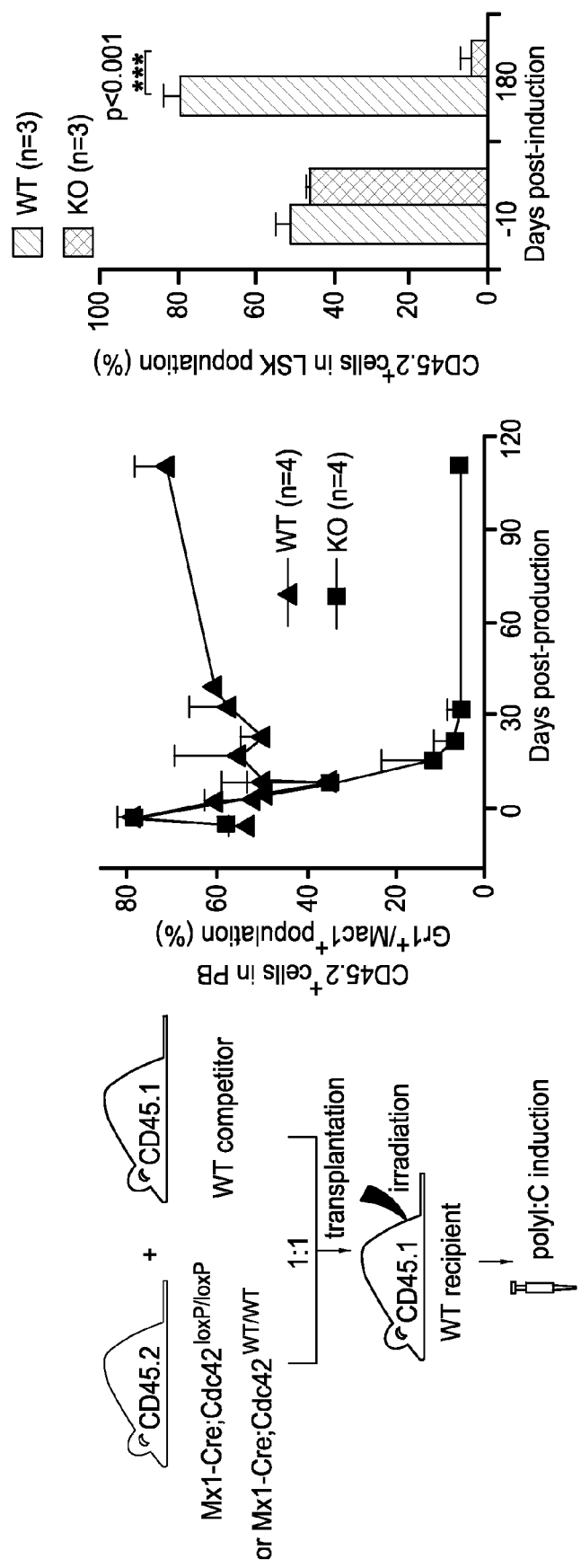

To further assess Cdc42$^{-/-}$ HSC function in vivo, BM cell transplantation into lethally or sub-lethally irradiated recipient mice were carried out. Competitive repopulation assays combining CD45.1$^+$WT and CD45.2$^+$ KO BM cells at varying ratios resulted in less than 5% KO-derived PB or BM cells while the control competitive transplantation using WT cells resulted in the expected genotypic ratios of the PB cells 4 or 10 weeks after transplantation into CD45.1$^+$BoyJ recipients (FIG. 13A). In a non-competitive setting, less than 20% KO donor derived PB or BM cells, compared with over 95% WT donor derived cells, were detected 8 weeks post-transplantation when sub-lethally irradiated NOD/SCID mice were used as recipients (FIG. 13B). To rule out potential effects in these assays brought by pre-deletion of Cdc42, mice engrafted with CD45.2$^+$, Mx1-Cre;cdc42$^{loxP/loxP}$ or Mx1-Cre;cdc42$^{WT/WT}$ BM cells that were mixed at a 1:1 ratio with CD45.1$^+$, WT competitor BM cells were treated with polyI:C, and the composition of recipient PB was monitored for up to 180 days (FIG. 13C). The KO Gr1$^+$ and Mac1$^+$ population decreased to less than 5% after 25 days under these competitive settings (FIG. 13C). The LSK population of the KO genotype in the BM also reduced to less than 5% 180 days after cdc42-deletion (FIG. 13C), suggesting that Cdc42 is essential for in vivo HSC engraftment. Thus, Cdc42-deletion leads to an altered stem cell pool that is functionally defective in engraftment and in supporting normal hematopoiesis.

Cdc42-Deficiency Leads to HSC Cell Cycle Activation

Whether Cdc42$^{-/-}$ HSCs demonstrate a cell cycle or survival defect was tested. To this end, in vivo BrdU labeling was performed in mice to determine the proliferative status of LSK cells in the BM. The percentage of cells in the S phase was significantly higher in Cdc42$^{-/-}$ LSK cells than in WT cells (FIG. 14A). In vitro BrdU pulse-labeling of isolated LSK cells also indicated that Cdc42-deficiency resulted in increased S-phase and G2/M-phase populations (FIG. 14B). To determine if the enhanced BrdU incorporation in Cdc42$^{-/-}$ LSK cells is associated with an increased stem/progenitor population that is in active cell cycle, a combination of DNA and RNA staining by Hoechst 33342 and Pyronin Y was used to distinguish G0 and G1 phases of the cells (Cheshier, S. H. et al. (1999) Proc Natl Acad Sci USA 96, 3120-5; Cheng, T. et al. (2000) Science 287, 1804-8). As shown in FIG. 14C, Cdc42-deficiency caused a significant loss of Lin$^-$c-Kit$^+$ progenitor cells in the G0 phase and an increase in the G1 phase. These cell cycle changes were intrinsic to the HSCs as revealed by an examination of the LSK cells from lethally irradiated transplantation recipients of Mx1-Cre; cdc42$^{loxP/loxP}$ or matching WT donor BM cells after the polyI:C treatment. In contrast to the cell cycle alterations, however, no difference in apoptosis was detected between KO and WT LSK cells (FIG. 20). These results indicate that Cdc42 is required for the maintenance of quiescence, but not survival, of HSCs.

Figure 15A:
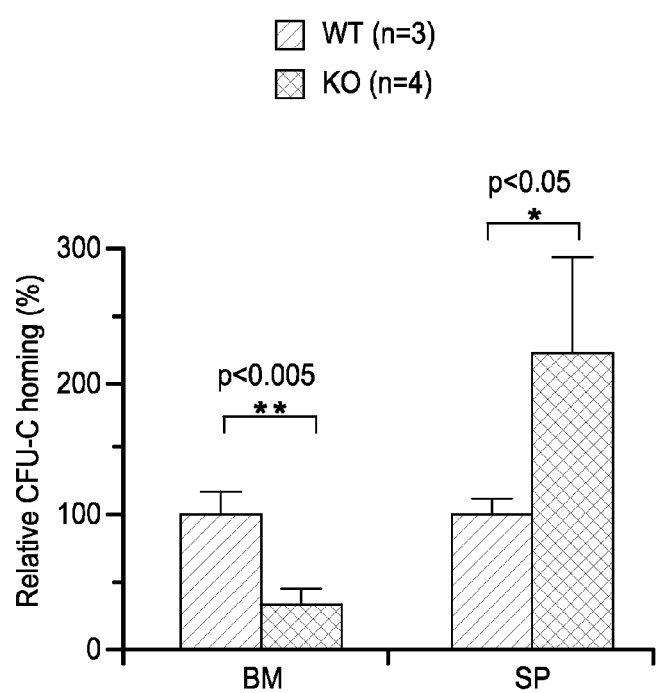
FIG. 15. Cdc42$^{-/-}$ HSCs show defective localization in the BM endosteum. (A) The homing ability of BM cells into an irradiated host was determined. (B) The BM cells (left panel)
Figure 15B:
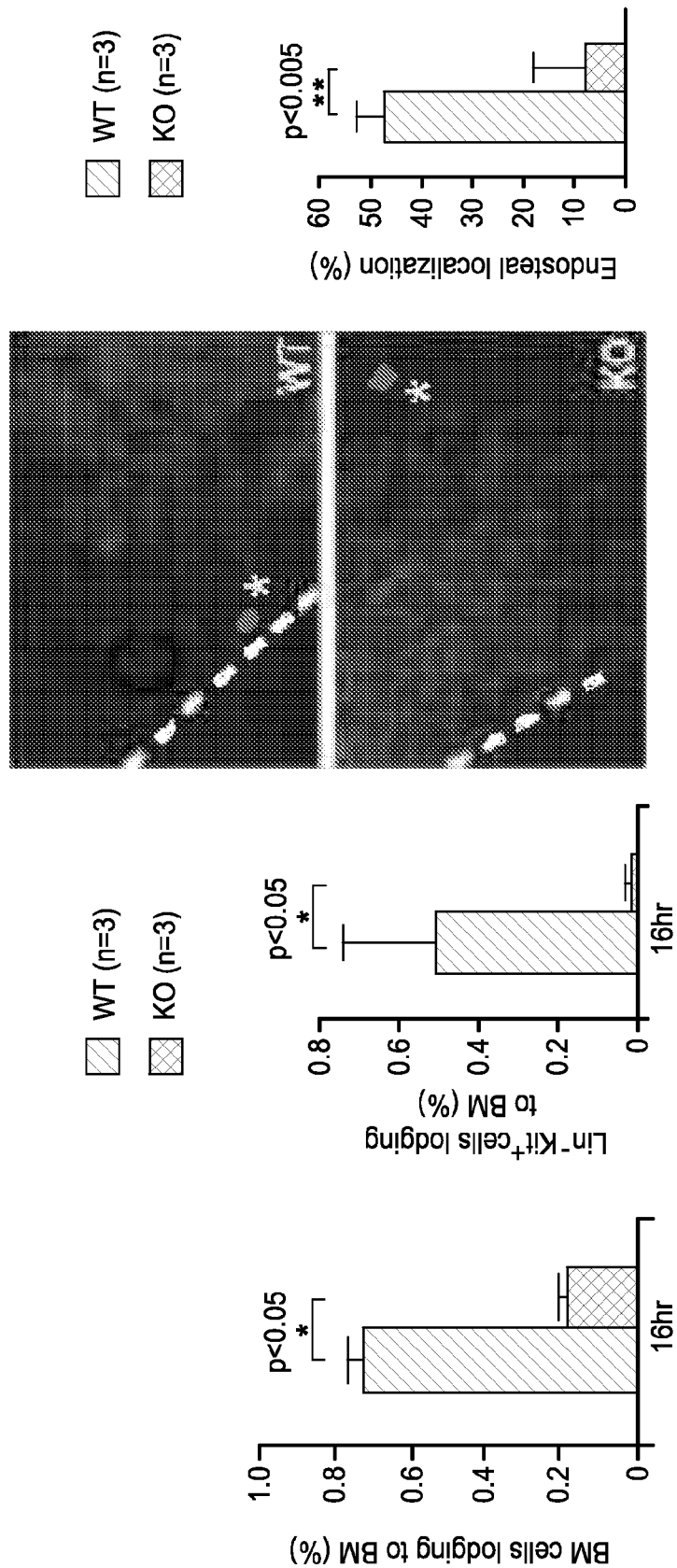

Cdc42-Deficiency Leads to Homing, Lodging and Retention Defects of HSCs in the BM Endosteum To resolve a potential paradox of the observed cell cycle activation phenotype and the engraftment failure of cdc42$^{-/-}$ HSCs, whether primitive hematopoietic cells deficient in Cdc42 were able to properly engage the BM niche was determined. Cdc42 deficient progenitors were severely impaired in their ability to enter the marrow tissue in a homing assay (FIG. 15A). The lodging ability of fluorescently labeled WT or KO BM or Lin$^-$ c-Kit$^+$ BM cells in the BM was further examined by comparing their relative distance from the endosteal surface of BM 16 hours after transplantation into non-irradiated recipient mice (Adams, G. B. et al. (2005) Nature 439, 599-603; Cancelas, J. A. et al. (2005) Nat Med 11, 886-91; Wilson, A. et al. (2006) Nat Rev Immunol 6, 93-106). This analysis revealed a striking reduction of the Cdc42$^{-/-}$ BM and Lin$^-$c-Kit$^+$BM cells to localize or return to the endosteal bone surface (FIG. 15B). LT-HSCs, which can retain BrdU labeling over a long period of time (e.g., 70 days in mice) due to their relative quiescent state, are located close to osteoblastic cells lining the bone surface (Calvi, L. M. et al. (2003) Nature 425, 841-6; Zhang, J. et al. (2003) Nature 425, 836-41). As shown in FIG. 15C, the number of BrdU long-term retaining (BrdU-LTR) cells at the trabecular bone surface was significantly reduced after cdc42-deletion, indicating that Cdc42 is also important for LT-HSC retention in the endosteal niche in the BM. These results indicate that Cdc42-deficient HSCs are defective in homing, lodging, and retention in the endosteal niche, which may contribute to the engraftment failure.

Figure 16E:
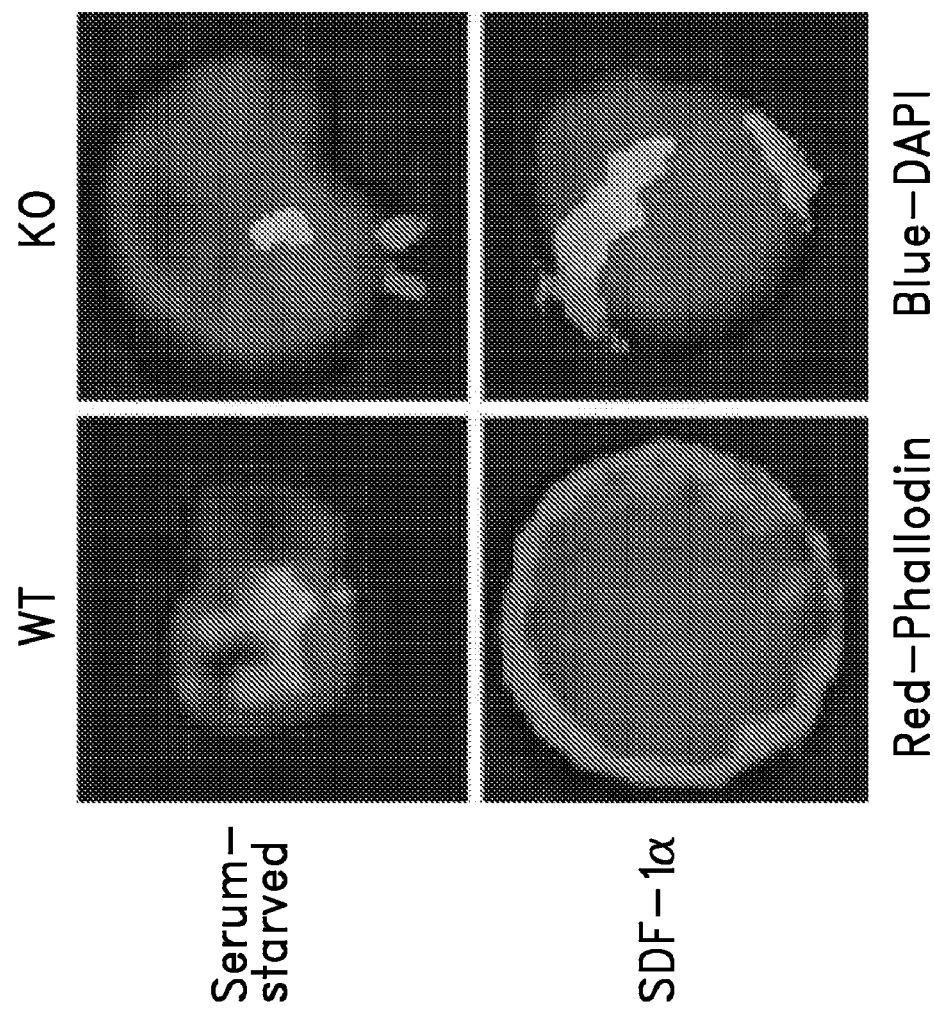

Cdc42 is a Critical Regulator of HSC Adhesion, Migration and Actin Reorganization To examine whether the observed homing and lodging defects of KO HSCs are associated with alterations in adhesion activity, the adhesion assays of Lin$^-$c-Kit$^+$ progenitor cells to recombinant fibronectin fragments, or HSC to stroma cells, were carried out. The adhesion of KO progenitor cells to both fibronectin fragments CH296 (containing both the α4β1 and α5β1 integrin binding sites) and H296 (containing the α4β1 integrin binding site) were significantly reduced (FIG. 16A), as was the adhesion of day 35 cobblestone area-forming cells (CAFCs), which likely represent HSCs, to a bone marrow derived stroma cell line (FBMD-1) that is capable of supporting hematopoiesis (FIG. 16B). Moreover, the abilities of KO cells to migrate across a transwell, or across an endothelial monolayer, toward a SDF-1α gradient, as well as chemokinesis, were severely impaired (FIGS. 16C & 16D). Isolated KO stem/progenitor cells were also defective in reorganizing F-actin structure upon SDF-1α stimulation (FIG. 16E and supplemental FIG. 21). The studies demonstrated that Cdc42 is critical in HSC and progenitor cell adhesion, directional migration and actin reorganization, functions that are important for HSC homing and retention in the BM microenvironment.

Figure 17B:
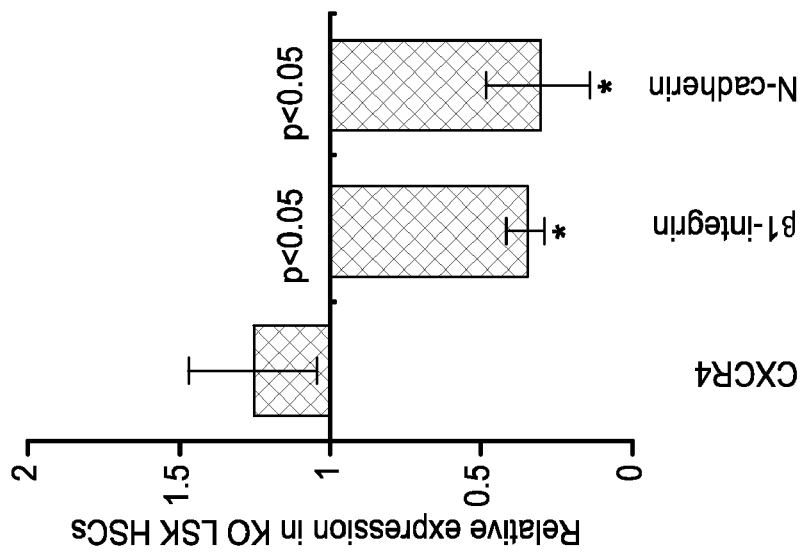
Figure 17A:
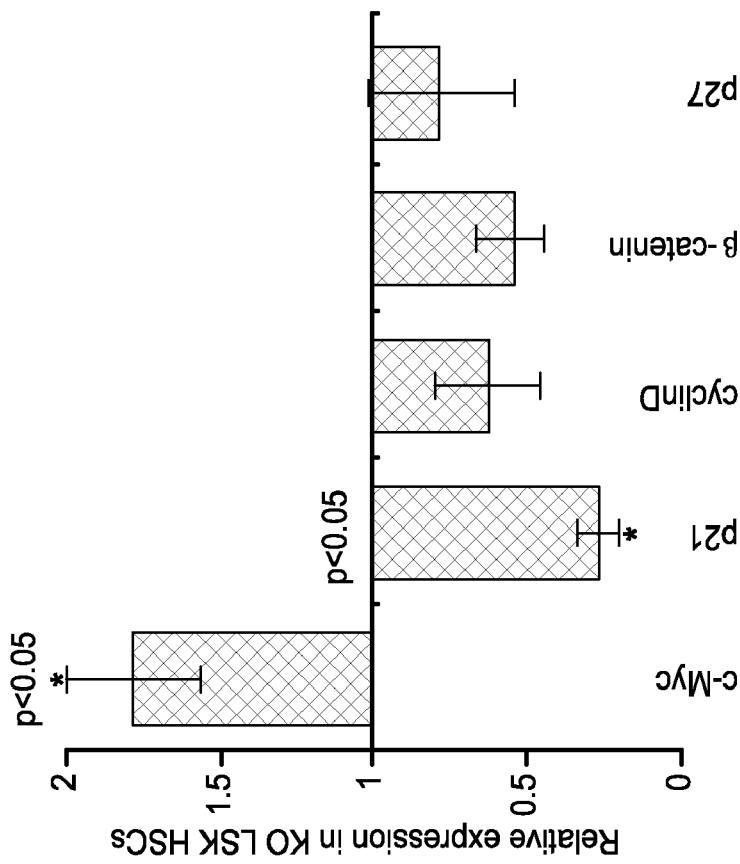

Cdc42 Regulates Gene Transcription of Several Key Cell Cycle and Adhesion Regulators in HSCs To determine the potential mechanism underlying the accelerated cell cycle status and the defective adhesion properties of the Cdc42 KO HSCs, the expression profile of a number of cell cycle regulators and adhesion molecules in LSK cells that have been previously implicated as potential effectors of Rho GTPases and are likely important for HSC quiescence state maintenance or BM retention were further examined. Real-time reverse-transcriptase quantitative PCR (RT-PCR) analysis showed that $Cdc42^{-/-}$ LSK cells expressed a significantly decreased level of $p21^{Cip1}$ but an increased level of c-Myc compared with WT LSK cells, whereas the cyclin D1 and $p27^{kip1}$ mRNA levels remained unchanged (FIG. 17A). Either decreased level of $p21^{Cip1}$ or increased level of c-Myc expression could influence HSC self-renewal and proliferation in the BM microenvironment and may cause a loss of quiescence (Cheng, T. et al. (2000) Science 287, 1804-8; Wilson, A. et al. (2004) Genes Dev 18, 2747-63). RT-PCR analysis also revealed a significantly decreased expression of β1 integrin and N-cadherin, but not CXCR4, molecules that have been shown to be critical for homing, mobilization and micro-localization of HSCs (Zhang, J. et al. (2003) Nature 425, 836-41), in Cdc42-deficient LSK cells (FIG. 17B). These changes may mechanistically contribute to the increased mobilization and decreased interaction of $cdc42^{-/-}$ HSCs with the BM endosteal niche. Collectively, the studies indicate that Cdc42 controls the expression of key cell cycle and adhesion regulators as well as actin structure to coordinate the quiescence maintenance and the BM niche interaction of HSCs.

CONCLUSION

The present study shows that deletion of Cdc42 reduces the number and frequency of quiescent HSCs and increases the stem/progenitor population that is in active cell cycle. Cdc42-deficiency also causes defective homing, lodging and retention of HSCs in the proper BM niche, which likely results in the impaired engraftment and long-term hematopoiesis. These results suggest that Cdc42 activity represents a critical regulator and coordinator of external and intrinsic cues that control microanatomical location, interaction with the surrounding microenvironment and cell cycle induction of HSCs.

The current Cdc42 conditional knockout model reveals unique HSC regulatory functions of Cdc42. While $Cdc42GAP^{-/-}$ hematopoietic progenitors show normal cell cycle progression but increased apoptosis due to increased JNK activity, $Cdc42^{-/-}$ HSCs display drastically increased cell cycle progression/entry but unaltered survival property. Nonetheless, both Cdc42 gain and loss of activity seems to alter hematopoietic progenitor actin structure and adhesion activity, suggesting that a tightly regulated Cdc42 activity is required for HSC adhesion and migration related functions such as homing, lodging and engraftment. One novel aspect of the present findings is that in the absence of Cdc42, LT-HSCs are found dislocated from the "restrictive" niche and move to a relative "proliferation/differentiation-promoting" marrow environment (Venezia, T. A. et al. (2004) PLoS Biol 2, e301). The reduced retention in the microenvironment, resulting from actin structure and adhesion defects, coupled with altered expression of cell cycle regulatory proteins such as $p21^{Cip1}$ and c-Myc, propels $cdc42^{-/-}$ LT-HSCs to enter into an active cell cycle, giving rise to increased ST-HSCs and progenitors. These effects appear to be uniquely regulated by Cdc42, since Rac1 and Rac2, two of closely related Rho GTPases, are important in HSC retention in the BM niche and for HSC survival and cell cycle progression but are not involved in the maintenance of HSC quiescent state (Cancelas, J. A. et al. (2005) Nat Med 11, 886-91; Gu, Y. et al. (2003) Science 302, 445-9), whereas RhoA, another related Rho GTPase, may be involved in HSC engraftment but not retention in the BM niche (Ghiaur, G. et al. (2006) Blood). Another novel aspect of the present studies is the implication that Cdc42 function in HSCs is unique, as Cdc42 is known for neuro-stem/progenitor cell polarity establishment and for skin stem/progenitor differentiation into the follicle lineage (Chen, L. et al. (2006) Proc Natl Acad Sci USA; Wu, X. et al. (2006) Genes Dev 20, 571-85; Cappello, S. et al. (2006) Nat Neurosci 9, 1099-1107), and is required for supporting cell cycle progression through the G1/S phase, rather than maintaining cell cycle quiescence, in mouse embryonic fibroblasts (Yang, L. et al. (2006) Mol Biol Cell). The findings further suggest a novel avenue for manipulating the HSC cell cycle status as well as the HSC-niche interaction in future therapeutic applications.

EXAMPLE 12

Targeting Cdc42 by the each of the following four compounds:

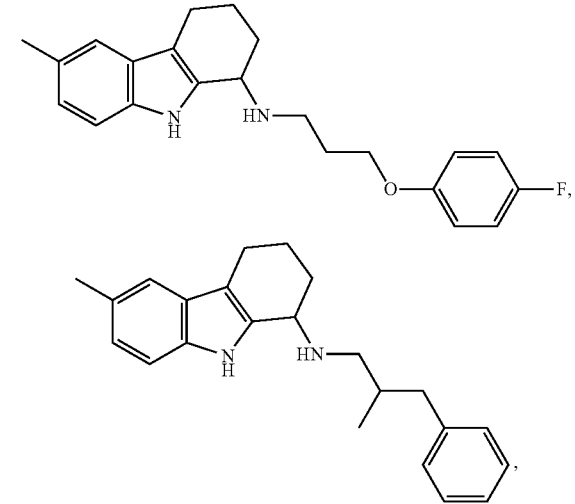

-continued

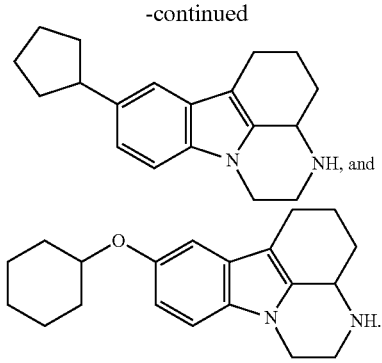

can mobilize the murine and human hematopoietic stem and progenitor cells in vivo, mimicking the effect of Cdc42 knockout and the effect of CASIN. As described herein, CASIN is illustrated by the following structure:

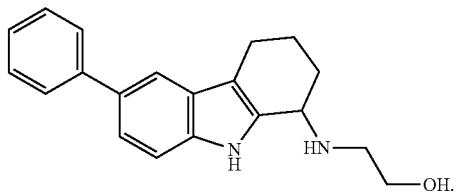 [SMILES: OCCNC1CCCc2c1[nH]c1ccc(-c3ccccc3)cc21]

The effects of each of the four compounds on human hematopoietic cell mobilization are tested using a well established preclinical in vivo model (NOD/SCID-Hcb) of human hematopoietic function as described above, where fresh $CD34^+$ hCB cells are transplanted into sub-lethally irradiated NOD/SCIDs by intrafemoral injection, and repopulate and maintain human hematopoietic reconstitution in the bone marrow of NOD/SCID recipient mice Intravenous injections of each of the four compounds are applied when human cells are well engrafted in the NOD/SCID recipients. By 20 min post administration of each of the four compounds individually, a significant amount of human $CD45^+$ hematopoietic cells mobilize to the peripheral blood for each mouse in the test group, while control injections do not cause any significant mobilization in comparison. Therefore, the data clearly demonstrate the potential utilities of each of the four compounds tested as a mobilizer of HSCs.

What is claimed is:

1. A method for mobilizing peripheral blood precursor cells from bone marrow into peripheral blood comprising: administering to a subject in need of treatment an effective amount of at least one Cdc42-specific inhibitor, wherein the Cdc42-specific inhibitor is CASIN.

2. A method for facilitating hematopoietic reconstitution of peripheral blood precursor cells in a subject's hematopoietic organs, comprising: a) administering to the subject an effective amount of at least one Cdc42-specific inhibitor in the precursor cells; b) isolating mobilized peripheral blood precursor cells from the peripheral circulation of the subject; and c) infusing the isolated mobilized peripheral blood precursor cells into the subject, wherein the Cdc42-specific inhibitor is CASIN.

* * * * *

UNITED STATES PATENT AND TRADEMARK OFFICE
CERTIFICATE OF CORRECTION

PATENT NO.       : 8,383,124 B2
APPLICATION NO.  : 12/922026
DATED            : February 26, 2013
INVENTOR(S)      : Zheng It is certified that error appears in the above-identified patent and that said Letters Patent is hereby corrected as shown below:

In column 2 (Title page 1 item 56) at line 1, Under Other Publications, change "Hematopoitic" to --Hematopoietic--.

In the Drawings:
Sheet 17 of 38 (Y-axis, FIG. 10) at line 1, Change "adoptotic" to --apoptotic--.
Sheet 34 of 38 (FIG. 16E) at line 1, Change "Phallodin" to --Phalloidin--.

In the Specifications:
In column 1 (above CROSS-REFERENCE TO RELATED APPLICATIONS) at lines 4-5, Add
"STATEMENT REGARDING FEDERALLY SPONSORED R&D
This invention was made with government support under GM053943 and CA105117 awarded by the National Institutes of Health. The government has certain rights in the invention."
In column 7 at line 60, Change "anemial," to --anemia,--.
In column 9 at line 5, Change "substitutents" to --substituents--.
In column 12 at line 42, Change "does-dependent" to --dose-dependent--.
In column 12 at line 53, Change "Immunofluoresence" to --Immunofluorescence--.
In column 13 at line 62, Change "cytomety" to --cytometry--.
In column 14 at line 3, Change "GSK-313" to --GSK-3β--.
In column 16 at line 55, Change "hematopoeitic" to --hematopoietic--.
In column 17 at line 9, Change "hematopoeitic" to --hematopoietic--.
In column 19 at line 34, Change "IC$_{so}$" to --IC$_{50}$--.
In column 22 at lines 4-5, Change "enymatic" to --enzymatic--.

Signed and Sealed this
Twenty-ninth Day of October, 2013

Teresa Stanek Rea
*Deputy Director of the United States Patent and Trademark Office*

CERTIFICATE OF CORRECTION (continued)
U.S. Pat. No. 8,383,124 B2

In column 24 at line 12, Change "substitutents" to --substituents--.

In column 29 at line 28, Change "substitutent" to --substituent--.

In column 30 at line 7, Change "substitutent" to --substituent--.

In column 30 at line 59, Change "pyrrolidione," to --pyrrolidinone,--.

In column 31 at line 2, Change "C3-8-cycloalkyl" to --$C_{3-8}$-cycloalkyl--.

In column 32 at line 55, Change "ephithelial" to --epithelial--.

In column 34 at line 34, After "the" delete "a".

In column 34 at line 36, Change "stochiochemistry." to --stoichiochemistry.--.

In column 35 at line 34, Change "psuedo" to --pseudo--.

In column 38 at lines 38-39, Change "ubiqutination," to --ubiquitination,--.

In column 39 at line 33, Change "allogenic" to --allogeneic--.

In column 40 at lines 44-45, Change "polymorphoneuclear" to --polymorphonuclear--.

In column 40 at line 52, Change "polymorphoneuclear" to --polymorphonuclear--.

In column 41 at line 49, Change "Szary" to --Sezary--.

In column 42 at lines 18-19, Change "spenomegaly," to --splenomegaly,--.

In column 42 at line 19, Change "spenic" to --splenic--.

In column 42 at line 47, Change "polyanglitis" to --polyangiitis--.

In column 42 at line 49, Change "thromboanglitis" to --thromboangiitis--.

In column 42 at line 63, Change "hemangloendothelioma," to --hemangioendothelioma,--.

In column 43 at line 40, Change "Szary" to --Sezary--.

In column 44 at line 29, Change "intrehepatic" to --intrahepatic--.

In column 48 at line 27, Change "M1H));" to --MIH));--.

In column 49 at line 35, Change "tiripazamine," to --tirapazamine,--.

In column 52 at line 37, Change "guandine" to --guanidine--.

In column 52 at line 42, Change "fonic acid," to --folic acid,--.

In column 53 at line 7, Change "amphotsics" to --amphoterics--.

In column 57 at line 6, Change "capronic" to --caproic--.

In column 57 at line 6, Change "myristinic" to --myristic--.

In column 57 at line 20, Change "discarboxylic" to --dicarboxylic--.

In column 58 at line 64, Change "sodium bisulfate;" to --sodium bisulfite;--.

In column 59 at line 53, Change "of" to --or--.

In column 63 at line 10, Change "mg/kg/day" to --µg/kg/day--.

In column 64 at line 34, Change "cisplatinun," to --cisplatin,--.

In column 64 at line 36, Change "carbaplatinum," to --carboplatin,--.

CERTIFICATE OF CORRECTION (continued)
U.S. Pat. No. 8,383,124 B2

In column 66 at line 2, Change "fibroblats" to --fibroblasts--.

In column 66 at line 5, Change "lamellipoidia," to --lamellipodia,--.

In column 67 at line 24, Change "(FIG. 20." to --(FIG.2f).--.

In column 68 at lines 6-7, Change "(FIG. 30." to --(FIG.3f).--.

In column 68 at line 44, Change "NOD/SCIDS" to --NOD/SCIDs--.

In column 69 at lines 40-41, Change "NOD/SCIDyC-/-" to --NOD/SCIDγC-/- --.

In column 73 at line 39, Change "posinjection" to --postinjection--.

In column 75 at line 26, Change "Flk-21nt" to --Flk-2int--.

In column 75 at line 27, Change "(Lin-/c-Kit+/Sca-1+/Thy1.1int/FLK21nt)," to --(Lin-/c-Kit+/Sca-1+/Thy1.1int/FLK2int),--.

In column 75 at line 64, Change "introperitoneally" to --intraperitoneally--.